US011091776B2

(12) United States Patent
Wilson et al.

(10) Patent No.: US 11,091,776 B2
(45) Date of Patent: Aug. 17, 2021

(54) AAV8 MUTANT CAPSIDS AND COMPOSITIONS CONTAINING SAME

(71) Applicant: The Trustees of the University of Pennsylvania, Philadelphia, PA (US)

(72) Inventors: James M. Wilson, Philadelphia, PA (US); Qiang Wang, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 315 days.

(21) Appl. No.: 16/093,800

(22) PCT Filed: Apr. 13, 2017

(86) PCT No.: PCT/US2017/027392
§ 371 (c)(1),
(2) Date: Oct. 15, 2018

(87) PCT Pub. No.: WO2017/180854
PCT Pub. Date: Oct. 19, 2017

(65) Prior Publication Data

US 2019/0078119 A1 Mar. 14, 2019

Related U.S. Application Data

(60) Provisional application No. 62/323,389, filed on Apr. 15, 2016.

(51) Int. Cl.
*C12N 15/86* (2006.01)
*C07K 14/005* (2006.01)

(52) U.S. Cl.
CPC ............ *C12N 15/86* (2013.01); *C07K 14/005* (2013.01); *C12N 2710/10032* (2013.01); *C12N 2710/10033* (2013.01); *C12N 2710/10045* (2013.01); *C12N 2750/14122* (2013.01); *C12N 2750/14143* (2013.01); *C12N 2810/6027* (2013.01)

(58) Field of Classification Search
CPC ...................................................... C12N 15/86
See application file for complete search history.

(56) References Cited

U.S. PATENT DOCUMENTS

| | | | |
|---|---|---|---|
| 5,478,745 A | 12/1995 | Samulski et al. | |
| 5,972,596 A | 10/1999 | Pavlakis et al. | |
| 7,282,199 B2 | 10/2007 | Gao et al. | |
| 7,629,322 B2 | 12/2009 | Kleinschmidt et al. | |
| 2003/0138772 A1 | 7/2003 | Gao et al. | |
| 2007/0036760 A1 | 2/2007 | Wilson et al. | |
| 2009/0191597 A1 | 7/2009 | Samulski et al. | |
| 2012/0141422 A1 | 6/2012 | Barkats | |
| 2015/0139953 A1 | 5/2015 | Gao et al. | |
| 2015/0315612 A1 | 11/2015 | Wilson et al. | |
| 2015/0376240 A1* | 12/2015 | Cronin | A61P 27/02 424/93.2 |

FOREIGN PATENT DOCUMENTS

| | | |
|---|---|---|
| WO | WO 2006/110689 | 10/2006 |
| WO | WO 2011/038187 | 3/2011 |
| WO | WO 2011/126808 | 3/2011 |
| WO | WO 2013/155222 | 10/2013 |
| WO | WO 2014/011210 | 1/2014 |
| WO | WO 2014/124282 | 8/2014 |

OTHER PUBLICATIONS

Supplementary European Search Report and Written Opinion dated Nov. 22, 2019 in European Patent Application No. 17783123.7.

Applicant's Amendment and Response filed Jun. 1, 2020 in European Patent Application No. 17783123.7.

Amara et al, Control of a Mucosal Challenge and Prevention of AIDS by a Multiprotein DNA/MVA Vaccine, Science, Apr. 6, 2001; 292(5514): 69-74.

Barouch et al., Elicitation of high-frequency cytotoxic T-lymphocyte responses against both dominant and subdominant simian-human immunodeficiency virus epitopes by DNA vaccination of rhesus monkeys, J. Virol., Mar. 2001; 75(5): 2462-7.

Donnelly et al., The cleavage activities of aphthovirus and cardiovirus 2A proteins, J. Gen. Virol., Jan. 1997; 78(Pt 1): 13-21.

Ellis et al., Zinc-finger nuclease-mediated gene correction using single AAV vector transduction and enhancement by Food and Drug Administration-approved drugs, Gene Therapy, Jan. 2013; 20(1): 35-42. Epub Jan. 19, 2012.

Fisher K et al., Transduction with recombinant adeno-associated virus for gene therapy is limited by leading-strand synthesis, J Virol., Jan. 1996; 70(1): 520-32.

Furler et al., Recombinant AAV vectors containing the foot and mouth disease virus 2A sequence confer efficient bicistronic gene expression in cultured cells and rat substantia nigra neurons, Gene Ther., Jun. 2001; 8(11): 864-73.

GenBank V00882.1, Rabbit (*O. cuniculus*) gene for beta-globin, Nov. 14, 2006.

GenBank X00182.1, Gallus gallus cytoplasmic beta-actin gene, Nov. 14, 2006.

Govindasamy et al., Structurally Mapping the Diverse Phenotype of Adeno-Associated Virus Serotype 4, J Virol., Dec. 2006; 80(23):11556-70. Epub Sep. 13, 2006.

Gurda et al., Mapping a neutralizing epitope onto the capsid of adeno-associated virus serotype 8, J. Virol., Aug. 2012; 86(15):7739-51. Epub May 16, 2012.

Klump et al., Retroviral vector-mediated expression of HoxB4 in hematopoietic cells using a novel coexpression strategy, Gene Ther., May 2001; 8(10): 811-7.

Limberis et al., Transduction efficiencies of novel AAV vectors in mouse airway epithelium in vivo and human ciliated airway epithelium in vitro, Mol Ther., Feb. 2009; 17(2): 294-301. Epub Dec. 9, 2008.

(Continued)

*Primary Examiner* — Thaian N. Ton
*Assistant Examiner* — David A. Montanari
(74) *Attorney, Agent, or Firm* — Howson & Howson LLP

(57) ABSTRACT

Provided herein are AAV8 mutant capsids and rAAV comprising the same. In one embodiment, vectors employing the AAV8 mutant capsid show increased transduction in a selected tissue as compared to AAV8.

12 Claims, 28 Drawing Sheets

Specification includes a Sequence Listing.

(56) References Cited

OTHER PUBLICATIONS

Lochrie et al., Mutations on the external surfaces of adeno-associated virus type 2 capsids that affect transduction and neutralization, J Virol., Jan. 2006; 80(2): 821-34.
Lock et al., Absolute determination of single-stranded and self-complementary adeno-associated viral vector genome titers by droplet digital PCR, Hum Gene Ther Methods, Apr. 2014; 25(2): 115-25. Epub Feb. 14, 2014.
Lock et al., Rapid, Simple, and Versatile Manufacturing of Recombinant Adeno-Associated Viral Vectors at Scale, Human Gene Therapy, Oct. 2010; 21(10): 1259-71.
McLaughlin et al., Adeno-associated virus general transduction vectors: analysis of proviral structures, J. Virol., Jun. 1988; 62(6): 1963-73.
Millington-Ward et al., Suppression and Replacement Gene Therapy for Autosomal Dominant Disease in a Murine Model of Dominant Retinitis Pigmentosa, Molecular Therapy, Apr. 2011; 19(4): 642-9. Epub Jan. 11, 2011.
Miyatake et al., Transcriptional Targeting of Herpes Simplex Virus for Cell-Specific Replication, J. Virol., Jul. 1997; 71(7):5124-32.
Mussolino, AAV-mediated photoreceptor transduction of the pig cone-enriched retina, Gene Ther, vol. 18(7):637-45, Jul. 2011 (ePub Mar. 2011).
NCBI Reference Sequence: NC_001401.2, Adeno-associated virus—2, complete genome, Dec. 2, 2014.
Nicoud et al., Development of photoreceptor-specific promoters and their utility to investigate EIAV lentiviral vector mediated gene transfer to photoreceptors, J Gene Med., Dec. 2007; 9(12): 1015-23.
O'Reilly et al., RNA interference-mediated suppression and replacement of human rhodopsin in vivo, Am J Hum Genet., Jul. 2007; 81(1): 127-35. Epub May 23, 2007.
Rasowo et al., Development of Novel Muscle-Specific Adeno-Associated Viral Vector Constructs for Gene Therapy of Duchenne Muscular Dystrophy, European Scientific Journal, Jun. 2014, edition vol. 10, No. 18: 23-37.
Sandig et al., HBV-derived promoters direct liver-specific expression of an adenovirally transduced LDL receptor gene. Gene Ther., Nov. 1996; 3(11):1002-9.
Sonntag et al., A viral assembly factor promotes AAV2 capsid formation in the nucleolus, Proc Natl Acad Sci U S A, Jun. 1, 2010; 107(22): 10220-5.
Sun et al., Adeno-associated virus-delivered short hairpin-structured RNA for androgen receptor gene silencing induces tumor eradication of prostate cancer xenografts in nude mice: a preclinical study, Int J Cancer, Feb. 1, 2010; 126(3): 764-74.
Wang et al. Sustained correction of disease in naive and AAV2-pretreated hemophilia B dogs: AAV2/8-mediated, liver-directed gene therapy, Blood, Apr. 15, 2005; 105(8): 3079-86. Epub Jan. 6, 2005.
Wang et al., Construction and analysis of compact muscle-specific promoters for AAV vectors, Gene Ther., Nov. 2008; 15(22): 1489-99. Epub Jun. 19, 2008.
Wang et al., Sustained correction of bleeding disorder in hemophilia B mice by gene therapy, Proc. Natl. Acad. Sci. USA, Mar. 30, 1999; 96(7): 3906-10.
Wu et al., Effect of Genome Size on AAV Vector Packaging, Mol Ther., Jan. 2010; 18(1): 80-86. Epub Nov. 10, 2009.
Zeitz et al., Whole-exome sequencing identifies LRIT3 mutations as a cause of autosomal-recessive complete congenital stationary night blindness, Am J Hum Genet, Jan. 10, 2013; 92(1): 67-75. Epub Dec. 13, 2012.
International Search Report and Written Opinion issued in International Patent Application No. PCT/US17/27392, dated Sep. 15, 2017.

* cited by examiner

```
                          1                                                50
         AAV8    (1)   MAADGYLPDWLEDNLSEGIREWWALKPGAPKPKANQQKQDDGRGLVLPGY
     AAV8.TR1    (1)   MAADGYLPDWLEDNLSEGIREWWALKPGAPKPKANQQKQDDGRGLVLPGY
     AAV8.T20    (1)   MAADGYLPDWLEDNLSEGIREWWDLKPGAPKPKANQQKQDDGRGLVLPGY
AVV3G1.Triple    (1)   MAADGYLPDWLEDNLSEGIREWWALKPGAPKPKANQQKQDDGRGLVLPGY
                       51                                               100
         AAV8   (51)   KYLGPFNGLDKGEPVNAADAAALEHDKAYDQQLQAGDNPYLRYNHADAEF
     AAV8.TR1   (51)   KYLGPFNGLDKGEPVNAADAAALEHDKAYDQQLQAGDNPYLRYNHADAEF
     AAV8.T20   (51)   KYLGPFNGLDKGEPVNAADAAALEHDKAYDQQLKAGDNPYLRYNHADAEF
AVV3G1.Triple   (51)   KYLGPFNGLDKGEPVNAADAAALEHDKAYDQQLQAGDNPYLRYNHADAEF
                       101                                              150
         AAV8  (101)   QERLQEDTSFGGNLGRAVFQAKKRVLEPLGLVEEGAKTAPGKKRPVEPSP
     AAV8.TR1  (101)   QERLQEDTSFGGNLGRAVFQAKKRVLEPLGLVEEGAKTAPGKKRPVEPSP
     AAV8.T20  (101)   QERLQEDTSFGGNLGRAVFQAKKRVLEPLGLVEEGAKTAPGKKRPVEPSP
AVV3G1.Triple  (101)   QERLQEDTSFGGNLGRAVFQAKKRVLEPLGLVEEGAKTAPGKKRPVEPSP
                       151                                              200
         AAV8  (151)   QRSPDSSTGIGKKGQQPARKRLNFGQTGDSESVPDPQPLGEPPAAPSGVG
     AAV8.TR1  (151)   QRSPDSSTGIGKKGQQPARKRLNFGQTGDSESVPDPQPLGEPPAAPSGVG
     AAV8.T20  (151)   QRSPDSSTGIGKTGQQPAKKRLNFGQTGDSESVPDPQPIGEPPAGPSGLG
AVV3G1.Triple  (151)   QRSPDSSTGIGKKGQQPARKRLNFGQTGDSESVPDPQPLGEPPAAPSGVG
                       201                                              250
         AAV8  (201)   PNTMAAGGGAPMADNNEGADGVGSSSGNWHCDSTWLGDRVITTSTRTWAL
     AAV8.TR1  (201)   PNTMAAGGGAPMADNNEGADGVGSSSGNWHCDSTWLGDRVITTSTRTWAL
     AAV8.T20  (201)   SGTMAAGGGAPMADNNEGADGVGSSSGNWHCDSTWLGDRVITTSTRTWAL
AVV3G1.Triple  (201)   PNTMAAGGGAPMADNNEGADGVGSSSGNWHCDSTWLGDRVITTSTRTWAL
                       251                                              300
         AAV8  (251)   PTYNNHLYKQISNGTSGGATNDNTYFGYSTPWGYFDFNRFHCHFSPRDWQ
     AAV8.TR1  (251)   PTYNNHLYKQISSDTHG-ATNDNTYFGYSTPWGYFDFNRFHCHFSPRDWQ
     AAV8.T20  (251)   PTYNNHLYKQISSGTHG-ATNDNTYFGYSTPWGYFDFNRFHCHFSPRDWQ
AVV3G1.Triple  (251)   PTYNNHLYKQISSGTHG-ATNDNTYFGYSTPWGYFDFNRFHCHFSPRDWQ
                       301                                              350
         AAV8  (301)   RLINNNWGFRPKRLSFKLFNIQVKEVTQNEGTKTIANNLTSTIQVFTDSE
     AAV8.TR1  (300)   RLINNNWGFRPKRLSFKLFNIQVKEVTQNEGTKTIANNLTSTIQVFTDSE
     AAV8.T20  (300)   RLINNNWGFRPKRLSFKLFNIQVKEVTQNEGTKTIANNLTSTIQVFTDSE
AVV3G1.Triple  (300)   RLINNNWGFRPKRLSFKLFNIQVKEVTQNEGTKTIANNLTSTIQVFTDSE
```

FIGURE 3A

```
                          351                                              400
AAV8            (351) YQLPYVLGSAHQGCLPPFPADVFMIPQYGYLTLNNGSQAVGRSSFYCLEY
AAV8.TR1        (350) YQLPYVLGSAHQGCLPPFPADVFMIPQYGYLTLNNGSQAVGRSSFYCLEY
AAV8.T20        (350) YQLPYVLGSAHQGCLPPFPADVFMIPQYGYLTLNNGSQAVGRSSFYCLEY
AVV3G1.Triple   (350) YQLPYVLGSAHQGCLPPFPADVFMIPQYGYLTLNNGSQAVGRSSFYCLEY
                      401                                              450
AAV8            (401) FPSQMLRTGNNFQFTYTFEDVPFHSSYAHSQSLDRLMNPLIDQYLYYLSR
AAV8.TR1        (400) FPSQMLRTGNNFQFTYTFEDVPFHSSYAHSQSLDRLMNPLIDQYLYYLSR
AAV8.T20        (400) FPSQMLRTGNNFQFTYTFEDVPFHSSYAHSQSLDRLMNPLIDQYLYYLSR
AVV3G1.Triple   (400) FPSQMLRTGNNFQFTYTFEDVPFHSSYAHSQSLDRLMNPLIDQYLYYLSR
                      451                                              500
AAV8            (451) TQTTGGTANTQTLGFSQGGPNTMANQAKNWLPGPCYRQQRVSTTTGQNNN
AAV8.TR1        (450) TQTTDGSGLTQTLGFSQGGPNTMANQAKNWLPGPCYRQQRVSTTTGQNNN
AAV8.T20        (450) TQTTGGSRPTQTLGFSQGGPNTMANQAKNWLPGPCYRQQRVSTTTGQNNN
AVV3G1.Triple   (450) TQTTGGSRPTQTLGFSQGGPNTMANQAKNWLPGPCYRQQRVSTTTGQNNN
                      501                                              550
AAV8            (501) SNFAWTAGTKYHLNGRNSLANPGIAMATHKDDEERFFPSNGILIFGKQNA
AAV8.TR1        (500) SNFAWTAGTKYHLNGRNSLANPGIAMATHKDDEERFFPSNGILIFGKQNA
AAV8.T20        (500) SNFAWTAGTKYHLNGRNSLANPGIAMATHKDDEERFFPSNGILIFGKQNA
AVV3G1.Triple   (500) SNFAWTAGTKYHLNGRNSLANPGIAMATHKDDEERFFPSNGILIFGKQNA
                      551                                              600
AAV8            (551) ARDNADYSDVMLTSEEEIKTTNPVATEEYGIVADNLQQQNTAPQIGTVNS
AAV8.TR1        (550) ARDNADYSDVMLTSEEEIKTTNPVATEEYGIVGDNLQLYNTAPGSVFVNS
AAV8.T20        (550) ARDNADYSDVMLTSEEEIKTTNPVATEEYGIVGDNLQLYNTAPGSVFVNS
AVV3G1.Triple   (550) ARDNADYSDVMLTSEEEIKTTNPVATEEYGIVGDNLQLYNTAPGSVFVNS
                      601                                              650
AAV8            (601) QGALPGMVWQNRDVYLQGPIWAKIPHTDGNFHPSPLMGGFGLKHPPPQIL
AAV8.TR1        (600) QGALPGMVWQNRDVYLQGPIWAKIPHTDGNFHPSPLMGGFGLKHPPPQIL
AAV8.T20        (600) QGALPGMVWQNRDVYLQGPIWAKIPHTDGNFHPSPLMGGFGLKHPPPQIL
AVV3G1.Triple   (600) QGALPGMVWQNRDVYLQGPIWAKIPHTDGNFHPSPLMGGFGLKHPPPQIL
                      651                                              700
AAV8            (651) IKNTPVPADPPTTFNQSKLNSFITQYSTGQVSVEIEWELQKENSKRWNPE
AAV8.TR1        (650) IKNTPVPADPPTTFNQSKLNSFITQYSTGQVSVEIEWELQKENSKRWNPE
AAV8.T20        (650) IKNTPVPADPPTTFNQSKLNSFITQYSTGQVSVEIEWELQKENSKRWNPE
AVV3G1.Triple   (650) IKNTPVPADPPTTFNQSKLNSFITQYSTGQVSVEIEWELQKENSKRWNPE
                      701                                  738
AAV8            (701) IQYTSNYYKSTSVDFAVNTEGVYSEPRPIGTRYLTRNL
AAV8.TR1        (700) IQYTSNYYKSTSVDFAVNTEGVYSEPRPIGTRYLTRNL
AAV8.T20        (700) IQYTSNYYKSTSVDFAVNTEGVYSEPRPIGTRYLTRNL
AVV3G1.Triple   (700) IQYTSNYYKSTSVDFAVNTEGVYSEPRPIGTRYLTRNL
```

FIGURE 3B

AAV3G1.Triple

AAV8

AAV8

AAV3G1.Triple

Vector genome copy distribution. The samples were from the same study as FIGURE 8C AAV8.Triple Intravenous administration shows that AAV8.Triple is ~ 18% of AAV8 and AAV8.TR1 is ~52% of AAV8.

AAV8 MUTANT CAPSIDS AND COMPOSITIONS CONTAINING SAME

CROSS-REFERENCE TO RELATED APPLICATIONS

This is a National Stage Entry under 35 U.S.C. 371 of International Patent Application No. PCT/US2017/027392, filed Apr. 13, 2017, which claims the benefit under 35 USC 119(e) of U.S. Provisional Patent Application No. 62/323,389, filed Apr. 15, 2016. These applications are incorporated by reference herein.

INCORPORATION—BY-REFERENCE OF MATERIAL SUBMITTED IN ELECTRONIC FORM

Applicant hereby incorporates by reference the Sequence Listing material filed in electronic form herewith. This file is labeled "UPN-16-7726PCT_ST25.txt".

BACKGROUND OF THE INVENTION

Adeno-associated viruses (AAV) hold great promise in human gene therapy and have been widely used to target liver, muscle, heart, brain, eye, kidney and other tissues in various studies due to its ability to provide long-term gene expression and lack of pathogenicity. AAVs belong to the parvovirus family and each contains a single strand DNA flanked by two inverted terminal repeats. Dozens of naturally occurring AAV capsids have been reported their unique capsid structures enable them to recognize and transduce different cell types and organs.

Since the first trial which started in 1981, there has not been any vector-related toxicity reported in clinical trials of adeno-associated virus (AAV) vector based gene therapy. The ever-accumulating safety records of AAV vector in clinical trials, combined with demonstrated efficacy, show that AAV is a good platform to work with. Another attractive feature is that AAV is relatively easy to be manipulated as AAV is a single-stranded DNA virus with a small genome (~4.7 kb) and simple genetic components-inverted terminal repeats (ITR), the Rep and Cap genes. Only the ITRs and AAV capsid protein are required in AAV vectors, with the ITRs serving as replication and packaging signals for vector production and the capsid proteins playing a central role by forming capsids to accommodate vector genome DNA, determining tissue tropism and delivering vector genomic DNA into target cells. There have been mainly four ways to obtain AAV capsid genes: isolating AAVs from cultures or tissues samples, AAV directed evolution, shuffling, and rational design.

AAV8 has been shown to effectively transduce liver, muscle. In addition, AAV8-mediated hFIX gene transfer by a single peripheral-vein infusion consistently leads to long-term expression of the FIX transgene at therapeutic levels without acute or long-lasting toxicity in patients with severe hemophilia B.

AAV vectors possess many advantages in gene transfer, but there are still some problems to be solved. Thus, more effective AAV vectors are needed.

SUMMARY OF THE INVENTION

In one aspect, an adeno-associated virus is provided. The virus comprises an AAV8 mutant capsid. In one embodiment, the capsid has the sequence of SEQ ID NO: 18 and is termed AAV3G1. In another embodiment, the capsid has the sequence of SEQ ID NO: 20 and is termed AAV8.T20. In yet another embodiment, the capsid has the sequence of SEQ ID NO: 22 and is termed AAV8.TR1. In another aspect, a nucleic acid encoding a capsid as described herein is provided. In one embodiment, the capsid is encoded by SEQ ID NO: 17 or a sequence sharing at least 95% identity therewith. In another embodiment, the capsid is encoded by SEQ ID NO: 19 or a sequence sharing at least 95% identity therewith. In another embodiment, the capsid is encoded by SEQ ID NO: 21 or a sequence sharing at least 95% identity therewith.

In another embodiment, the AAV which includes an AAV8 mutant capsid, includes at least a vp3 capsid having a mutation in at least one of the following regions, as compared to native AAV8 (SEQ ID NO: 34); i. as 263 to 267 (SEQ ID NO: 78); ii. as 457 to aa 459; iii. as 455 to as 459 (SEQ ID NO: 81); or iv. as 583 to as 597 (SEQ ID NO: 69). In one embodiment, the AAV having the AAV8 mutant capsid has increased transduction in a target tissue as compared to AAV8. In one embodiment, the target tissue is muscle, liver, lung, airway epithelium, neurons, eye, or heart. In another embodiment, the AAV having the AAV8 mutant capsid has an increased ability to escape AAV neutralizing antibodies as compared to native AAV8.

In one embodiment, the vp1 and or vp2 unique regions are derived from a different AAV than the AAV supplying the vp3 unique region (i.e., AAV8). In one embodiment, the AAV supplying the vp1 and vp2 sequences is rh.20. In one embodiment, the rh.20 vp1 sequence is SEQ ID NO: 88.

In another embodiment, the AAV further includes AAV inverted terminal repeats and a heterologous nucleic acid sequence operably linked to regulatory sequences which direct expression of a product encoded by the heterologous nucleic acid sequence in a target cell.

In another aspect, a method of transducing a target tissue is provided. In one embodiment, the method includes administering an AAV having a capsid as described herein. In one embodiment, a method of transducing liver tissue is provided, comprising administering an AAV having the AAV3G1 capsid. In another embodiment, a method of transducing muscle tissue is provided, comprising administering an AAV having the AAV3G1 capsid. In yet another embodiment, a method of transducing airway epithelium is provided, comprising administering an AAV having the AAV3G1 or AAV8.T20 capsid. In another embodiment, a method of transducing liver tissue is provided, comprising administering an AAV having the AAV8.TR1 capsid. In yet another embodiment, a method of transducing ocular cells is provided, comprising administering an AAV having the AAV3G1 capsid.

In yet another aspect, a method of generating a mutant AAV capsid having increased transduction for a target tissue, as compared to the wild type capsid is provided. The method includes performing mutagenesis at the contact region of a neutralizing antibody to the wild type capsid; and performing in vitro selection in the presence of the monoclonal antibody. In one embodiment, the method includes performing an additional mutation at a hypervariable region of the capsid. In another embodiment, the method further includes substituting the vp1 and/or vp2 unique sequences with the vp1 and/or vp2 sequences from a different AAV capsid.

In another aspect, a method of generating a recombinant adeno-associated virus (AAV) comprising an AAV capsid is provided. In one embodiment, the method includes culturing a host cell containing: (a) a molecule encoding an AAV capsid protein a capsid having a mutation in at least one of the following regions, as compared to native AAV8 (SEQ ID NO: 34); i. as 263 to 267 (SEQ ID NO: 78); ii. aa 457 to as 459; iii. as 455 to as 459 (SEQ ID NO: 81); or iv. as 583 to as 597 (SEQ ID NO: 69); (b) a functional rep gene; (c) a minigene comprising AAV inverted terminal repeats (ITRs) and a transgene; and (d) sufficient helper functions to permit packaging of the minigene into the AAV capsid protein.

In yet another aspect, a recombinant adeno-associated virus (AAV) is provided. In one embodiment, the rAAV includes an AAV capsid having an amino acid sequence selected from: SEQ ID NO: 2, 4, 6, 8, 10, 12, 14, 16, 18, 20, 22, 24, 26, 28, 30, and 32. Such capsids are sometimes referred to herein as the "AAV8 mutant capsid(s)". The rAAV further includes a non-AAV nucleic acid sequence. In another aspect, a nucleic acid molecule encoding an AAV capsid sequence is provided. In one embodiment, the nucleic acid sequence is selected from SEQ ID NO: 1, 3, 5, 7, 9, 11, 13, 15, 17, 19, 21, 23, 25, 27, 29, and 31.

In another aspect, an AAV capsid protein is provided. The AAV capsid has a mutation in at least one of the following regions, as compared to native AAV8 (SEQ ID NO: 34); i. aa 263 to 267 (SEQ ID NO: 78); ii. aa 457 to aa 459; iii. aa 455 to aa 459 (SEQ ID NO: 81); or iv. aa 583 to as 597 (SEQ ID NO: 69). In another aspect, a nucleic acid sequence encoding an AAV capsid as described herein, is provided.

In yet another aspect, a host cell transfected with an adeno-associated virus as described herein, is provided.

In another aspect, a composition is provided which includes at least an AAV as described herein and a physiologically compatible carrier, buffer, adjuvant, and/or diluent.

In yet another aspect, a method of delivering a transgene to a cell is provided. The method includes the step of contacting the cell with an AAV as described herein, wherein said rAAV comprises the transgene.

BRIEF DESCRIPTION OF THE FIGURES

FIGS. 3A-3B are a protein Alignment of AAV8, AAV3G1, AAV8.T20 and AAV8.TR1 as described herein.

DETAILED DESCRIPTION OF THE INVENTION

Figure 1A:
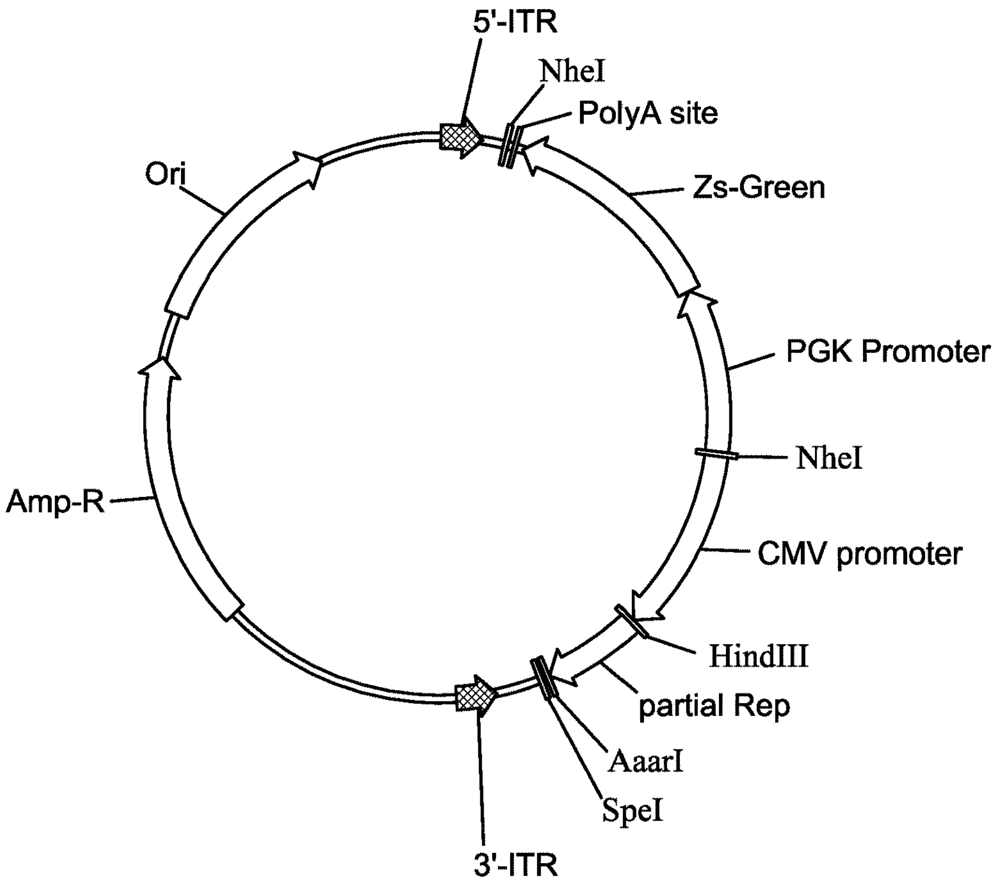
FIG. 1A provides a map of the plasmid used for AAV mutant library construction.
Figure 1B:
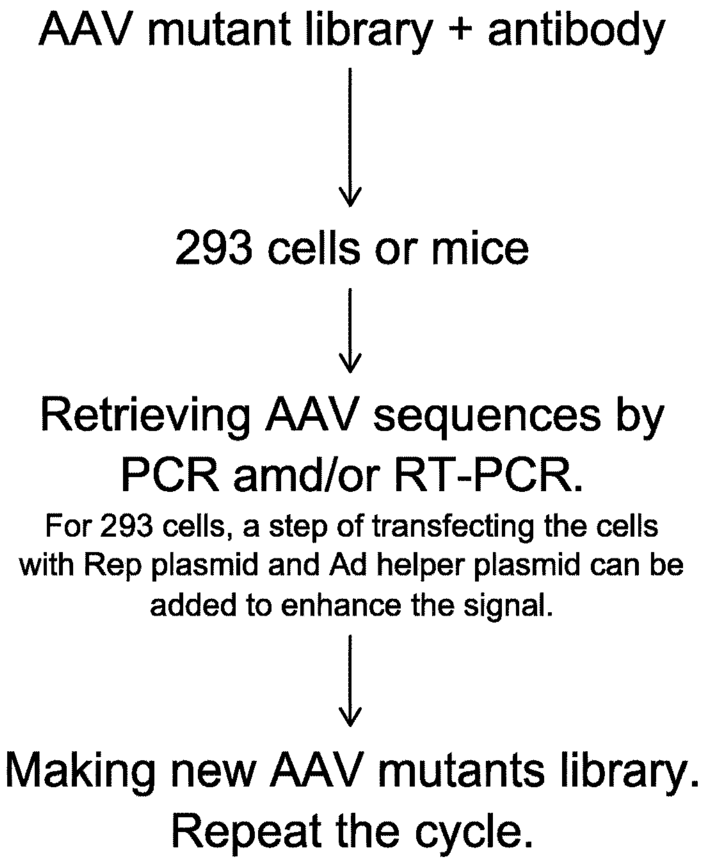
FIG. 1B illustrates the selection process of the AAV mutant library construction.

Adeno-associated virus (AAV)-based gene therapy is showing increasing promise, stimulated by encouraging results from clinical trials in recent years. Until now, AAV vectors utilizing the capsid have shown a tremendous potential for in vivo gene delivery with nearly complete transduction of many tissues in rodents after intravascular infusion. Thus, AAV8 is a logical starting point for designing improved vectors. To advance the platform, provided herein are AAV8 mutants having increased resistance to neutralizing antibodies, yield, expression, or transduction. The methods are directed to use of the AAV to target various tissues and treat various conditions.

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention. As used herein, the terms "a" or "an", refers to one or more, for example, "an ocular cell" is understood to represent one or more ocular cells. As such, the terms "a" (or "an"), "one or more," and "at least one" are used interchangeably herein. As used herein, the term "about" means a variability of 10% from the reference given, unless otherwise specified. While various embodiments in the specification are presented using "comprising" language, under other circumstances, a related embodiment is also intended to be interpreted and described using "consisting of" or "consisting essentially of" language.

With regard to the following description, it is intended that each of the compositions herein described, is useful, in another embodiment, in the methods of the invention. In addition, it is also intended that each of the compositions herein described as useful in the methods, is, in another embodiment, itself an embodiment of the invention.

As used herein, the term "target tissue" can refer to any cell or tissue which is intended to be transduced by the subject AAV vector. The term may refer to any one or more of muscle, liver, lung, airway epithelium, neurons, eye (ocular cells), or heart. In one embodiment, the target tissue is liver. In another embodiment, the target tissue is the eye.

As used herein, the term "ocular cells" refers to any cell in, or associated with the function of, the eye. The term may refer to any one or more of photoreceptor cells, including rod, cone and photosensitive ganglion cells, retinal pigment epithelium (RPE) cells, Mueller cells, bipolar cells, horizontal cells, amacrine cells. In one embodiment, the ocular cells are bipolar cells. In another embodiment, the ocular cells are horizontal cells. In another embodiment, the ocular cells are ganglion cells.

As used herein, the term "mammalian subject" or "subject" includes any mammal in need of the methods of treatment described herein or prophylaxis, including particularly humans. Other mammals in need of such treatment or prophylaxis include dogs, cats, or other domesticated animals, horses, livestock, laboratory animals, including non-human primates, etc. The subject may be male or female.

As used herein, the term "host cell" may refer to the packaging cell line in which the rAAV is produced from the plasmid. In the alternative, the term "host cell" may refer to the target cell in which expression of the transgene is desired.

A. THE AAV CAPSID

A recombinant AAV capsid protein as described herein is characterized by a variable protein 3 (vp3) having a mutation in at least one of the following regions, as compared to the native full length (vp1) AAV8 capsid sequence (SEQ ID NO: 34): i. aa 263 to 267 (SEQ ID NO: 78); ii. aa 457 to aa 459; iii. aa 455 to aa 459 (SEQ ID NO: 81); or iv. aa 583 to aa 597 (SEQ ID NO: 69). An AAV having such a capsid has increased transduction in a target tissue as compared to AAV8. Also encompassed by the invention are nucleic acid sequences encoding the novel AAV, capsids, and fragments thereof which are described herein.

As used herein, the term "native" refers to the native AAV sequence without mutation in i. as 263 to 267; ii. as 457 to as 459; iii. as 455 to as 459; or iv. as 583 to as 597 (using AAV8 numbering) of the capsid protein. However it is not intended that only naturally occurring AAV8 be the source of the wild type sequence. Useful herein are non-naturally occurring AAV, including, without limitation, recombinant, modified or altered, shuffled, chimeric, hybrid, evolved, synthetic, artificial, etc., AAV. This includes AAV with mutations in regions of the capsid other than in i. as 263 to 267; ii. aa 457 to as 459; iii. aa 455 to aa 459; or iv. as 583 to as 597 (using AAV8 numbering), provided they are used as the "starting sequence" for generating the mutant capsid described herein.

The AAV capsid consists of three overlapping coding sequences, which vary in length due to alternative start codon usage. These variable proteins are referred to as VP1, VP2 and VP3, with VP1 being the longest and VP3 being the shortest. The AAV particle consists of all three capsid proteins at a ratio of ~1:1:10 (VP1:VP2:VP3). VP3, which is comprised in VP1 and VP2 at the N-terminus, is the main structural component that builds the particle. The capsid protein can be referred to using several different numbering systems. For convenience, as used herein, the AAV sequences are referred to using VP1 numbering, which starts with aa 1 for the first residue of VP1. However, the capsid proteins described herein include VP1, VP2 and VP3 (used interchangeably herein with vp1, vp2 and vp3) with mutations in the corresponding region of the protein. In AAV8, the variable proteins correspond to VP1 (aa 1 to 738), VP2 (aa 138 to 738), and VP3 (aa 204 to 738) using the numbering of the full length VP1. The amino acid sequence of native AAV8 vp1 is shown in SEQ ID NO: 34.

The AAV capsid contains 9 hypervariable regions (HVR) which show the most sequence divergence throughout AAV isolates. See, Govindasamy et al, J Virol. 2006 December; 80(23):11556-70. Epub 2006 Sep. 13, which is incorporated herein by reference. Thus, when rationally designing new vectors, the HVRs are a rich target. In one embodiment, the AAV capsid has a mutation in the HVRVIII region. In one embodiment, an AAV capsid is provided which has a mutation in aa 583-aa597 as compared to the AAV8 native sequence. In one embodiment, the AAV capsid has an as 583-597 sequence as shown below in Table 1. Encompassed herein are capsid proteins and rAAV having capsid proteins having vp1, vp2 and/or vp3 sequences which include one of the amino acid sequences shown in Table 1.

TABLE 1

| capsid mutations | |
|---|---|
| SEQ. ID NO CONTAINING AA583-597 MUTATION | aa593 to aa597 Mutation |
| 2 | 583ADNLQQQNTAPQIGT597 (SEQ ID NO: 69) -->GDNLQLYNTAPGSVF (SEQ ID NO: 70) |
| 4 | 583ADNLQQQNTAPQIGT597 (SEQ ID NO: 69) -->SDNLQFRNTAPLWSS (SEQ ID NO: 71) |
| 6 | 583ADNLQQQNTAPQIGT597 (SEQ ID NO: 69) -->NDNLQVCNTAPDDVM (SEQ ID NO: 72) |
| 8 | 583ADNLQQQNTAPQIGT597 (SEQ ID NO: 69) -->CDNLQGYNTAPLCVA (SEQ ID NO:73) |
| 10 | 583ADNLQQQNTAPQIGT597 (SEQ ID NO: 69) -->VDNLQFLNTAPAGEA (SEQ ID NO:74) |
| 12 | 583ADNLQQQNTAPQIGT597 (SEQ ID NO: 69) -->LDNLQDGNTAPGACG (SEQ ID NO: 75) |
| 14 | 583ADNLQQQNTAPQIGT597 (SEQ ID NO: 69) -->WDNLQSENTAPSETS (SEQ ID NO: 76) |
| 16 | 583ADNLQQQNTAPQIGT597(SEQ ID NO: 69) -->SDNLQSCNTAPFAGA (SEQ ID NO: 77 |
| 18 | 583ADNLQQQNTAPQIGT597 (SEQ ID NO: 69) -->GDNLQLYNTAPGSVF (SEQ ID NO: 70) |

Additional mutations were made at the HVR.1 and HVR.IV regions. Thus, in one embodiment, the AAV capsid has a mutation in aa263 to aa267. In one embodiment, the AAV capsid has the mutation 263NGTSG267 (SEQ ID NO: 78)→SGTH (SEQ ID NO: 79). In another embodiment, the AAV capsid has the mutation 263NGTSG267 (SEQ ID NO: 78)→SDTH (SEQ ID NO: 80). Encompassed herein are capsid proteins and rAAV having capsid proteins having vp1, vp2 and/or vp3 sequences which include one of the amino acid sequences of SEQ ID NO: 79 or SEQ ID NO 80.

In one embodiment, the AAV capsid has a mutation in aa457 to aa459. In another embodiment, the AAV capsid has a mutation in aa455 to aa459. In one embodiment, the AAV capsid has the mutation 457TAN459→SRP. In one embodiment, the AAV capsid has the mutation 455GGTAN459 (SEQ ID NO: 81)→DGSGL (SEQ ID NO: 82). Encompassed herein are capsid proteins and rAAV having capsid proteins having vp1, vp2 and/or vp3 sequences which include one of the amino acid sequences of SEQ ID NO: 79 or SEQ ID NO 80.

In another embodiment, the vp1/vp2 unique regions of the AAV8 capsid (or other AAV capsid described herein) can be replaced with the vp1/vp2 regions from a different capsid. In one embodiment, the vp1/vp2 unique regions are replaced with the vp1/vp2 unique region of rh.20. In AAV8, the vp2 starts at amino acid 138, and the vp3 starts at amino acid 204, using AAV8 vp1 numbering. Thus, in one embodiment, the vp1/2 region of AAV8 (amino acids 1 to 203) is swapped for the corresponding portion (vp1/2) of another capsid. The vp1/2 regions in the swapped capsids may be of the same or different amino acid lengths. For example, in AAVrh.20, the vp1/2 region spans amino acids 1 to 202 of that sequence (SEQ ID NO: 88). See, Limberis et al, Mol Ther. 2009 February; 17(2): 294-301 (which is incorporated herein by reference). In another embodiment, the vp1/vp2 unique regions are replaced the vp1/vp2 unique region of AAV1, 6, 9, rh.8, rh.10, rh.20, hu.37, rh.2R, rh.43, rh.46, rh.64R1, hu.48R3, or cy.5R4. The vp1/2 regions can be readily determined based on alignments available in the art. See, e.g., WO 2006/110689, which is incorporated herein by reference.

The AAV capsid vp1 ORF includes a second ORF, which encodes the AAV assembly-activating protein (AAP). The AAP coding sequence of ORF2 initiates prior to the VP3 coding sequence. The AAV8 AAP native coding sequence is shown in SEQ ID NO: 35. The native AAP amino acid sequence is shown in SEQ ID NO: 36. In one embodiment, the AAV VP1 ORF is mutated to result in an alternative AAP amino acid sequence. Thus, in one embodiment, the AAV vp1 nucleic acid sequence shares at least 95% identity with the native AAV8 coding sequence. In another embodiment, the AAV vp1 nucleic acid sequence includes the ORF2 (AAP coding sequence) shown in SEQ ID NO: 37. In another embodiment, the AAV AAP amino acid sequence is shown in SEQ ID NO: 38. See, Sonntag et al, A viral assembly factor promotes AAV2 capsid formation in the nucleolus, Proc Natl Acad Sci USA. 2010 Jun. 1; 107(22): 10220-10225, which is incorporated herein by reference.

As shown in the examples below, the inventors have shown that the AAV termed AAV3G1 (also sometimes called AAV8.Triple or Triple) effectively transduces liver, muscle and airway epithelium. In fact, AAV3G1 shows about a 10 fold increase in transduction as compared to native AAV8, both i.m. and i.v., with various transgene cassettes such as CB7.CI.ffluciferase, CMV.LacZ and tMCK.human F9. A further recognized benefit of the AAV3G1 mutant is that it shows resistance to various antisera of monkey and human, as well as human IVIG (at levels 2 to 4 fold that of AAV8, with respect to human IVIG). Further, intranasal administration of AAV3G1 resulted in a transduction efficiency of airway epithelium 2 to 3 fold greater than that of AAV8. Thus, in one embodiment, the AAV capsid has a sequence of AAV3G1, as shown in SEQ ID NO: 18.

As shown in the examples below, the AAV termed AAV8.T20 transduces airway epithelium at levels approximately 10 fold greater than AAV8. Thus, in one embodiment, the AAV capsid has a sequence of AAV8.T20, as shown in SEQ ID NO: 20.

As shown in the examples below, the AAV termed AAV8.TR1 effectively transduces liver. Thus, in one embodiment, the AAV capsid has a sequence of AAV8.TR1, as shown in SEQ ID NO: 22.

In another embodiment, an AAV capsid is provided which has the sequence shown in SEQ ID NO: 2. In another embodiment, an AAV capsid is provided which has the sequence shown in SEQ ID NO: 4. In another embodiment, an AAV capsid is provided which has the sequence shown in SEQ ID NO: 6. In another embodiment, an AAV capsid is provided which has the sequence shown in SEQ ID NO: 8. In another embodiment, an AAV capsid is provided which has the sequence shown in SEQ ID NO: 10. In another embodiment, an AAV capsid is provided which has the sequence shown in SEQ ID NO: 12. In another embodiment, an AAV capsid is provided which has the sequence shown in SEQ ID NO: 14. In another embodiment, an AAV capsid is provided which has the sequence shown in SEQ ID NO: 16. In another embodiment, an AAV capsid is provided which has the sequence shown in SEQ ID NO: 18. In another embodiment, an AAV capsid is provided which has the sequence shown in SEQ ID NO: 20. In another embodiment, an AAV capsid is provided which has the sequence shown in SEQ ID NO: 22. In another embodiment, an AAV capsid is provided which has the sequence shown in SEQ ID NO: 24. In another embodiment, an AAV capsid is provided which has the sequence shown in SEQ ID NO: 26. In another embodiment, an AAV capsid is provided which has the sequence shown in SEQ ID NO: 28. In another embodiment, an AAV capsid is provided which has the sequence shown in SEQ ID NO: 30. In another embodiment, an AAV capsid is provided which has the sequence shown in SEQ ID NO: 32. In another embodiment, the AAV capsid has a vp1, vp2 or vp3 protein as shown in any of SEQ ID NO: 2, 4, 6, 8, 10, 12, 14, 16, 18, 20, 22, 24, 26, 28, 30 or 32 (which show the vp1 sequences).

In another aspect, nucleic acid sequences encoding the AAV viruses, capsids and fragments described herein are provided. Thus, in one embodiment, a nucleic acid encoding SEQ ID NO: 2, 4, 6, 8, 10, 12, 14, 16, 18, 20, 22, 24, 26, 28, 30 or 32 is provided. In one embodiment, a nucleic acid encoding the AAV3G1 capsid (SEQ ID NO: 18) is provided. In another embodiment, a nucleic acid encoding the AAV8.T20 capsid (SEQ ID NO: 20) is provided. In another embodiment, a nucleic acid encoding the AAV8.TR1 capsid (SEQ ID NO: 22) is provided. In one embodiment, the nucleic acid sequence encoding AAV3G1 is shown in SEQ ID NO: 17. In one embodiment, the nucleic acid sequence encoding AAV8.T20 is shown in SEQ ID NO: 19. In one embodiment, the nucleic acid sequence encoding AAV8.TR1 is shown in SEQ ID NO: 21. In another embodiment, the nucleic acid sequence encoding the capsid is shown in SEQ ID NO: 1, 3, 5, 7, 9, 11, 13, 15, 17, 19, 21, 23, 25, 27, 29 or 31, or a sequence sharing at least 80% identity with any of these sequences. In another embodiment, the nucleic acid molecular also encodes a functional AAV rep protein.

B. rAAV VECTORS AND COMPOSITIONS

In another aspect, described herein are molecules which utilize the AAV capsid sequences described herein, including fragments thereof, for production of viral vectors useful in delivery of a heterologous gene or other nucleic acid sequences to a target cell. In one embodiment, the vectors useful in compositions and methods described herein contain, at a minimum, sequences encoding a selected AAV capsid as described herein, e.g., an AAV3G1, AAV8.T20 or AAV.TR1 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV which differs from the wild type AAV providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein. Optionally, the vectors further contain a minigene comprising a selected transgene which is flanked by AAV 5' ITR and AAV 3' ITR In another embodiment, the AAV is a self-complementary AAV (sc-AAV) (See, US 2012/0141422 which is incorporated herein by reference). Self-complementary vectors package an inverted repeat genome that can fold into dsDNA without the requirement for DNA synthesis or base-pairing between multiple vector genomes. Because scAAV have no need to convert the single-stranded DNA (ssDNA) genome into double-stranded DNA (dsDNA) prior to expression, they are more efficient vectors. However, the trade-off for this efficiency is the loss of half the coding capacity of the vector, ScAAV are useful for small protein-coding genes (up to ~55 kd) and any currently available RNA-based therapy.

In one aspect, the vectors described herein contain nucleic acid sequences encoding an intact AAV capsid as described herein. In one embodiment, the capsid comprises amino acids 1 to 738 of SEQ ID NO: 18, 20 or 22. In another embodiment, the AAV has a recombinant AAV capsid comprising a mutation in at least one of the following regions, as compared to native AAV8 (SEQ ID NO: 34): i. aa 263 to 267 (SEQ ID NO: 78); ii. aa 457 to aa 459; iii. as 455 to aa 459 (SEQ ID NO: 81); or iv. aa 583 to aa 597 (SEQ ID NO: 69). In one embodiment, the AAV has increased transduction in a target tissue as compared to AAV8. In one embodiment, the AAV has a mutation which comprises 263NGTSG267 (SEQ ID NO: 78)→SGTH (SEQ ID NO: 79) or 263NGTSG267 (SEQ ID NO: 78)→SDTH (SEQ ID NO: 80). In another embodiment, the AAV has a mutation which comprises 457TAN459→SRP or 455GGTAN459 (SEQ ID NO: 81)→DGSGL (SEQ ID NO: 82). In yet another embodiment, the AAV has a mutation which comprises 583ADNLQQQNTAPQIGT597 (SEQ ID NO: 69)→GDNLQLYNTAPGSVF (SEQ ID NO: 70). In another embodiment, the AAV has the following mutations: 263NGTSG267 (SEQ ID NO: 78)→SGTH (SEQ ID NO: 79), 457TAN459→SRP, and 583ADNLQQQNTAPQIGT597 (SEQ ID NO: 69)→GDNLQLYNTAPGSVF (SEQ ID NO: 70).

In another embodiment, the AAV has a capsid protein in which the VP1/VP2 unique regions have been replaced with the VP1/VP2 unique regions from a capsid different than AAV8. In one embodiment, the VP1/VP2 unique regions are from AAVrh.20. In one embodiment, the rh.20 vp1 sequence is SEQ ID NO: 88.

Pseudotyped vectors, wherein the capsid of one AAV is replaced with a heterologous capsid protein, are useful herein. For illustrative purposes, AAV vectors utilizing the AAV8 mutant capsids described herein, with AAV2 ITRs are used in the examples described below. See, Mussolino et al, cited above. Unless otherwise specified, the AAV ITRs, and other selected AAV components described herein, may be individually selected from among any AAV serotype, including, without limitation, AAV1, AAV2, AAV3, AAV4, AAV5, AAV6, AAV7, AAV8, AAV9 or other known and unknown AAV serotypes. In one desirable embodiment, the ITRs of AAV serotype 2 are used. However, ITRs from other suitable serotypes may be selected. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like. In one embodiment, the AAV comprises the sequence of SEQ ID NO: 17, which corresponds to the full length DNA coding sequence of AAV3G1. In another embodiment, the AAV comprises the sequence of SEQ ID NO: 19, which corresponds to the full length DNA sequence of AAV8.T20. In another embodiment, the AAV comprises the sequence of SEQ ID NO: 21, which corresponds to the full length DNA sequence of AAV8.TR1.

The rAAV described herein also comprise a minigene. The minigene is composed of, at a minimum, a heterologous nucleic acid sequence (the transgene), as described below, and its regulatory sequences, and 5' and 3' AAV inverted terminal repeats (ITRs). It is this minigene which is packaged into a capsid protein and delivered to a selected target cell.

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a target cell. The heterologous nucleic acid sequence (transgene) can be derived from any organism. The AAV may comprise one or more transgenes.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), enhanced GFP (EGFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences include oncologic targets and viral diseases. See, for examples of such targets the oncologic targets and viruses identified below in the section relating to immunogens.

The transgene may be used to correct or ameliorate gene deficiencies, which may include deficiencies in which normal genes are expressed at less than normal levels or deficiencies in which the functional gene product is not expressed. Alternatively, the transgene may provide a product to a cell which is not natively expressed in the cell type or in the host. A preferred type of transgene sequence encodes a therapeutic protein or polypeptide which is expressed in a host cell. The invention further includes using multiple transgenes. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.,* 78(Pt 1): 13-21 (January 1997); Furler, S., et al, *Gene Ther.,* 8(11):864-873 (June 2001); Klump H., et al., *Gene Ther.,* 8(10):811-817 (May 2001). This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor $\alpha$ (TGF$\alpha$), platelet-derived growth factor (PDGF), insulin growth factors I and II (IGF-I and IGF-II), any one of the transforming growth factor $\beta$ superfamily, including TGF $\beta$, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors $\alpha$ and $\beta$, interferons $\alpha$, $\beta$, and $\gamma$, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encodes $\beta$-glucuronidase (GUSB)).

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Alternatively, or in addition, the vectors of the invention may contain AAV sequences of the invention and a transgene encoding a peptide, polypeptide or protein which induces an immune response to a selected immunogen. For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus, and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the Ni protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Between the HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. In addition, a variety of modifications to these antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R Amara, et al, Science, 292:69-74 (6 Apr. 2001). These proteins or subunits thereof may be delivered alone, or in combination via separate vectors or from a single vector.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; *pseudomonas*, acinetobacteria and eikenella; melioidosis; *salmonella; shigella; haemophilus; moraxella; H. ducreyi* (which causes chancroid); *brucella*; Franisella *tularensis* (which causes tularemia); *yersinia* (*pasteurella*); *streptobacillus moniliformis* and spirillum; Gram-positive bacilli include *Listeria monocytogenes*; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and chlamydial infections include: *Mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Health and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fever, all of which are currently classified as Category A agents; *Coxiella burnetti* (Q fever); *Brucella* species (brucellosis), *Burkholderia mallei* (glanders), *Ricinus communis* and its toxin (ricin toxin), Clostridiun *perfringens* and its toxin (epsilon toxin), *Staphylococcus* species and their toxins (enterotoxin B), all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of T cell receptors (TCRs) which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a nucleic acid molecule that encodes at least one of these polypeptides will elicit an immune response that will target T cells involved in scleroderma.

In one desirable embodiment, the transgene is selected to provide optogenetic therapy. In optogenetic therapy, artificial photoreceptors are constructed by gene delivery of light-activated channels or pumps to surviving cell types in the remaining retinal circuit. This is particularly useful for patients who have lost a significant amount of photoreceptor function, but whose bipolar cell circuitry to ganglion cells and optic nerve remains intact. In one embodiment, the heterologous nucleic acid sequence (transgene) is an opsin. The opsin sequence can be derived from any suitable single- or multicellular-organism, including human, algae and bacteria. In one embodiment, the opsin is rhodopsin, photopsin, L/M wavelength (red/green)-opsin, or short wavelength (S) opsin (blue). In another embodiment, the opsin is channelrhodopsin or halorhodopsin.

In another embodiment, the transgene is selected for use in gene augmentation therapy, i.e., to provide replacement copy of a gene that is missing or defective. In this embodiment, the transgene may be readily selected by one of skill in the art to provide the necessary replacement gene. In one embodiment, the missing/defective gene is related to an ocular disorder. In another embodiment, the transgene is NYX, GRM6, TRPM1L or GPR179 and the ocular disorder is Congenital Stationary Night Blindness. See, e.g., Zeitz et al, Am J Hum Genet. 2013 Jan. 10; 92(1):67-75. Epub 2012 Dec. 13 which is incorporated herein by reference. In another embodiment, the transgene is RPGR.

In another embodiment, the transgene is selected for use in gene suppression therapy, i.e., expression of one or more native genes is interrupted or suppressed at transcriptional or translational levels. This can be accomplished using short hairpin RNA (shRNA) or other techniques well known in the art. See, e.g., Sun et al, Int J Cancer. 2010 Feb. 1; 126(3): 764-74 and O'Reilly M, et al. Am J Hum Genet. 2007 July; 81(1):127-35, which are incorporated herein by reference. In this embodiment, the transgene may be readily selected by one of skill in the art based upon the gene which is desired to be silenced.

In another embodiment, the transgene comprises more than one transgene. This may be accomplished using a single vector carrying two or more heterologous sequences, or using two or more AAV each carrying one or more heterologous sequences. In one embodiment, the AAV is used for gene suppression (or knockdown) and gene augmentation co-therapy. In knockdown/augmentation co-therapy, the defective copy of the gene of interest is silenced and a non-mutated copy is supplied. In one embodiment, this is accomplished using two or more co-administered vectors. See, Millington-Ward et al, Molecular Therapy, April 2011, 19(4):642-649 which is incorporated herein by reference. The transgenes may be readily selected by one of skill in the art based on the desired result.

In another embodiment, the transgene is selected for use in gene correction therapy. This may be accomplished using, e.g., a zinc-finger nuclease (ZFN)-induced DNA double-strand break in conjunction with an exogenous DNA donor substrate. See, e.g., Ellis et al, Gene Therapy (epub January 2012) 20:35-42 which is incorporated herein by reference. The transgenes may be readily selected by one of skill in the art based on the desired result.

In one embodiment, the capsids described herein are useful in the CRISPR-Cas dual vector system described in U.S. Provisional Patent Application Nos. 61/153,470, 62/183,825, 62/254,225 and 62/287,511, each of which is incorporated herein by reference. The capsids are also useful for delivery homing endonucleases or other meganucleases.

In another embodiment, the transgenes useful herein include reporter sequences, which upon expression produce a detectable signal. Such reporter sequences include, without limitation, DNA sequences encoding β-lactamase, β-galactosidase (LacZ), alkaline phosphatase, thymidine kinase, green fluorescent protein (GFP), red fluorescent protein (RFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

Desirably, the transgene encodes a product which is useful in biology and medicine, such as proteins, peptides, RNA, enzymes, or catalytic RNAs. Desirable RNA molecules include shRNA, tRNA, dsRNA, ribosomal RNA, catalytic RNAs, and antisense RNAs. One example of a useful RNA sequence is a sequence which extinguishes expression of a targeted nucleic acid sequence in the treated animal.

The regulatory sequences include conventional control elements which are operably linked to the transgene in a manner which permits its transcription, translation and/or expression in a cell transfected with the vector or infected with the virus produced as described herein. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized.

The regulatory sequences useful in the constructs provided herein may also contain an intron, desirably located between the promoter/enhancer sequence and the gene. One desirable intron sequence is derived from SV-40, and is a 100 bp mini-intron splice donor/splice acceptor referred to as SD-SA. Another suitable sequence includes the woodchuck hepatitis virus post-transcriptional element. (See, e.g., L. Wang and I. Verma, 1999 Proc. Natl. Acad. Sci., USA, 96:3906-3910). PolyA signals may be derived from many suitable species, including, without limitation SV-40, human and bovine.

Another regulatory component of the rAAV useful in the methods described herein is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector.

In one embodiment, the AAV comprises a promoter (or a functional fragment of a promoter). The selection of the promoter to be employed in the rAAV may be made from among a wide number of constitutive or inducible promoters that can express the selected transgene in the desired target cell. In one embodiment, the target cell is an ocular cell. The promoter may be derived from any species, including human. Desirably, in one embodiment, the promoter is "cell specific". The term "cell-specific" means that the particular promoter selected for the recombinant vector can direct expression of the selected transgene in a particular cell tissue. In one embodiment, the promoter is specific for expression of the transgene in muscle cells. In another embodiment, the promoter is specific for expression in lung. In another embodiment, the promoter is specific for expression of the transgene in liver cells. In another embodiment, the promoter is specific for expression of the transgene in airway epithelium. In another embodiment, the promoter is specific for expression of the transgene in neurons. In another embodiment, the promoter is specific for expression of the transgene in heart.

The expression cassette typically contains a promoter sequence as part of the expression control sequences, e.g., located between the selected 5' ITR sequence and the immunoglobulin construct coding sequence. In one embodiment, expression in liver is desirable. Thus, in one embodiment, a liver-specific promoter is used. Tissue specific promoters, constitutive promoters, regulatable promoters [see, e.g., WO 2011/126808 and WO 2013/04943], or a promoter responsive to physiologic cues may be used may be utilized in the vectors described herein. In another embodiment, expression in muscle is desirable. Thus, in one embodiment, a muscle-specific promoter is used. In one embodiment, the promoter is an MCK based promoter, such as the dMCK (509-bp) or tMCK (720-bp) promoters (see, e.g., Wang et al, Gene Ther. 2008 November; 15(22): 1489-99. doi: 10.1038/gt.2008.104. Epub 2008 Jun. 19, which is incorporated herein by reference). Another useful promoter is the SPc5-12 promoter (see Rasowo et al, European Scientific Journal June 2014 edition vol. 10, No. 18, which is incorporated herein by reference). In one embodiment, the promoter is a CMV promoter. In another embodiment, the promoter is a TBG promoter. In another embodiment, a CB7 promoter is used. CB7 is a chicken β-actin promoter with cytomegalovirus enhancer elements. Alternatively, other liver-specific promoters may be used [see, e.g., The Liver Specific Gene Promoter Database, Cold Spring Harbor, rulai.schl.edu/LSPD, alpha 1 anti-trypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt)25(requires intron-less scAAV).

The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter.

The expression cassette may contain at least one enhancer, i.e., CMV enhancer. Still other enhancer elements may include, e.g., an apolipoprotein enhancer, a zebrafish enhancer, a GFAP enhancer element, and brain specific enhancers such as described in WO 2013/1555222, woodchuck post hepatitis post-transcriptional regulatory element. Additionally, or alternatively, other, e.g., the hybrid human cytomegalovirus (HCMV)-immediate early (IE)-PDGR promoter or other promoter-enhancer elements may be selected. Other enhancer sequences useful herein include the IRBP enhancer (Nicoud 2007, J Gene Med. 2007 December; 9(12):1015-23), immediate early cytomegalovirus enhancer, one derived from an immunoglobulin gene or SV40 enhancer, the cis-acting element identified in the mouse proximal promoter, etc.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A variety of suitable polyA are known. In one example, the polyA is rabbit beta globin, such as the 127 bp rabbit beta-globin polyadenylation signal (GenBank #V00882.1). In other embodiments, an SV40 polyA signal is selected. Still other suitable polyA sequences may be selected. In certain embodiments, an intron is included. One suitable intron is a chicken beta-actin intron. In one embodiment, the intron is 875 bp (GenBank #X00182.1). In another embodiment, a chimeric intron available from Promega is used. However, other suitable introns may be selected. In one embodiment, spacers are included such that the vector genome is approximately the same size as the native AAV vector genome (e.g., between 4.1 and 5.2 kb). In one embodiment, spacers are included such that the vector genome is approximately 4.7 kb. See, Wu et al, Effect of Genome Size on AAV Vector Packaging, Mol Ther. 2010 January; 18(1): 80-86, which is incorporated herein by reference.

Selection of these and other common vector and regulatory elements are conventional and many such sequences are available. See, e.g., Sambrook et al, and references cited therein at, for example, pages 3.18-3.26 and 16.17-16.27 and Ausubel et al., Current Protocols in Molecular Biology, John Wiley & Sons, New York, 1989. Of course, not all vectors and expression control sequences will function equally well to express all of the transgenes as described herein. However, one of skill in the art may make a selection among these, and other, expression control sequences without departing from the scope of this invention.

In another embodiment, a method of generating a recombinant adeno-associated virus is provided. A suitable recombinant adeno-associated virus (AAV) is generated by culturing a host cell which contains a nucleic acid sequence encoding an AAV capsid protein as described herein, or fragment thereof, a functional rep gene; a minigene composed of, at a minimum, AAV inverted terminal repeats (ITRs) and a heterologous nucleic acid sequence encoding a desirable transgene; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Also provided herein are host cells transfected with an AAV as described herein. Most suitably, such a stable host cell will contain the required component(s) under the control of an inducible promoter. However, the required component(s) may be under the control of a constitutive promoter. Examples of suitable inducible and constitutive promoters are provided herein, in the discussion below of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art. In another embodiment, the host cell comprises a nucleic acid molecule as described herein.

The minigene, rep sequences, cap sequences, and helper functions required for producing the rAAV described herein may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 *J. Virol.,* 70:520-532 and U.S.

Pat. No. 5,478,745, among others. These publications are incorporated by reference herein.

Also provided herein, are plasmids for use in producing the vectors described herein. Such plasmids are described in the Examples section.

C. PHARMACEUTICAL COMPOSITIONS AND ADMINISTRATION

In one embodiment, the recombinant AAV containing the desired transgene and cell-specific promoter for use in the target cells as detailed above is optionally assessed for contamination by conventional methods and then formulated into a pharmaceutical composition intended for administration to a subject in need thereof. Such formulation involves the use of a pharmaceutically and/or physiologically acceptable vehicle or carrier, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20. In another embodiment, the pharmaceutically acceptable carrier comprises a surfactant, such as perfluorooctane (Perfluoron liquid). The vector is formulated in a buffer/carrier suitable for infusion in human subjects. The buffer/carrier should include a component that prevents the rAAV from sticking to the infusion tubing but does not interfere with the rAAV binding activity in vivo.

In certain embodiments of the methods described herein, the pharmaceutical composition described above is administered to the subject intramuscularly. In other embodiments, the pharmaceutical composition is administered by intravenously. Other forms of administration that may be useful in the methods described herein include, but are not limited to, direct delivery to a desired organ (e.g., the eye), including subretinal or intravitreal delivery, oral, inhalation, intranasal, intratracheal, intravenous, intramuscular, subcutaneous, intradermal, and other parental routes of administration. Routes of administration may be combined, if desired.

Furthermore, in certain embodiments it is desirable to perform certain examinations prior to vector administration to identify areas requiring cells to be targeted for therapy. In one embodiment, where delivery to the eye is desired, non-invasive retinal imaging and functional studies to identify areas of specific ocular cells to be targeted for therapy. See, e.g., WO 2014/124282, which is incorporated herein by reference. See also, International Patent Application No. PCT/US2013/022628 which is incorporated herein by reference.

The composition may be delivered in a volume of from about 0.1 μL to about 10 mL, including all numbers within the range, depending on the size of the area to be treated, the viral titer used, the route of administration, and the desired effect of the method. In one embodiment, the volume is about 50 μL. In another embodiment, the volume is about 70 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 250 μL. In another embodiment, the volume is about 300 μL. In another embodiment, the volume is about 450 μL. In another embodiment, the volume is about 500 μL. In another embodiment, the volume is about 600 μL. In another embodiment, the volume is about 750 μL. In another embodiment, the volume is about 850 μL. In another embodiment, the volume is about 1000 μL. In another embodiment, the volume is about 1.5 mL. In another embodiment, the volume is about 2 mL. In another embodiment, the volume is about 2.5 mL. In another embodiment, the volume is about 3 mL. In another embodiment, the volume is about 3.5 mL. In another embodiment, the volume is about 4 mL. In another embodiment, the volume is about 5 mL. In another embodiment, the volume is about 5.5 mL. In another embodiment, the volume is about 6 mL. In another embodiment, the volume is about 6.5 mL. In another embodiment, the volume is about 7 mL. In another embodiment, the volume is about 8 mL. In another embodiment, the volume is about 8.5 mL. In another embodiment, the volume is about 9 mL. In another embodiment, the volume is about 9.5 mL. In another embodiment, the volume is about 10 mL.

An effective concentration of a recombinant adeno-associated virus carrying a nucleic acid sequence encoding the desired transgene under the control of the regulatory sequences desirably ranges from about $10^7$ and $10^{14}$ vector genomes per milliliter (vg/mL) (also called genome copies/mL (GC/mL)). In one embodiment, the rAAV vector genomes are measured by real-time PCR In another embodiment, the rAAV vector genomes are measured by digital PCR See, Lock et al, Absolute determination of single-stranded and self-complementary adeno-associated viral vector genome titers by droplet digital PCR, Hum Gene Ther Methods. 2014 April; 25(2): 115-25. doi: 10.1089/hgtb.2013.131. Epub 2014 Feb. 14, which are incorporated herein by reference. In another embodiment, the rAAV infectious units are measured as described in S. K. McLaughlin et al, 1988 J. Virol., 62:1963, which is incorporated herein by reference.

Preferably, the concentration is from about $1.5\times10^9$ vg/mL to about $1.5\times10^{13}$ vg/mL, and more preferably from about $1.5\times10^9$ vg/mL to about $1.5\times10^{11}$ vg/mL. In one embodiment, the effective concentration is about $1.4\times10^8$ vg/mL. In one embodiment, the effective concentration is about $3.5\times10^{10}$ vg/mL. In another embodiment, the effective concentration is about $5.6\times10^{11}$ vg/mL. In another embodiment, the effective concentration is about $5.3\times10^{12}$ vg/mL. In yet another embodiment, the effective concentration is about $1.5\times10^{12}$ vg/mL. In another embodiment, the effective concentration is about $1.5\times10^{13}$ vg/mL. All ranges described herein are inclusive of the endpoints.

In one embodiment, the dosage is from about $1.5\times10^9$ vg/kg of body weight to about $1.5\times10^{13}$ vg/kg, and more preferably from about $1.5\times10^9$ vg/kg to about $1.5\times10^{11}$ vg/kg. In one embodiment, the dosage is about $1.4\times10^8$ vg/kg. In one embodiment, the dosage is about $3.5\times10^{10}$ vg/kg. In another embodiment, the dosage is about $5.6\times10^{11}$ vg/kg. In another embodiment, the dosage is about $5.3\times10^{12}$ vg/kg. In yet another embodiment, the dosage is about $1.5\times10^{12}$ vg/kg. In another embodiment, the dosage is about $1.5\times10^{13}$ vg/kg. In another embodiment, the dosage is about $3.0\times10^{13}$ vg/kg. In another embodiment, the dosage is about $1.0\times10^{14}$ vg/kg. All ranges described herein are inclusive of the endpoints.

In one embodiment, the effective dosage (total genome copies delivered) is from about $10^7$ to $10^{13}$ vector genomes. In one embodiment, the total dosage is about $10^8$ genome copies. In one embodiment, the total dosage is about $10^9$ genome copies. In one embodiment, the total dosage is about $10^{10}$ genome copies. In one embodiment, the total dosage is about $10^{11}$ genome copies. In one embodiment, the total dosage is about $10^{12}$ genome copies. In one embodiment, the total dosage is about $10^{13}$ genome copies. In one embodiment, the total dosage is about $10^{14}$ genome copies. In one embodiment, the total dosage is about $10^{15}$ genome copies.

It is desirable that the lowest effective concentration of virus be utilized in order to reduce the risk of undesirable effects, such as toxicity. Still other dosages and administration volumes in these ranges may be selected by the attending physician, taking into account the physical state of the subject, preferably human, being treated, the age of the subject, the particular disorder and the degree to which the disorder, if progressive, has developed. Intravenous delivery, for example may require doses on the order of $1.5\times10^{13}$ vg/kg.

D. METHODS

As discussed herein, the vectors comprising the AAV8 mutant capsids are capable of transducing target tissues at high levels. Thus, provided herein is a method of delivering a transgene to a liver cell. The method includes contacting the cell with an rAAV having the AAV3G1 capsid, wherein said rAAV comprises the transgene. In another embodiment, the method includes contacting the cell with an rAAV having the AAV8.TR1 capsid, wherein said rAAV comprises the transgene. In another embodiment, the method includes contacting the cell with an rAAV having any capsid described herein, wherein the rAAV comprises the transgene. In another aspect, the use of an rAAV having the AAV3G1 capsid is provided for delivering a transgene to liver. In another aspect, the use of an rAAV having the AAV8.TR1 capsid is provided for delivering a transgene to liver.

Also provided herein is a method of delivering a transgene to a muscle cell. The method includes contacting the cell with an rAAV having the AAV3G1 capsid, wherein said rAAV comprises the transgene. In another embodiment, the method includes contacting the cell with an rAAV having any capsid described herein, wherein the rAAV comprises the transgene. In another aspect, the use of an rAAV having the AAV3G1 capsid is provided for delivering a transgene to muscle.

Further, a method of delivering a transgene to the airway epithelium is provided. The method includes contacting the cell with an rAAV having the AAV3G1 capsid, wherein said rAAV comprises the transgene. In another embodiment, the method includes contacting the cell with an rAAV having the AAV8.T20 capsid, wherein said rAAV comprises the transgene. In another embodiment, the method includes contacting the cell with an rAAV having any capsid described herein, wherein the rAAV comprises the transgene. In another aspect, the use of an rAAV having the AAV3G1 capsid is provided for delivering a transgene to airway epithelium. In another aspect, the use of an rAAV having the AAV8.T20 capsid is provided for delivering a transgene to airway epithelium.

Further, a method of delivering a transgene to ocular cells is provided. The method includes contacting the cell with an rAAV having the AAV3G1 capsid, wherein said rAAV comprises the transgene. In another embodiment, the method includes contacting the cell with an rAAV having any capsid described herein, wherein the rAAV comprises the transgene. In another aspect, the use of an rAAV having the AAV3G1 capsid is provided for delivering a transgene to ocular cells.

As described in the examples below, in vitro, the AAV3G1 mutant showed resistance to various antisera of monkey and human, as well as human IVIG (at levels 2 to 4 fold that of AAV8, with respect to human IVIG). All three mutations contributed to the observed resistance. In mice, the liver transduction efficiency of AAV3G1 was reduced compared with AAV8, however its muscle transduction was higher than that of AAV8 by approximately 10 fold. In addition, AAV3G1 demonstrated a higher heparin affinity than AAV8. Interestingly, reducing the positive charges of the HVRIV mutation decreased the vector's heparin affinity while liver transduction was partially restored. Similar to the trend observed in muscle, intranasal administration of AAV3G1 resulted in a transduction efficiency 2 to 3 fold greater than that of AAV8, which was further improved to levels approximately 10 fold greater than AAV8 by swapping the VP1 unique region of AAV3G1 with that of another AAV serotype. These findings are relevant to disease models where high-efficiency intramuscular, ocular or intranasal gene delivery and resistance to pre-existing neutralizing antibodies are desired.

As shown herein, the capsid described herein (e.g., the AAV3G1, AAVT20 or AAVTR1 capsid) is, in one embodiment, able to evade neutralization by pre-existing neutralizing antibodies (NAbs) to AAV8. In one embodiment, the rAAV having the capsid described shows at least about a 2 fold increase in resistance to neutralization by an AAV8 neutralizing antibody as compared to native AAV8. In one embodiment, the rAAV having the capsid described shows at least about a 3 fold increase in resistance to neutralization by an AAV8 neutralizing antibody as compared to native AAV8. In one embodiment, the rAAV having the capsid described shows at least about a 4 fold increase in resistance to neutralization by an AAV8 neutralizing antibody as compared to native AAV8. In one embodiment, the rAAV having the capsid described shows at least about a 5 fold increase in resistance to neutralization by an AAV8 neutralizing antibody as compared to native AAV8. In one embodiment, the rAAV having the capsid described shows at least about a 10 fold increase in resistance to neutralization by an AAV8 neutralizing antibody as compared to native AAV8. In one embodiment, the rAAV having the capsid described shows at least about a 15, 20, 25, 30, 35, 40, 45, 50, 55, 60, 65, 70, 75, 80, 85, 90, 95, 100, 200, 220, 240, 260 or greater fold increase in resistance to neutralization by an AAV8 neutralizing antibody as compared to native AAV8. Methods of assessing antibody neutralization are known in the art and described herein. See, e.g., Lochrie et al, J Virol., January 2006, 80(2):821-34, which is incorporated herein by reference. In one embodiment, the AAV8 neutralizing antibody is ADK8. See, Gurda et al, J. Virol, 2012 August; 86(15):7739-51. doi: 10.1128/JVI.00218-12. Epub 2012 May 16, which is incorporated herein by reference. In another embodiment, the AAV8 neutralizing antibody is ADK8/9.

This reduction in neutralization by an AAV8 antibody provides the advantage of escaping pre-existing AAV8 antibodies which may be present in the subject. This is useful in instances where an AAV8 vector was used in treating the subject for a certain condition, and a booster dosage is required or second treatment requiring use of an AAV vector.

Saturation mutagenesis was performed on the AAV8 hyper-variable region (HVR) VIII guided by antibody-capsid structure information. It was demonstrated that the capsid mutants were capable of escaping AAV8 neutralizing antibodies and maintained liver transduction.

Saturation mutagenesis was performed on HVR.I and HVR.IV regions, beginning with one of the capsid mutants described above—AAV8.C41—as the backbone, followed by three rounds of in vivo enrichment in mouse liver, resulting in an AAV8 mutant, termed AAV3G1 (also called AAV8.Triple or Triple). AAV3G1 showed resistance to various antisera of monkey and human, as well as human IVIG (at levels 2 to 4 fold that of AAV8, with respect to human IVIG). All the three mutations contributed to the observed resistance. Unexpectedly, AAV83G1 demonstrated decreased liver transduction efficiency of as compared to AAV8 native (~1/6×AAV8) while its muscle transduction was increased (~10×AAV8). AAV3G1 demonstrated a higher heparin affinity than AAV8. Reducing the positive charges of the HVR.IV and HVR.I mutation decreased the vector's heparin affinity accompanied by partially restored liver transduction (the resulting mutant is called AAV8.TR1). Intranasal administration of AAV3G resulted in a transduction efficiency 2 to 3 fold greater than that of AAV8. A new mutant, AAV8.T20, was created by swapping the VP1/2-unique region of one of the high transduction members, rh. 20, into AAV3G1, resulting in AAV8.T20. I.e., amino acids 1-202 of AAVrh.20 (SEQ ID NO: 88) were swapped in for amino acids 1 to 203 of the AAV3G1 capsid. AAV8.T20's transduction was approximately 10 fold greater than AAV8 in mice by intranasal administration.

E. EXAMPLES

Example 1: Study Design

Several AAV8 mutants were generated c41, c42, c46, g110, g113, g115 and g8117 with mutations in the HVR.VIII region. As discussed in Gurda et al, cited above, the major ADK8 epitope lies in the HVR.VIII region (amino acids 586 to 591 using AAV8 vp1 numbering). Those mutants were tested in vitro for ADK8 resistance and some of them were tested in vivo for ADK8 resistance. See, e.g., Lochrie 2006 cited above.

| Name | Amino acid sequence (583-597) |
|---|---|
| AAV8 | ADNLQQQNTAPQIGT; SEQ ID NO: 69 |
| C41 | GDNLQLYNTAPGSVF; SEQ ID NO: 70 |
| C42 | SDNLQFRNTAPLWSS; SEQ ID NO: 71 |
| C46 | NDNLQVCNTAPDDVM; SEQ ID NO: 72 |
| G110 | CDNLQGYNTAPLCVA; SEQ ID NO: 73 |
| G112 | VDNLQFLNTAPAGEA; SEQ ID NO: 74 |
| G113 | LDNLQDGNTAPGACG; SEQ ID NO: 75 |
| G115 | WDNLQSENTAPSETS; SEQ ID NO: 76 |
| G117 | SDNLQSCNTAPFAGA; SEQ ID NO: 77 |

The mutant c41 was picked as the backbone for further mutagenesis at HVR.I and HVR.IV region. Mutant c41 has the sequence shown in SEQ ID NO: 2 (DNA sequence shown in SEQ ID NO: 1). The c41 amino acid sequence is that of AAV8, with the following mutation in the HVR.VIII region: 583ADNLQQQNTAPQIGT597 (SEQ ID NO: 69)→GDNLQLYNTAPGSVF (SEQ ID NO: 70).

For HVR.I or HVR.IV mutagenesis, three rounds of in vivo selection were done. HVR.I mutation SGTH and HVR.IV mutation GGSRP were then incorporated into clone c41 backbone to generate AAV3G1. In vitro Nab tests show that AAV3G1 showed some degree of hIVIG resistance; all the three mutations (c41, SGTH and GGSRP) contribute to the resistance.

AAV3G1 shows a higher muscle transduction than AAV8, both i.m. and i.v., with various transgene cassettes such as CB7.CI.ffluciferase, CMV.LacZ and tMCK.human F9.

AAV3G1 also shows higher transduction in murine airway epithelia cells than AAV8. By replacing the VP1/2 region with that of rh.20, the resulting mutant, AAV8.T20, shows transduction, ~10 times of AAV8. In nasal administration to B6 mice, normalized to AAV8 (100%, CB7.CI.luciferase), AAV3G1 transduced at 375% while AAV8.T20 transduced at 988%.

AAV3G1 has heparin affinity higher than AAV8. A new mutant was designed to introduce negative-charged residues in HVR.I and HVR.IV (HVRI: SGTH→SDTH. HVRIV: GGSRP is replaced by another mutation, DGSGL (SEQ ID NO: 82), showed up during the selection process. The resulting mutant, AAV8.TR1, shows decreased heparin affinity and its liver transduction was partially restored. As compared to AAV8 (100%, TBG.human F9), AAV3G1 transduces liver at 18%, while AAV.TR1 transduces at 52%.

Example 2: Materials and Methods

A. Plasmids for Library Construction.

1. pAAV.DE.0

Figure 9:
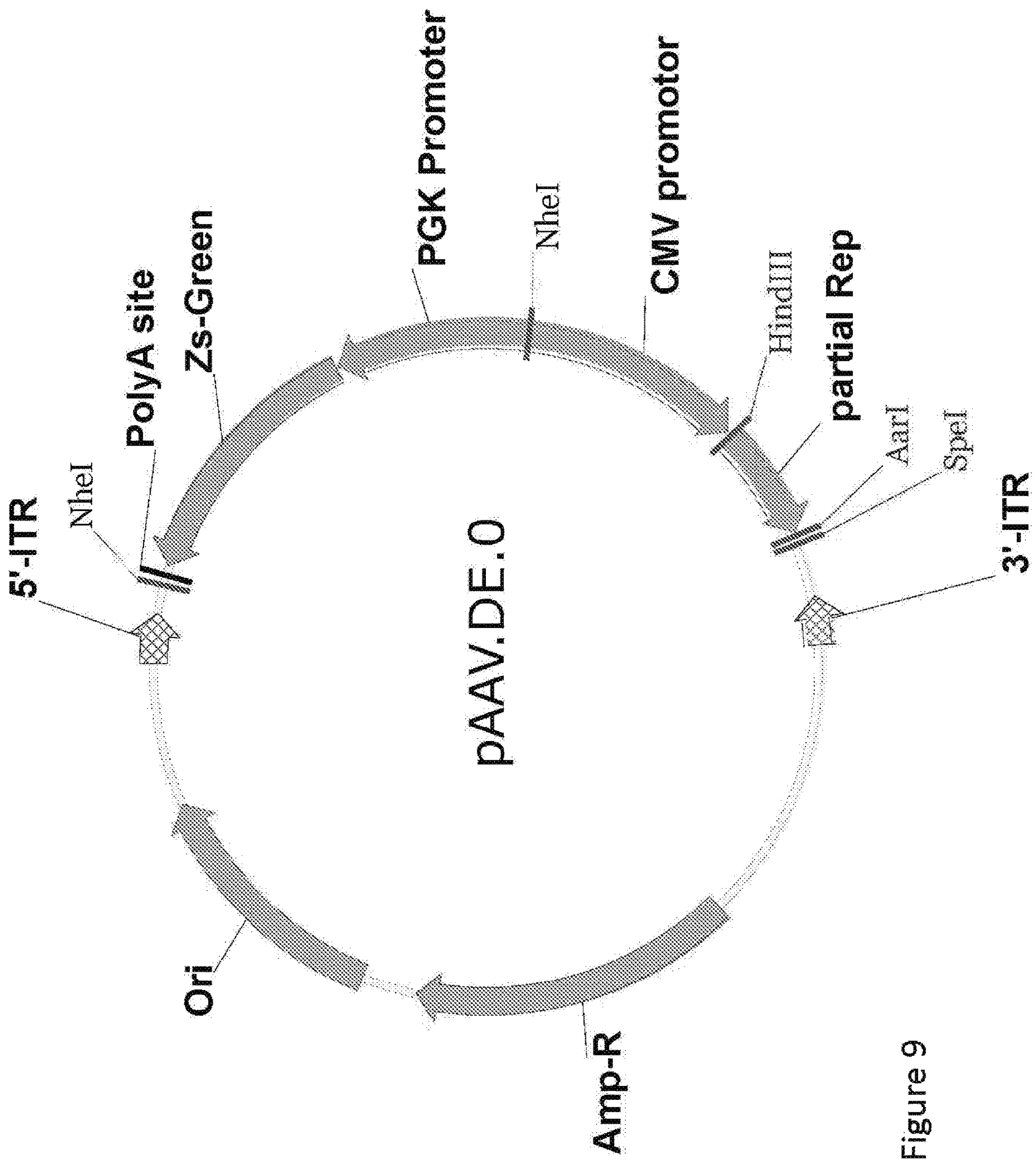
FIG. 9 provides a map of pAAV.DE.0.

The plasmid pAAV.DE.0 was constructed by placing the following components between the two AAV ITRs—ZsGreen expression cassette, followed by CMV promoter, followed by fragment 1883-2207 of AAV2 genome (NC_001401), followed by restriction sites AarI and SpeI (for inserting AAV VP1 ORF). pAAV.DE.0 is shown in SEQ ID NO: 39 and FIG. 9.

2. pAAV.DE.1

Figure 10:
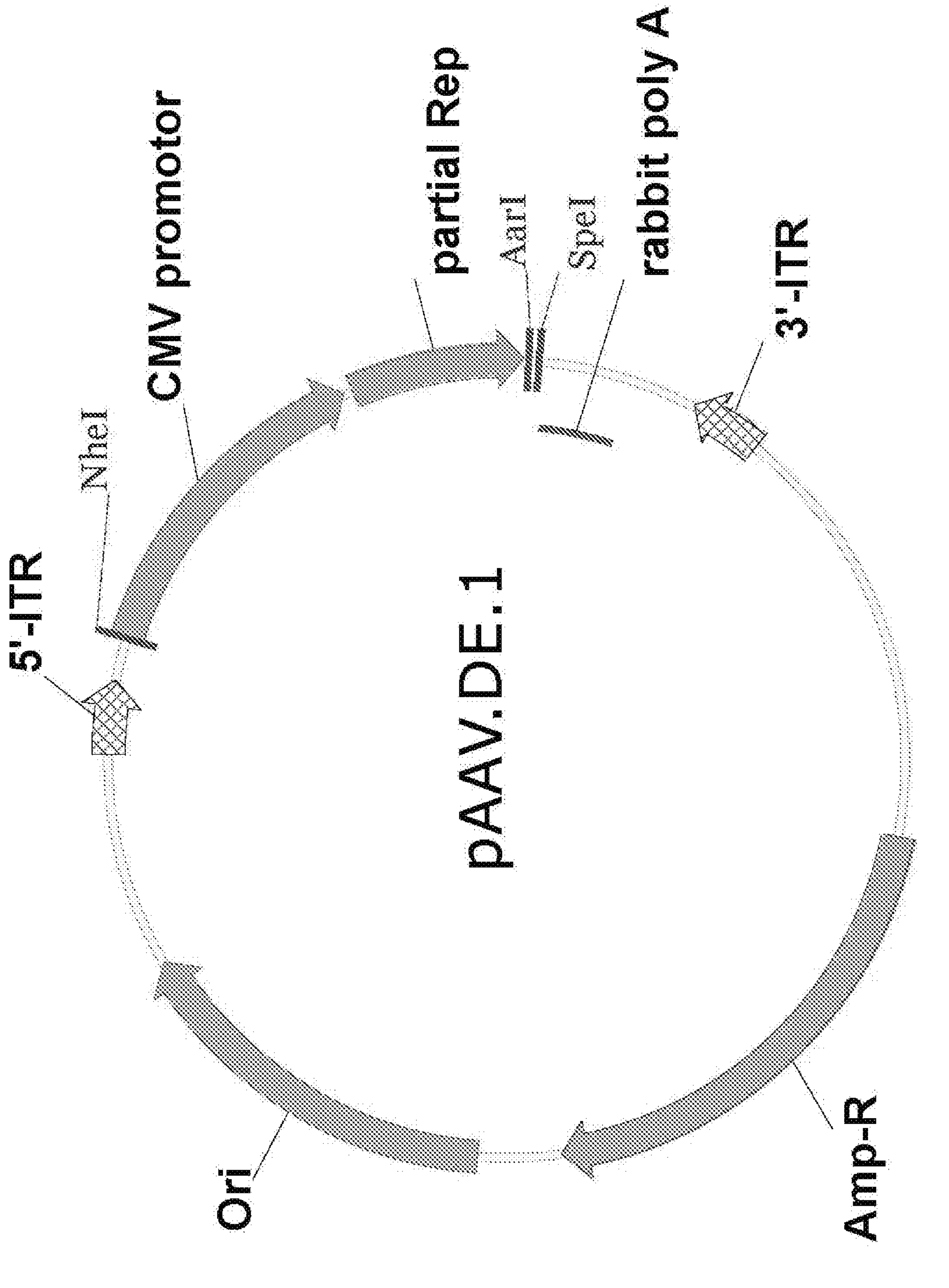
FIG. 10 provides a map of pAAV.DE.1.

The plasmid pAAV.DE.1 was based on pAAV.DE.0 with modifications: 1) the NheI fragment was removed; 2) a rabbit beta-globin polyadenylation signal sequence was inserted between the 3' ITR and the SpeI restriction recognition site. pAAV.DE.1 is shown in SEQ ID NO: 40 and FIG. 10.

3. pAAV.DE.1.HVR.I

Figure 11:
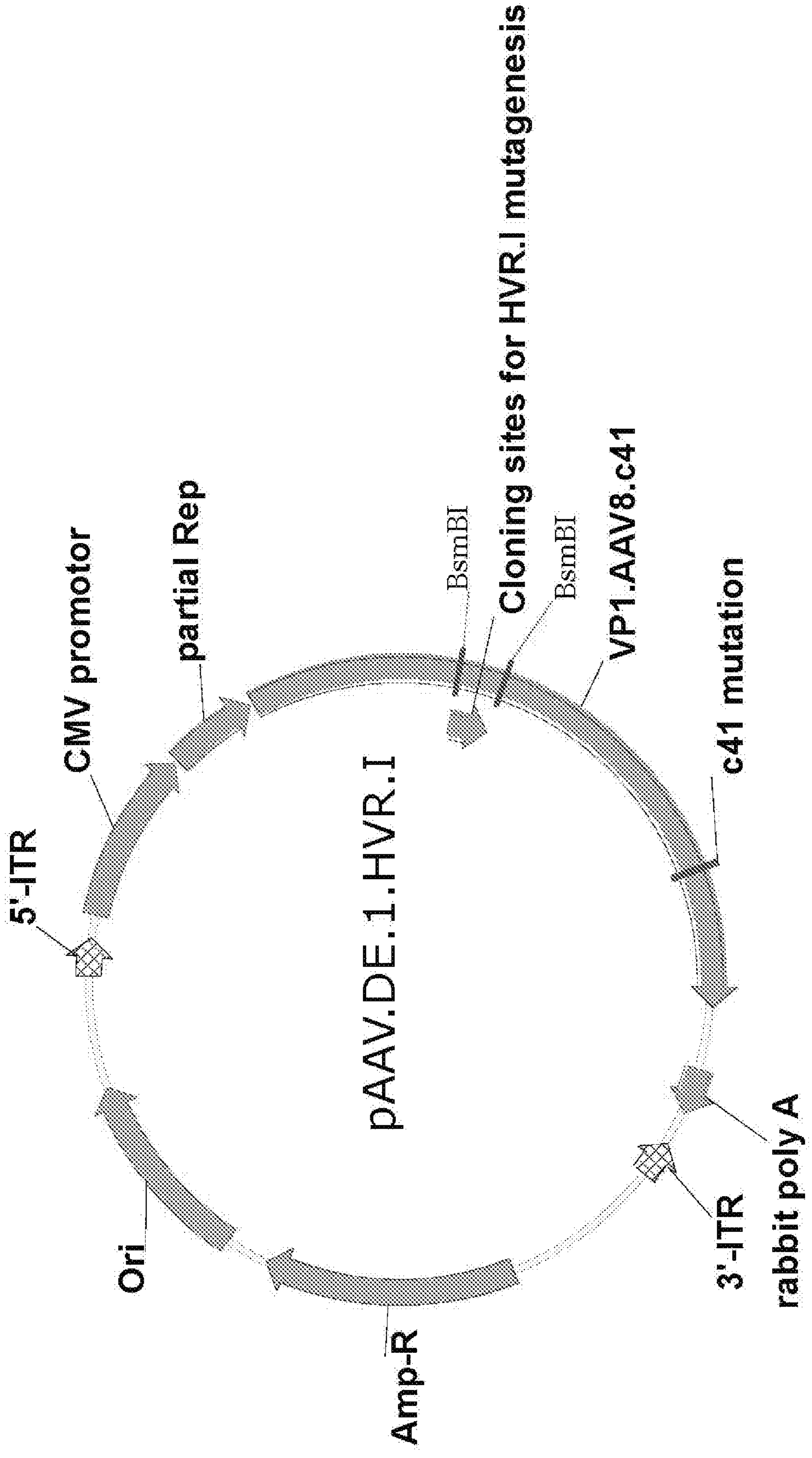
FIG. 11 provides a map of pAAV.DE.1.HVRI.

The plasmid was based on pAAV.DE.1 with 1) the VP1 ORF of AAV8.c41 was inserted in pAAV.DE.1 between AarI and SpeI; 2) the two BsmBI restriction recognition sites were removed by silent mutagenesis; 3) a small DNA fragment carrying two BsmBI sites at its ends was inserted at HVR.I region of AAV8.c41 VP1 ORF to create a cloning site for HVR.I 30 mutagenesis. pAAV.DE.1.HVR.I is shown in SEQ ID NO: 41 and FIG. 11.

4. pAAV.DE.1.HVR.IV

Figure 12:
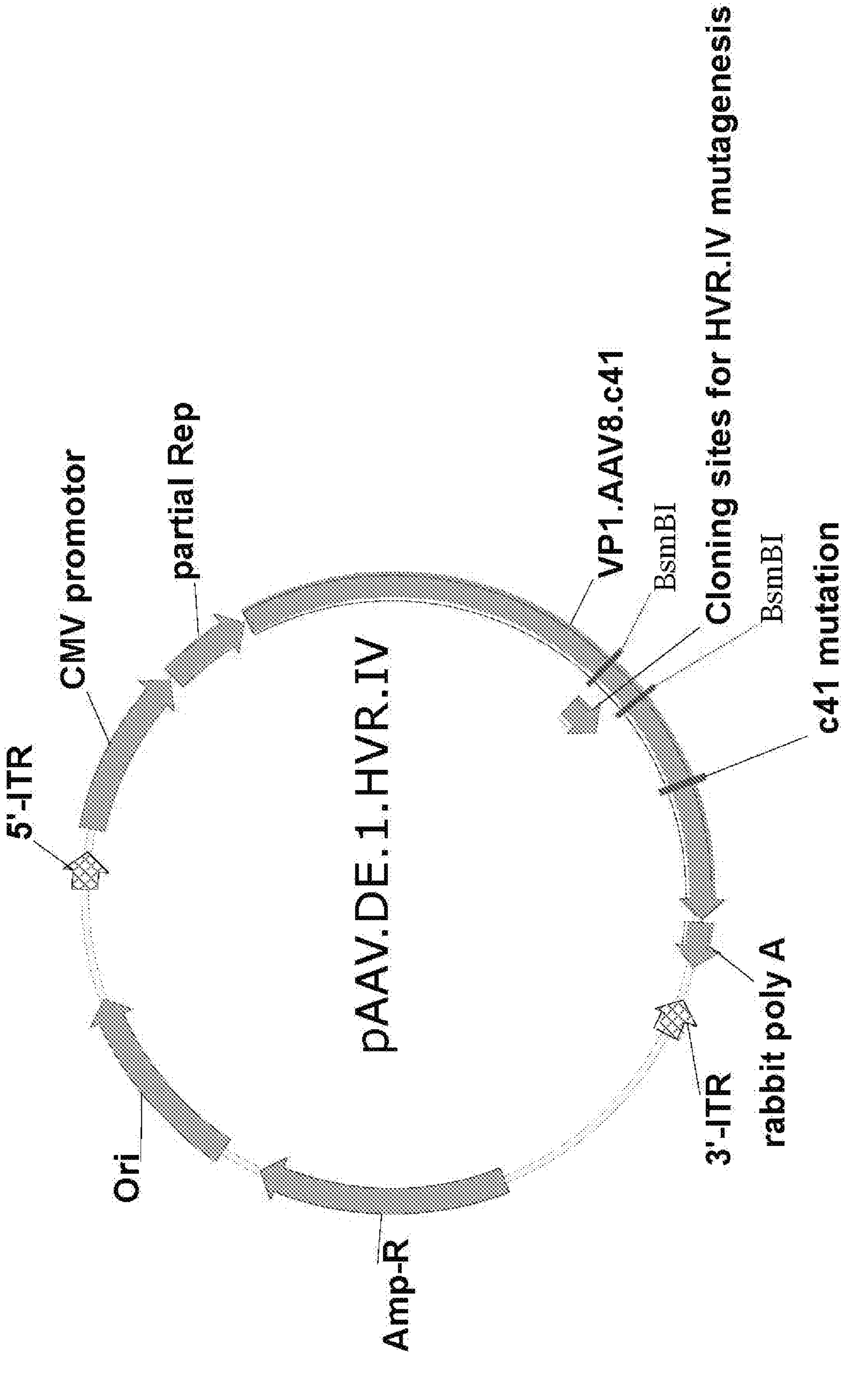
FIG. 12 provides a map of pAAV.DE.1.HVRIV.

The plasmid was based on pAAV.DE.1 with 1) the VP1 ORF of AAV8.c41 was inserted in pAAV.DE.1 between AarI and SpeI: 2) the two BsmBI restriction recognition sites were removed by silent mutagenesis; 3) a small DNA fragment carrying two BsmBI sites at its ends was inserted at HVRIV region of AAV8.c41 VP1 ORF to create a cloning site for HVRIV mutagenesis. pAAV.DE.1.HVRIV is shown in SEQ ID NO: 42 and FIG. 12.

5. pRep

The plasmid was based on pAAV2/8 plasmid (SEQ ID NO: 43). The plasmid pAAV2/8 was digested with AfeI, then partially digested with BbsI, end-polishing and then self-ligated.

B. Library Construction, Selection and the Generation of AAV3G1, AAV8.T20 and AAV8.TR1.

1. HVR.VIII Library

Three PCRs were set up: PCR1: primer031(SEQ ID NO: 49), primer032 (SEQ ID NO: 50) and primer009 (SEQ ID NO: 45); PCR2: primer016 (SEQ ID NO: 46) and primer030 (SEQ ID NO: 48), with the plasmid pAAV2/8 as template; PCR3: primer033 (SEQ ID NO: 49) and primer017 (SEQ ID NO: 47), with the plasmid pAAV2/8 as template. Primers shown in Table 2 below. The three PCR products were purified QIAquick PCR purification Kit (Qiagen), combined together, digested with BsmBI (New England Biolabs) and purified again, followed by ligation at 16° C. with T4 DNA ligase (Roche). A 428-bp fragment was gel-extracted and ligated with the 6908-bp BsmBI fragment of pAAV2/8. The ligation product served as PCR template with primer.AAV8start and primer AAV8 END nd5R The PCR product was purified, cloned into pAAV.DE.0 through AarI and SpeI and transformed into Stbl4 (Invitrogen). Plasmid was extracted from the overnight culture of the transformation and it was the plasmid library of AAV8 HVRVIII mutagenesis.

The plasmid library was mixed with helper plasmid (pAdΔF6) and pRep, and then transfected into 293 cells by Calcium-phosphate method. Three days after transfection, cell lysate was harvest, re-suspended in DPBS and treated with Benzonase (Merck). The lysate was then spun down to remove debris. The supernatant was the AAV mutagenesis library and stored at −20° C. for further uses. The titration was done with real-time PCR $1\times10^9$ genome copies (gc) of the AAV mutagenesis library was mixed with 0.5 μL of ADK8 (AAV8 Nab titer—1:2560) and added up to 1 mL with complete medium. The mixture was incubated at 37° C. for 30 min, and then applied to the 293 cells (MOI, $\sim1\times10^4$). Two days later, the cell was split at a ratio of 1:5. Two days later, the cells were transfected with the plasmid pAdΔF6 and pRep. Two days later, RNA and genomic DNA were extracted from the cells as templates for RT-PCR or PCR The PCR primers were primer016 (SEQ ID NO: 46) and primer017 (SEQ ID NO: 47). The PCR product was cloned into Topo vector (Invitrogen) and sequenced. AAV fragments were cut out from the Topo plasmids and cloned into pAAV2/8 at the BsmBI sites to make trans plasmids. Individual trans plasmids were packed into regular AAV vectors with pAAV.CMV.eGFP as the cis-plasmid for further analysis.

TABLE 2

Primer list:

| Name | Sequence | Seq ID |
|---|---|---|
| primer009 | ctacagaggaatacggtatcgtgnnkgataacttgcagnnknnkaacacggctcctnnknnknnknnkgtcaacagccaggggccttac | 45 |
| primer016 | Tggaccggctgatgaatcct | 46 |
| primer017 | Cggtgctgtattgcgtgatg | 47 |
| primer030 | ggctcacgtctctgtagccacagggttagtggtt | 48 |

TABLE 2-continued

Primer list:

| Name | Sequence | Seq ID |
|---|---|---|
| primer031 | cggacacgtctcgctacagaggaatacggtatcgtg | 49 |
| primer032 | ggctcacgtctcggtaaggccccctggctg | 50 |
| primer033 | cggacacgtctccttacccggtatggtctggcagaa | 51 |
| primer035 | Cacgcagaatgaaggcacca | 52 |
| primer042 | Cacgataccgtattcctctgtagccac | 53 |
| primer084 | gctggtttagtgaaccgtcagatcctgcat | 54 |
| primer098 | Aaggtgcgcgtggaccagaa | 55 |
| primer113 | Acaggtactggtcaatcagagg | 56 |
| primer155 | caaccacctctacaagcaaatctccnnknnknnknnknnkggagccaccaacgacaacacctact | 57 |
| primer156 | agtaggtgttgtcgttggtggctccmnnmnnmnnmnnmnnggagatttgcttgtagaggtggttg | 58 |
| primer157 | ctacttgtctcggactcaaacaacannknnknnknnknnkacgcagactctgggcttcagccaa | 59 |
| primer158 | ttggctgaagcccagagtctgcgtmnnmnnmnnmnnmnntgtgtttgagtccgagacaagtag | 60 |
| primer159 | gatttttggcaaacaaaatgctgccnnknnknnknnknnktacagcgatgtcatgctcaccagcg | 61 |
| primer160 | cgctggtgagcatgacatcgctgtamnnmnnmnnmnnmnnggcagcattttgtttgccaaaaatc | 62 |
| primer175 | cggtcacgtctcggtcatcaccaccagcacccgaac | 63 |
| primer200 | gccagtcgtctccgttgtcgttggtggctcc | 64 |
| primer201 | cggtcacgtctcgcctctgattgaccagtacctgtactacttgtctcggactcaa | 65 |
| primer202 | gccagtcgtctccgccattgtattaggcccaccttggctgaagcccagagtc | 66 |
| primer.AAV8start | ttaccccacaggaagcacgccacctgcaaatcaggtatggctgccgatggttatcttc | 67 |
| primer.AAV8end | ctcgttctctgccgtgtgggactagttacagattacgggtgaggtaacgggtgcca | 68 |

Figure 2A:
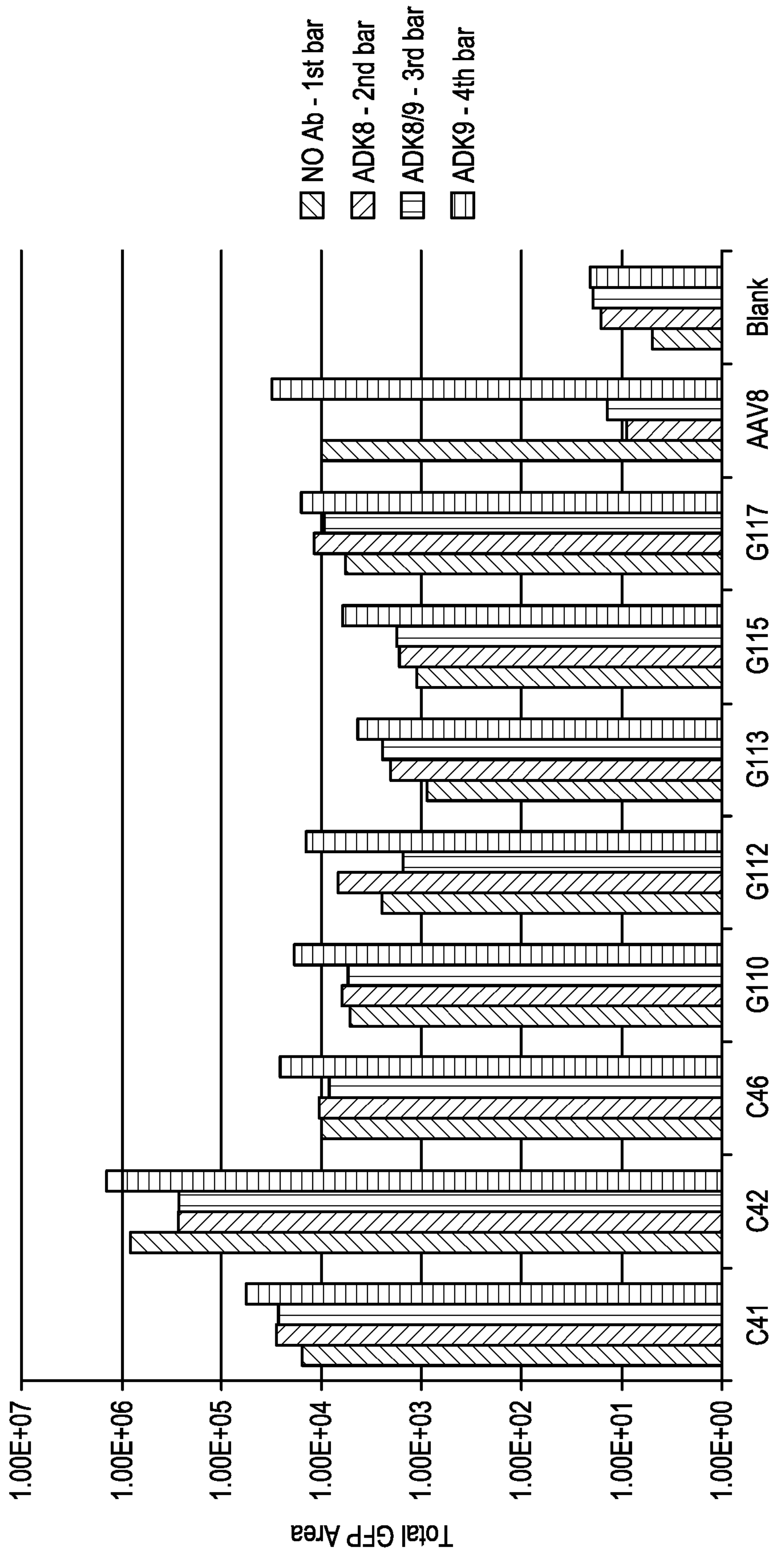
FIG. 2A is a bar graph demonstrating that mutagenesis at the antibody-capsid contact sites confers Nab resistance in vitro. The HEK 293 cells were infected by AAV8 and mutants carrying CMV.eGFP, mixed with medium (No Ab), antibody ADK8, ADK8/9 or ADK9. The M.O.I. was around 1e4. Two days later, GFP images were taken and analyzed. See Example 2B2.

2. In Vitro Nab Assay $1\times10^9$ gc of each AAV mutant carrying eGFP cassette was mixed with different monoclonal antibodies (ADK8, [Nab] AAV8=1:2560, 0.5 μL/well; ADK8/9, [Nab]AAV8=1:2560, 0.5 μL/well; ADK9, [Nab]AAV8=5, 0.5 μL/well; No Ab: medium), up to 100 μL with media, incubated at 37° C. for 30 minutes and then applied to 293 cells ($5\times10^4$ cells/well seeded one day before infection in a 96-well plate). GFP expression was monitored and quantified with Image J. FIG. 2*a*.

3. HVR.I and HVR.IV Libraries

Three rounds of selection were performed in vivo. For each round, the AAV libraries were injected into B6 mice, i.v., in the presence of pooled human IVIG (hIVIG).

For round 1, HVRI:

Two fragments were made through PCR with pAAV2/8.c41 as the template and primer098 (SEQ ID NO: 55)+primer156 (SEQ ID NO: 58), primer155 (SEQ ID NO: 57)+primer as the primer sets, respectively. The two fragments were assembled together by PCR with primer098 (SEQ ID NO: 55)+primer.AAV8end (SEQ ID NO: 68). The resulting fragments were then cloned into pAAV.DE.1 through HindII and SpeI sites as the plasmid libraries for the production of AAV libraries. The library production was similar to HVR.VIII library except that it was purified with iodixanol gradient, the same way as regular AAV vector.

For round 1, HVR.IV:

The process was very similar to HVR.I except that the primer sets were primer098 (SEQ ID NO: 55)+primer158 (SEQ ID NO: 60), primer157 (SEQ ID NO: 59)+primer.AAV8end (SEQ ID NO: 68).

The libraries were then injected into mice in the presence of human IVIG, i.v. Two weeks later, liver was harvested. Genomic DNA and RNA were extracted. AAV DNA fragments were retrieved through PCR and cloned into plasmids for new library production.

Round 2 and round 3 were similar to round 1, except that:

For HVRI, primer175 (SEQ ID NO: 63) and primer200 (SEQ ID NO: 64) were used and the cloning vector was pAAV.DE.1.HVRI; for HVRIV, primer201 (SEQ ID NO: 65) and primer202 (SEQ ID NO: 66) were used and the cloning vector was pAAV.DE.1.HVRIV.

After round 3, genomic DNA was extract from mouse liver, amplified through PCR and cloned into trans plasmid backbone for further analysis.

4. The Generation of AAV3G1, AAV8.T20 and AAV8.TR1

The trans plasmid pAAV2/8.Triple was based on pAAV2/8.c41 (SEQ ID NO: 44), in which the HVR.I region was replaced by DNA coding SGTH and the HVR.IV region was replaced by DNA coding GGSRP.

The trans plasmid pAAV2/8.T20 was based on pAAV2/8.Triple, in which the VP12 region was replaced with the corresponding region of AAVrh.20.

The trans plasmid pAAV2/8.TR was based on pAAV2/8.Triple, in which the HVR.I region was replaced by DNA coding SDTH (SEQ ID NO: 80) and the HVR.IV region was replaced by DNA coding DGSGL (SEQ ID NO: 82).

5. AAV Vector Production

AAV vectors were made according the method described by Lock, M, Alvira, M, Vandenberghe, L H, Samanta, A, Toelen, J, Debyser, Z, et al. (2010). Rapid, Simple, and Versatile Manufacturing of Recombinant Adeno-Associated Viral Vectors at Scale. Human Gene Therapy 21: 1259-1271.

6. ELSA for Canine F9 and Human F9

Figure 2B:
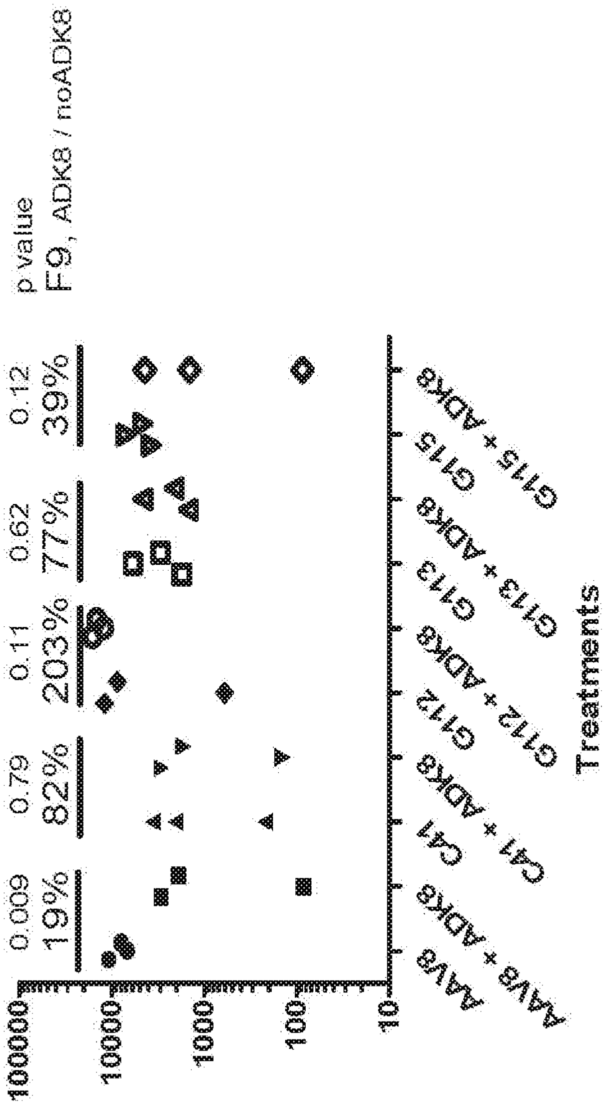
FIG. 2B is a scatter plot demonstrating mutagenesis at the antibody-capsid contact sites confers Nab resistance in vivo. AAV8 mutants were packed with TBG.canine F9-WPRE cassette and tested in B6 in the presence/absence of antibody ADK8 through i.v. injection. 100 uL of diluted ADK8 was injected i.v. 2 hours prior to vector injection. AAV8 was used as control. Canine F9 level was measured with ELISA from plasma collected 1 week after administration. The percent of F9 from ADK8-present animal to ADK8-absent animal and p value (t-test) are shown above. See Example 2B6.

The ELISA for measuring canine F9 was described by Wang, L L, Calcedo, R. Nichols, T C, Bellinger, D A, Dillow, A, Verma, I M, et al. (2005). Sustained correction of disease in naive and AAV2-pretreated hemophilia B dogs: AAV2/8-mediated, liver-directed gene therapy. Blood 105: 3079-3086 which is incorporated herein by reference. Briefly, AAV8 mutants were packed with TBG.canine F9-WPRE cassette and tested in B6 mice in the presence/absence of antibody ADK8 through i.v. injection. 100 uL of diluted ADK8 was injected i.v. 2 hours prior to vector injection. AAV8 was used as control. Canine F9 level was measured with ELISA from plasma collected 1 week after administration. The percent of F9 from ADK8-treated animal to ADK8-naïve animal and p value (t-test) is shown in FIG. 2*b*.

Figure 5A:
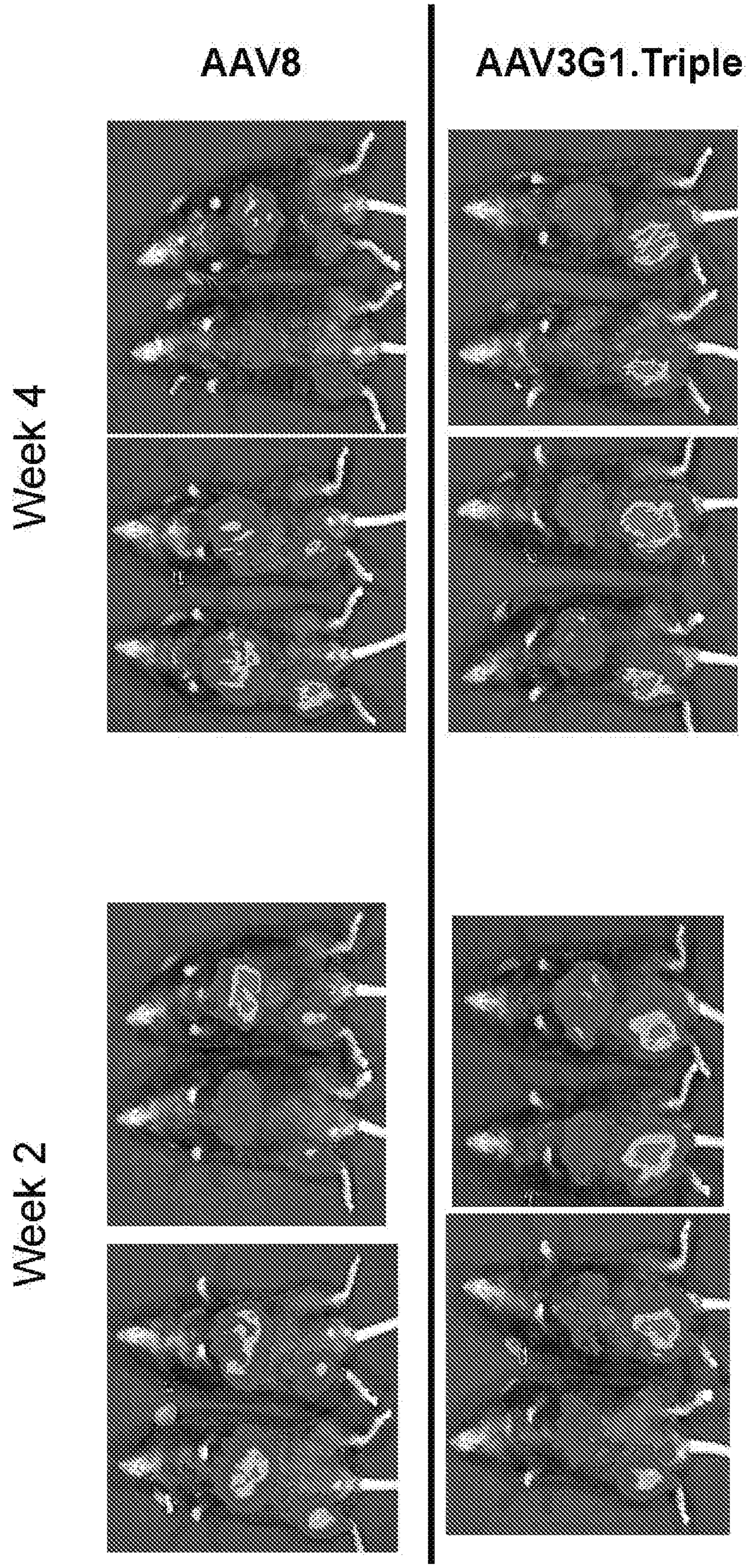
FIG. 5A are photographs of mice injected i.m. with AAV8 or AAV3G1 carrying a CB7.CI.luciferase cassette. Vector was administered into B6 muscle at a dose of $3\times10^{10}$ gc/mouse, 4 mice/group. Luciferase activity was monitored 2 weeks and 4 weeks after dosing. These findings demonstrate that, through intramuscular injection, AAV3G prefers muscle to liver, compared to AAV8. See Example 2C.
Figure 5B:
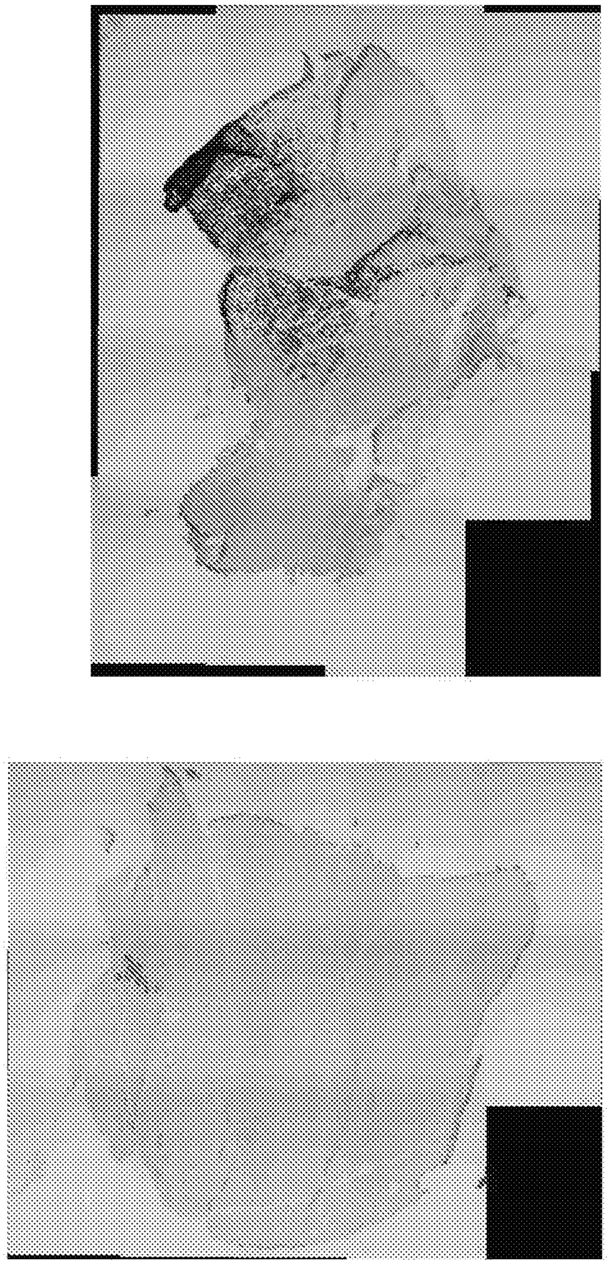
FIG. 5B are photographs of muscle tissue after i.m. injection of AAV vectors carrying a different transgene cassette from that shown in FIG. 5*a*. These experiments show similar muscle preference of AAV3G1 in B6 mice. Dose, $1\times10^9$ gc/animal, $5\times10^8$ gc/25 uL/leg, both legs. Week 3 after vector injection, muscle section, X-gal staining, the best section of each group, 4×.
Figure 5C:
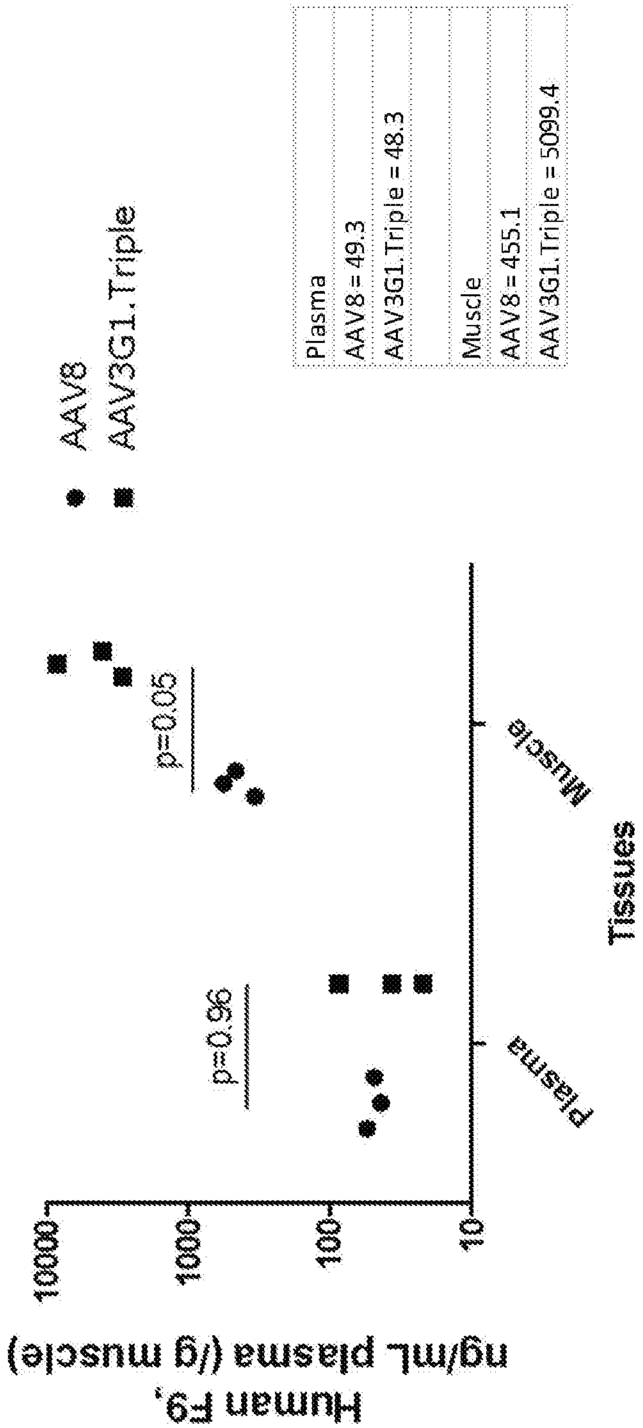
FIG. 5C. I.m. injection of AAV vectors carrying a third transgene cassette, tMCK.human F9, shows similar muscle preference of AAV3G1 in B6 mice. tMCK is a muscle-specific promoter. Dose, 3e10 gc/mouse, 3 mice/group. Plasma and muscle were collected 28 and 30 days after dosing, respectively. Human F9 was measured by ELISA from plasma and muscle lysate. The muscle F9 expression level of AAV3G1 was 11.2 folds of AAV8. See Example 2B6.
Figure 5D:
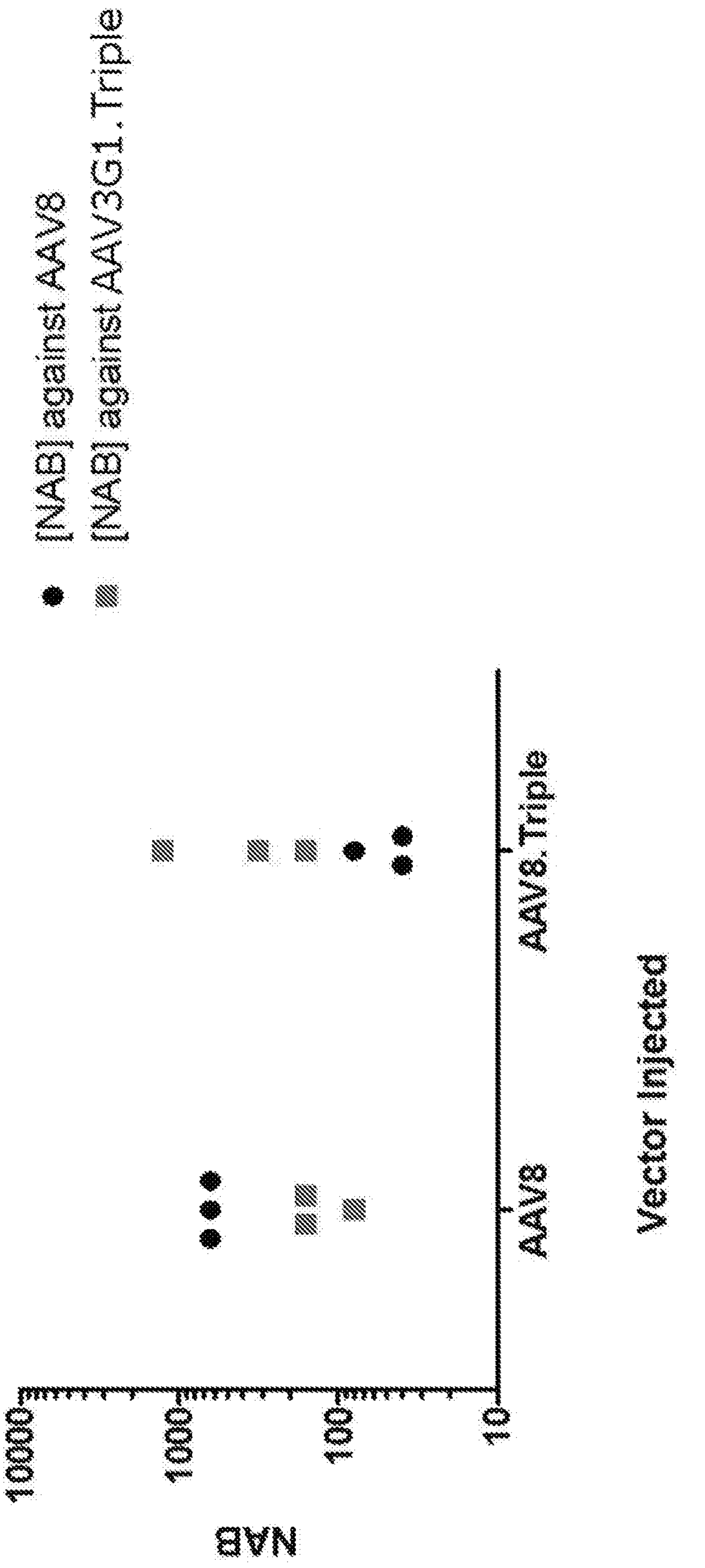
FIG. 5D. The neutralizing antibody titer of the day 28 plasma shows that the antigenicity of AAV8 and AAV3G1 is different. The plasma samples were from the study of FIG. 5*c*. See Example 2B6.

A similar experiment was done using human F9. I.m. injection of AAV vectors carrying a third transgene cassette, tMCK.human F9, shows similar muscle preference of AAV3G1 in B6 mice. tMCK is a muscle-specific promoter. Dose was $3\times10^{10}$ gc/mouse, n=3 mice/group. Plasma and muscle were collected 28 and 30 days after dosing, respectively. Human F9 was measured by ELISA from plasma and muscle lysate. The muscle F9 expression level after transduction with AAV3G1 was 11.2 folds higher than after transduction with AAV8. FIG. 5*c*. Measurement of the neutralizing antibody titer of the day 28 plasma shows that the antigenicity of AAV8 and AAV3G1 is different. FIG. 5*d*.

C. In Vitro Nab Assay, with Luciferase as the Reporter Gene

AAV8, AAV3G1 and mutants carrying all the combinations of the three mutations comprising AAV3G1 were tested in vitro with human plasmas (4 samples) and anti-AAV8 monkey sera (4 samples). Huh7 cells were seeded in 96-well black plates with clear bottom (Corning), $5\times10^4$ cells/well. Two days later, AAV8 and the variants were diluted in complete medium and incubated with diluted sera/plasma (final anti-AAV8 Nab titer in the mix, 1:4) before being applied to Huh7 cells in 96-well plates. The mixture was incubated at 37° C. for 30 minutes before being transferred to the Huh7 plates.

Figure 4A:
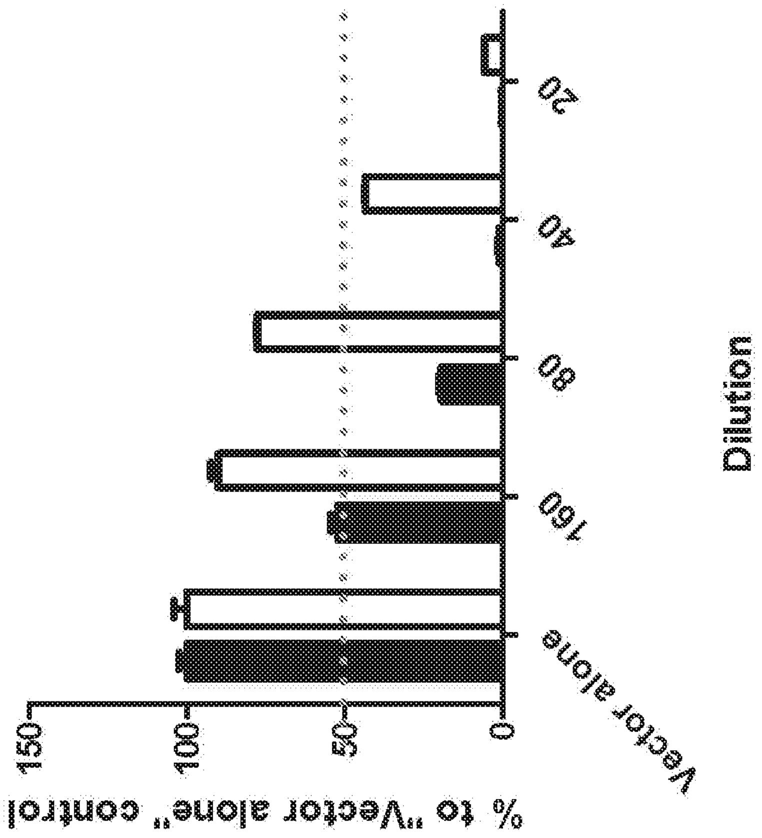
FIG. 4A demonstrates that AAV3G1 is resistant to pooled human IVIG (hIVIG), compared to AAV8. AAV8 (filled bar) or AAV3G1 (open bar) carrying CB7.CI.luciferase cassette were incubated with various dilution of pooled human IVIG before applied to Huh7 cells in 96 well plates (M.O.I., ~1e4). Luciferase level was read 72 hours after infection. The x-axis is the dilution fold of hIVIG. The y-axis represents the percentage of luciferase expression compared to "vector alone" control. The gray dot line indicates 50% expression level.
Figure 4B:
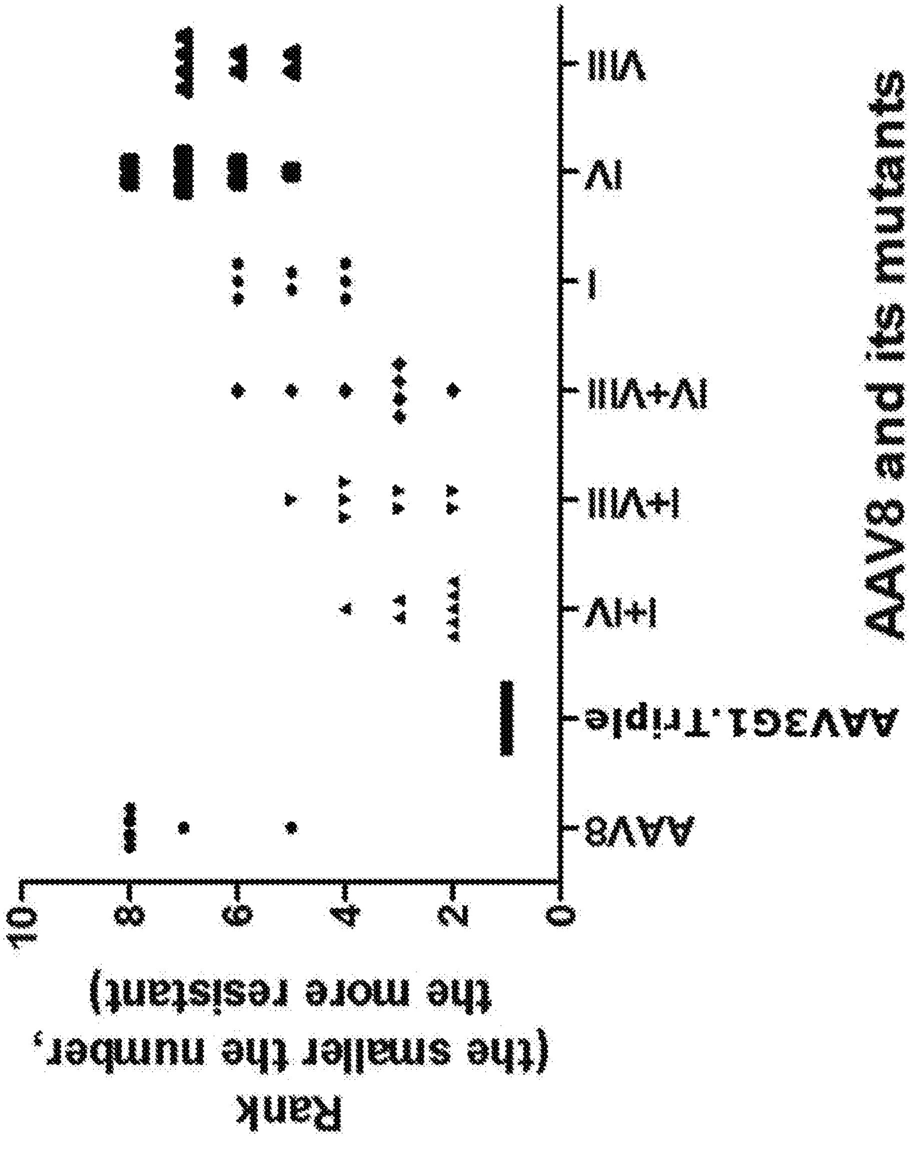
FIG. 4B demonstrates that all three mutations in AAV3G1 contribute to Nab resistance. AAV8, AAV3G1 and mutants carrying all the combinations of the three mutations comprising AAV3G1 were tested in vitro with human plasmas (4 samples) and anti-AAV8 monkey sera (4 samples). AAV8 and the variants were incubated with diluted sera/plasma (final anti-AAV8 Nab titer in the mix, 1:4) before applied to Huh7 cells in 96-well plates. Luciferase expression was read 72 hours later and converted to the percentage of the expression level of each "vector alone" control. for each serum/plasma, a ranking number was assigned to each vector according to their residual expression (the ranking number of the highest residual expression was 1 and the lowest was 8). See Example 2C.

Luciferase expression was read 72 hours later and converted to the percentage of the expression level of each "vector alone" control. For each serum/plasma, a ranking number was assigned to each vector according to their residual expression (the ranking number of the highest residual expression was 1 and the lowest was 8). FIG. 4*b*. These data show that all the three mutations in AAV3G1 contribute to Nab resistance.

1. Luciferase Assay, In Vivo

AAV8 or AAV3G1 carrying CB7.CI.luciferase cassette was administrated intramuscularly into C57BL6 mice at a dose of $3\times10^{10}$ gc/mouse, 4 mice/group. Luciferase activity was monitored 2 weeks and 4 weeks after dosing. Through intramuscular injection, AAV3G1 prefers muscle to liver, compared to AAV8. FIG. 5*a*.

A second experiment was performed in which AAV8 and AAV3G1 vectors carrying a different transgene were administered i.m. in C57BL6 mice at a dose of $1\times10^9$ gc/animal ($5\times10^8$ gc/25 uL/leg, both legs). Week 3 after vector injection, muscle section, X-gal staining, the best section of each group, is shown in FIG. 5*b* (4× magnification). These studies show that i.m. injection of AAV vectors carrying another transgene cassette shows similar muscle preference of AAV3G1 in B6 mice.

Figure 6A:
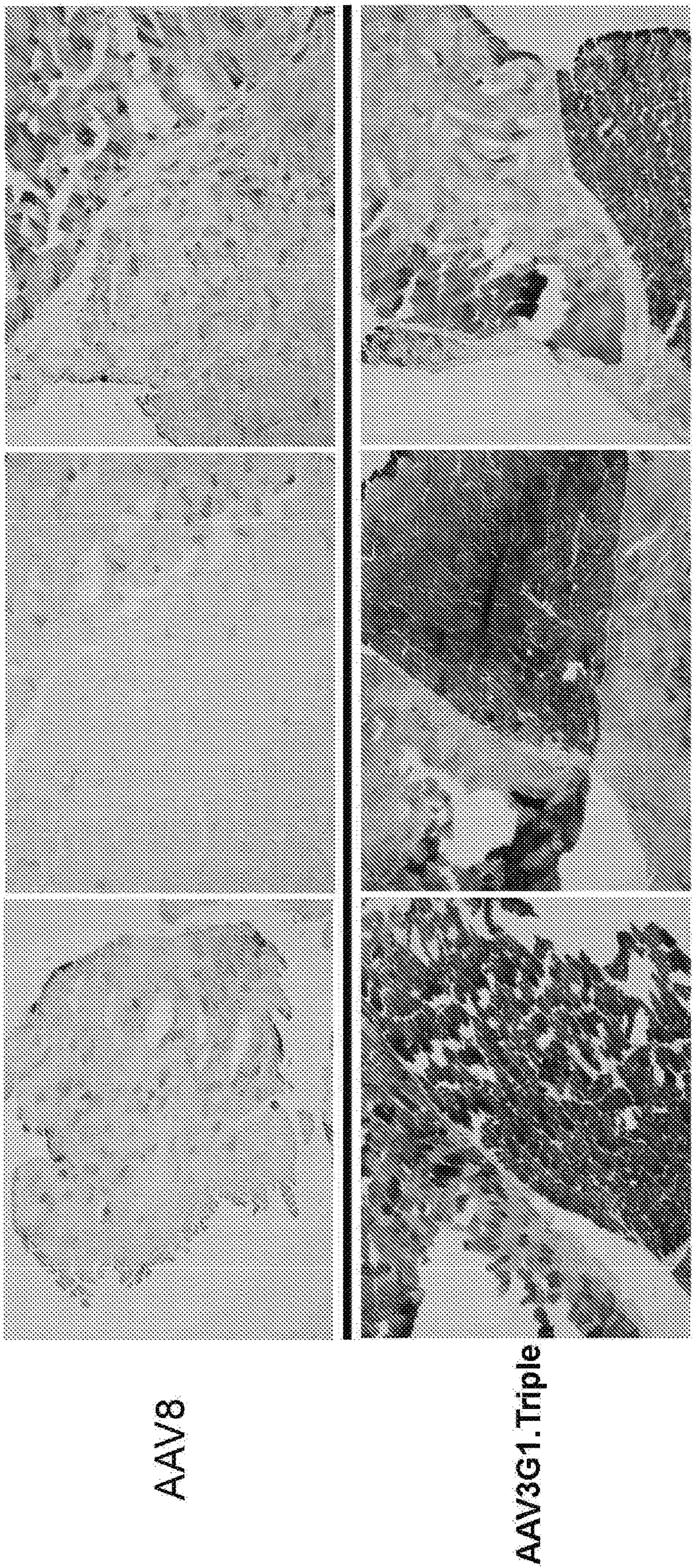
FIG. 6A. Overview of X-gal stained sections from heart, muscle and liver of mice received AAV8 or AAV3G1 vector. MPS 3A Het mice (B6 background) received 5e11 gc of AAV.CMV.Lac/mouse, i.v. Tissues were collected 14 days later. Representative muscle sections of each animal at 4×. See Example 2C.

MPS 3A Het mice (C57BL6 background) received $5\times10^{11}$ gc of AAV.CMV.Lac/mouse, i.v. Tissues were collected 14 days later. X-gal stained sections from heart, muscle and liver of mice received AAV8 or AAV3G1 vector were made (data not shown). These studies show that i.v. injection shows increased muscle preference in AAV8. Triple as compared to AAV8. Representative muscle sections of each animal at 4× are shown in FIG. 6*a*.

Figure 6B:
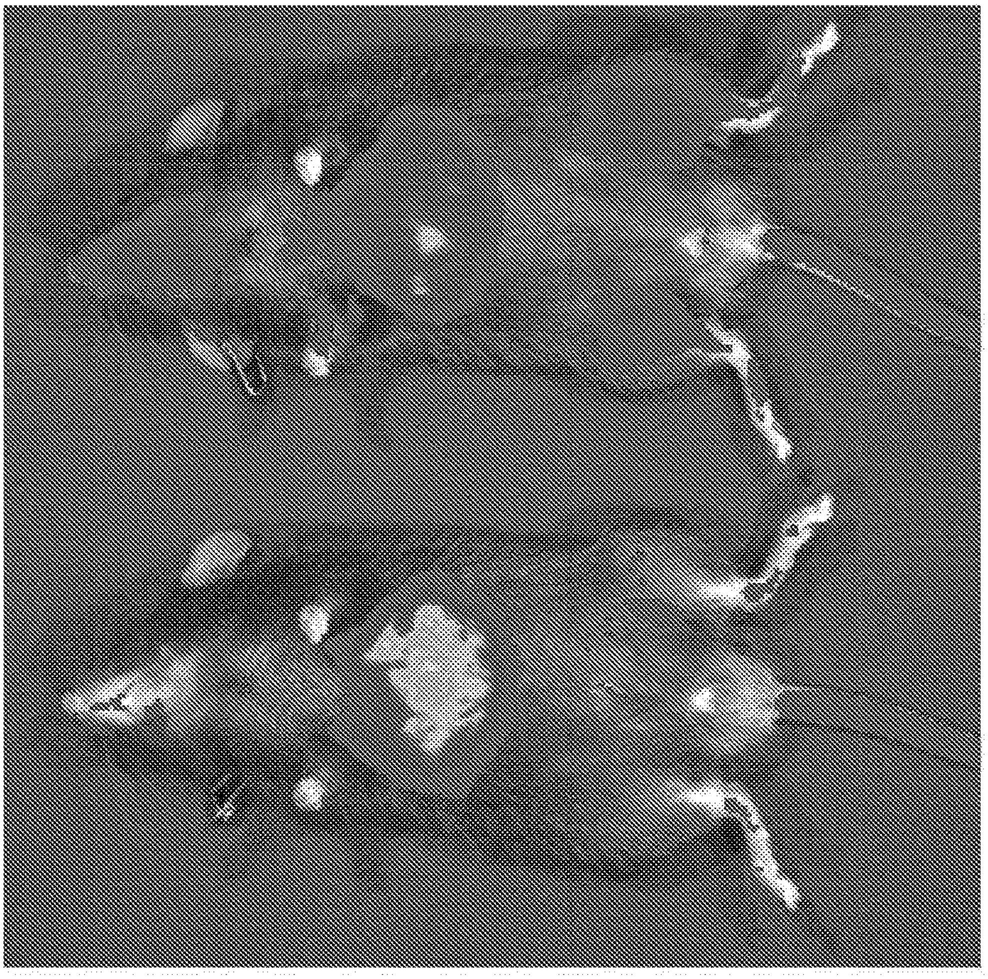
FIG. 6B. Representative image of in vivo luciferase imaging, to compare AAV8 and AAV3G1 with CB7.CI.ffluciferase transgene cassette, i.v., in B6 mice. Dose, 3e11 gc/mouse, week 2 after vector injection. The left is AAV8; the right is AAV3G1. See Example 2C.

AAV8 and AAV3G1 were compared with CB7.CI.ffluciferase transgene cassette. B6 mice were injected, i.v., at a dose of $3\times10^{11}$ gc/mouse. Two weeks after vector injection, luciferase was imaged. FIG. 6*b*. The left is AAV8; the right is AAV3G1.

Figure 7A:
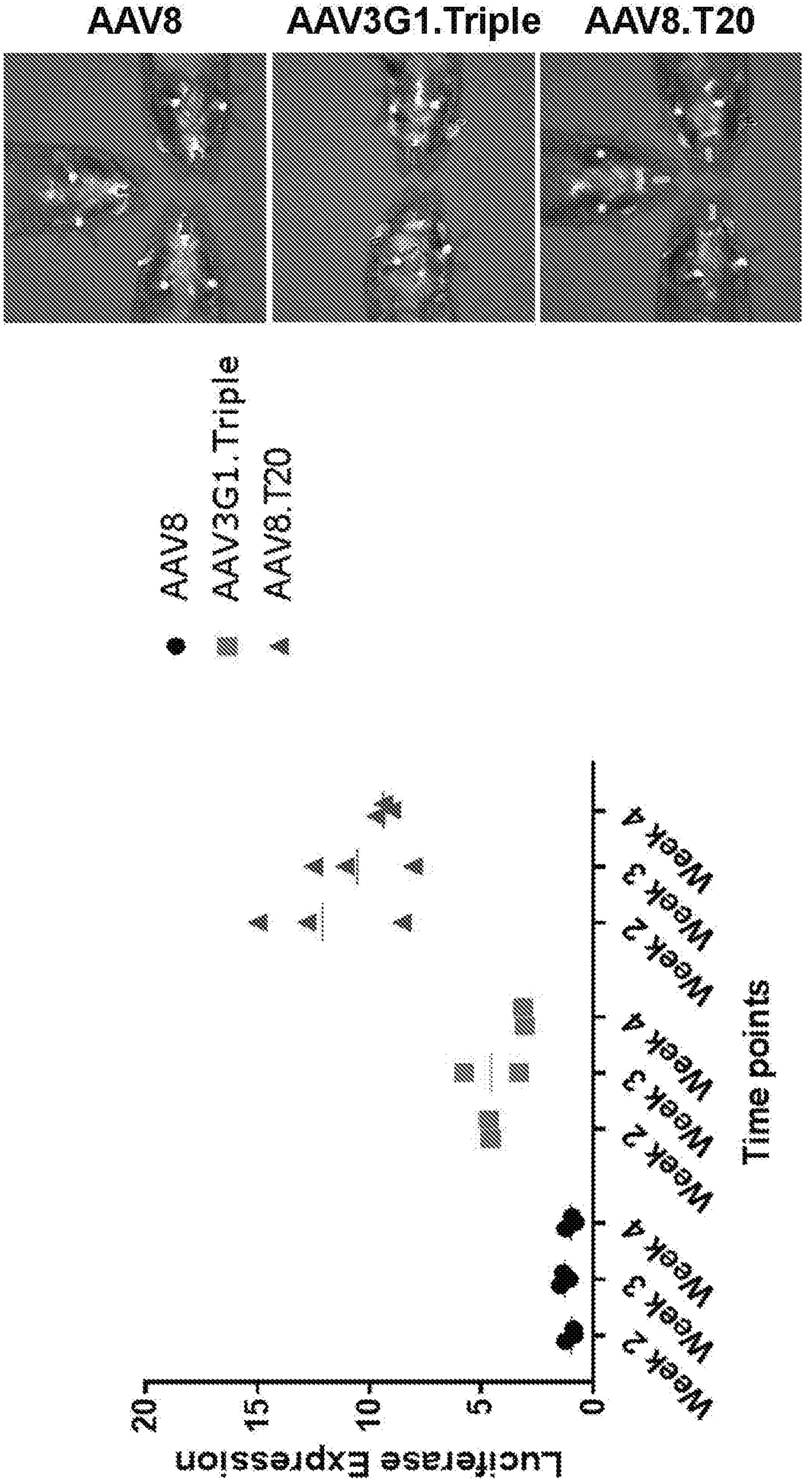
FIG. 7A. AAV3G1 has a higher transduction to mouse airway epithelial cells and the transduction is improved further by replacing VP12 region with rh.20. B6 mice received 1e11 gc/mouse of AAV.CB7.CI.luciferase, i.n. The luciferase activity was monitored 2, 3 and 4 week after vector administration. The right panel is a representative image (week 4) of the study. The left panel is quantification with Living Image® 3.2 and normalized by the average value of AAV8 group at week 2. See Example 2C.

AAV3G1 has a higher transduction to mouse airway epithelial cells and the transduction is improved further by replacing VP1/2 region with rh.20. B6 mice received $1\times10^{11}$ gc/mouse of AAV.CB7.CI.luciferase, i.n. 4 mice received each vector. The luciferase activity was monitored 2, 3 and 4 week after vector administration. FIG. 7*a*, right panel, is a representative image (week 4) of the study. The left panel is quantification with Living Image® 3.2 and normalized by the average value of AAV8 group at week 2.

Figure 7B:
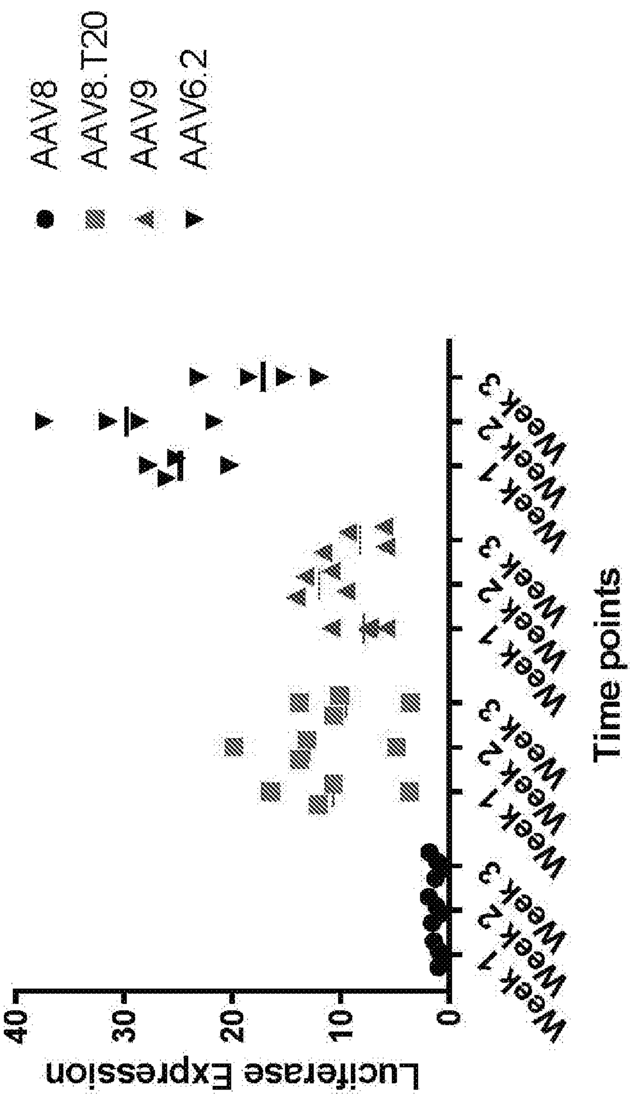
FIG. 7B. Airway epithelia cell transduction comparison of AAV8, AAV8.T20, AAV9 and AAV6.2. B6 mice received 1e11 gc/mouse of AAV.CB7.CI.luciferase, i.n., 4 mice/vector. The luciferase activity was monitored 1, 2 and 3 week after vector administration. Living Image® 3.2 was used for quantification and normalized by the average value of AAV8 group at week 1. See Example 2C.

Airway epithelia cell transduction comparison of AAV8, AAV8.T20, AAV9 and AAV6.2. B6 mice received $1\times10^{11}$ gc/mouse of AAV.CB7.CI.luciferase, i.n., 4 mice/vector. The luciferase activity was monitored 1, 2 and 3 weeks after vector administration. Living Image® 3.2 was used for quantification and normalized by the average value of AAV8 group at week 1. FIG. 7*b*.

Mice were anaesthetized. D-luciferin (Xenogen) was instilled into the mouse nostril at 15 ug/uL, 10 uL/nostril, 20 uL/mouse. Five minutes later, luminescent images were taken by IVIS® Imaging Systems (Xenogen) and quantified with the software Living Image® 3.2.

2. Heparin Binding Assay

AAV vectors were diluted in desired buffers and loaded to vector-dilution-buffer-prebalanced HiTrap Heparin HP column (GE Healthcare Life Sciences) by AKTA™ FPLC System (GE). The column was then washed sequentially with vector dilution buffer and buffers with increasing amount of sodium chloride. Fractions were collected during the whole process. Dot blot protocol was described by Tenney, R M, Bell, C L, and Wilson, J M (2014). AAV8 capsid variable regions at the two-fold symmetry axis contribute to high liver transduction by mediating nuclear entry and capsid uncoating. Virology 454: 227-236, which is incorporated herein by reference. See FIGS. 8*a*-8*d*. Yield for each vector is shown below.

chosen. Two helper plasmids, pAdΔF6 (carrying adenovirus components) and pRep (carrying AAV Rep genes), and the plasmid library were transfected into HEK293 cells for AAV library production. The downstream steps utilized AAV vector manufacturing techniques previously described. The plasmid library size was around $1\times10^6$-$3\times10^7$. The yield of AAV libraries was around $1.52\times10^{11}$-$2.56\times10^{13}$ gc.

Structure-guided saturation mutagenesis quickly abolished vector neutralization by the antibody. We first picked residues 583, 588, 589, 594-597 (AAV8 VP1 numbering, SEQ ID NO: 34) for mutagenesis, because they're within the contact region between monoclonal neutralizing antibody ADK8 and AAV8 capsid, according to the structure resolved by Gurda et al. After one round of in vitro selection in HEK293 cells in the presence of ADK8, mutants were randomly picked and tested with Nab assay. The mutation sequences are listed in Table 1. As shown in FIG. 2A, all the mutants were resistant to ADK8 in comparison to AAV8. They also show resistance to ADK8/9, implying epitope overlapping between the two antibodies. One mutant, C42, showed much higher 293 cell transduction than AAV8, probably due to the change of residue 589 to arginine. Huh7 cells showed similar result (data not shown).

Liver transduction was evaluated in B6 mice. Mice received CB7.CI.eGFP vectors at a dose of $1\times10^{11}$ GC/animal, i.v., and liver was harvested two weeks later. The dosage of G112 was $3.5\times10^{10}$ per animal. Liver transduction in B6 mice with CB7.CI.eGFP reporter showed that GFP expression of C41, G110 and G112 was better than AAV8;

TABLE 3

| Yield table (total gc of purified vector/cell stack. DIY) | | | | |
|---|---|---|---|---|
| | Transgene cassette | | | |
| AAV types | CB7.C1.ffluciferase.RBG | LSP.cF9.W | TBG.hF9.W | tMCK.hF9.W |
| AAV8 | 4.93E+12 | 4.65E+13 | 4.47E+13 | 1.84E+13 |
| | 2.07E+13 | 2.04E+13 | | |
| | 2.10E+13 | | | |
| AAV8.C41 | 1.46E+13 | 1.69E+13 | | |
| AAV8.C41.I-SGTH | 3.64E+12 | | | |
| | 5.63E+12 | | | |
| | 6.64E+12 | | | |
| AAV8.C41.IV-GGSRP | 1.40E+13 | | | |
| AAV8.G112 | | 7.14E+12 | | |
| AAV8.G113 | | 1.93E+13 | | |
| AAV8.G115 | | 1.86E+13 | | |
| AAV8.I-SGTH | 1.78E+13 | | | |
| AAV8.IV-GGSRP | 2.24E+13 | | | |
| AAV8.T20 | 5.60E+12 | | | |
| AAV8.TR1 | | | 4.64E+13 | |
| AAV3G1 | 3.95E+12 | 2.12E+13 | 1.63E+13 | 1.98E+13 |
| | 8.43E+12 | | | |
| | 1.04E+13 | | | |

Example 3: Detailed Studies

Figure 14:
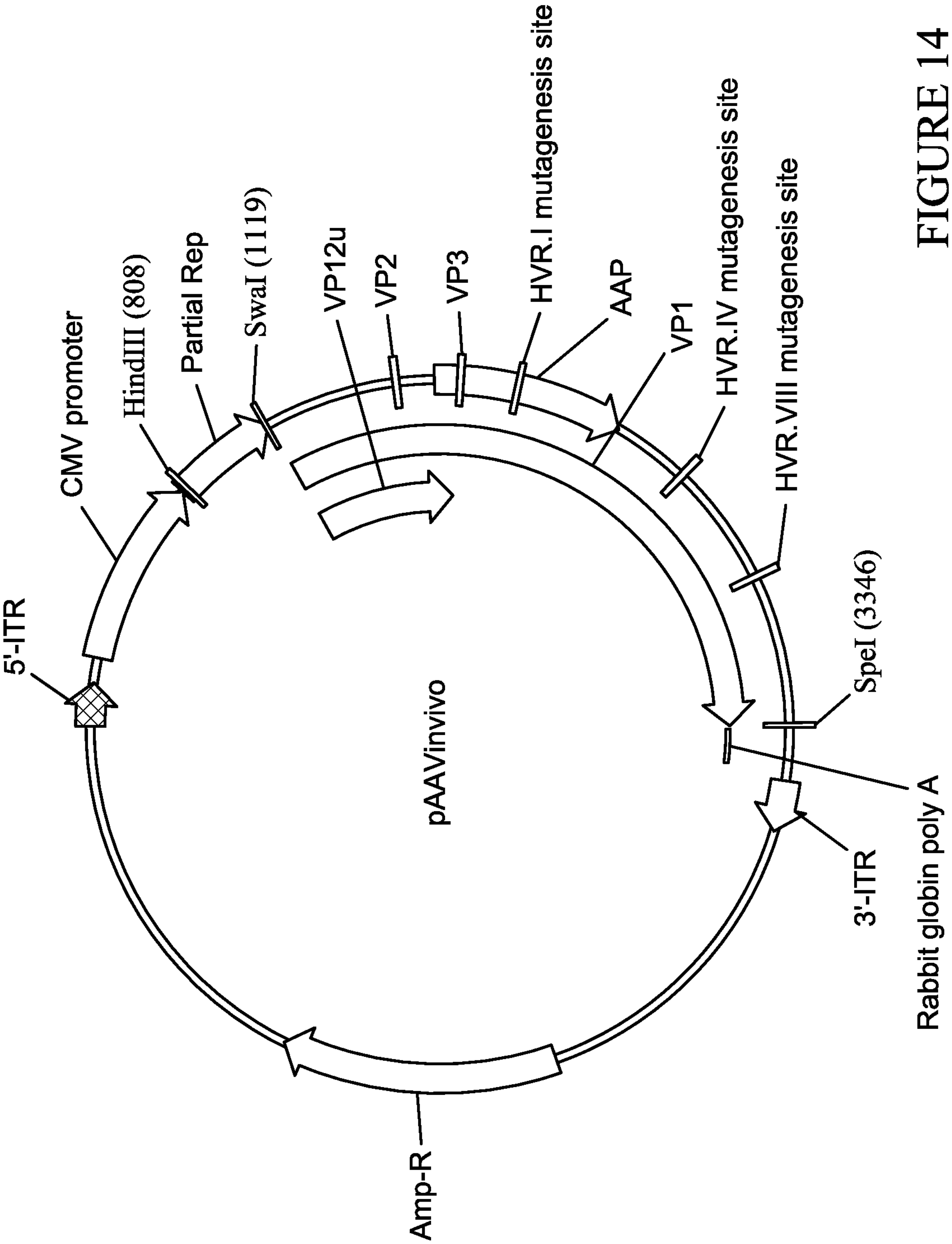
FIG. 14 provides a map of pAAVinvivo.

AAV mutant library preparation. A plasmid, termed pAAVinvivo, was used for the library preparation. The plasmid contains CMV promoter, partial Rep sequence (AAV2, NC_001401, 1881-2202)18, AAV8 VP1 gene and rabbit beta globin (RBG) polyadenylation signal, flanked by two AAV ITRs (FIG. 14). The saturation mutagenesis was done with primers carrying NNK degenerate codons at the desired sites. Both NNS and NNK covers all 20 amino acids. For human codon usage, NNS is slightly higher than NNK (FIG. 15A); however, too many GCs may not be good for PCR and/or virus replication—the average GC % of NNS is 67% while NNK 50% (FIG. 15B). Taken together, NNK was G113 and G115 were roughly equal to AAV8; in contrast to its high 293 cell transduction, C42 expressed less GFP in mouse liver (Data not shown).

The resistance remained in in vivo testing when LSP.canine F9 transgene cassette was packed into those AAV8 mutants and administrated intravenously into mice 2 hours after ADK8 i.v. injection (FIG. 2B). No mutants showed clear resistance to several AAV8 Nab-positive human plasmas (data not shown), which was expected because those mutants are single-epitope ablated and AAV antisera are likely polyclonal, as demonstrated by the broad neutralizing spectrum of AAV Nab in chimpanzees.

Further mutagenesis and the generation of AAV3G1. One mutant, C41, showed some resistance to two AAV8 Nab-positive human plasmas, when tested in vivo with CB7.CI.eGFP transgene cassette (data not shown). This mutant was used as the backbone for further mutagenesis. HVR.I and HVR.IV region were picked for the next round of mutagenesis, respectively, because protrusions of a protein are likely to be more antigenic. (NNK)5 were loaded into pAAVinvivo.C41 backbone (pAAVinvivo.C41 is the same as pAAVinvivo with AAV8 VP1 replaced with AAV8.C41 VP1) at position 263-267 and 455-459 respectively to make libraries and then go through three round of in vivo selection in mice. For each round, AAV libraries were intravenously injected into mice 2 hour after pooled human Intravenous Immunoglobulin (hIVIG) injection. AAV sequences were retrieved with PCR from mouse livers two weeks after vector injection and loaded into pAAVinvivo.C41 to make libraries for the next round of selection with increased amount of hIVIG. After three rounds of selection, SGTH was the only mutant recovered from the highest IVIG group among all PCR positive animals. It's interesting that it's a three-bp deletion mutant which doesn't disrupt the ORFs of VP123 and assembly activation protein (the DNA change is: AACGGGACATCGGGA (SEQ ID NO: 83)→TCTGGTACTCAT (SEQ ID NO: 84). HVRIV's signal was still diverse, implying that it's conformationally flexible and may not be the dominant epitope in pooled hIVIG. AAV3G1 was generated by combining the three mutations, C41 (HVRVIII mutation), SGTH (HVRI mutation) and GGSRP (HVR.IV mutation) together into AAV8 backbone. GSRP was picked because it showed the highest resistance to hIVIG in in vitro Nab assay, among all HVR.IV mutants tested (data not shown).

AAV3G1 showed Nab resistance and all the three mutations contributed to the resistance. AAV3G1 showed resistance to hIVIG (FIG. 4A). To figure out each mutation's contribution to the resistance, we made a series of AAV8 mutants plus AAV8 and AAV3G1 to cover all the combinations and tested them with anti-AAV primate sera or plasma. As shown in FIG. 4B, all the three mutations comprising AAV3G1 contributed to Nab resistance.

Figure 8A:
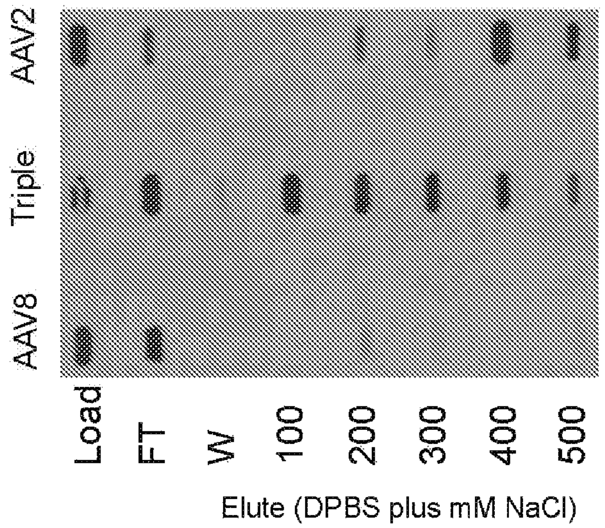
FIG. 8A. The heparin affinity of AAV3G1 is increased. AAV vectors were diluted in DPBS and 2e11 gc of the vector was loaded to Heparin column, followed by washing with DPBS and DPBS with various concentrations of NaCl. Dot blot was performed with PVDF membrane with antibody B1.
Figure 8B:
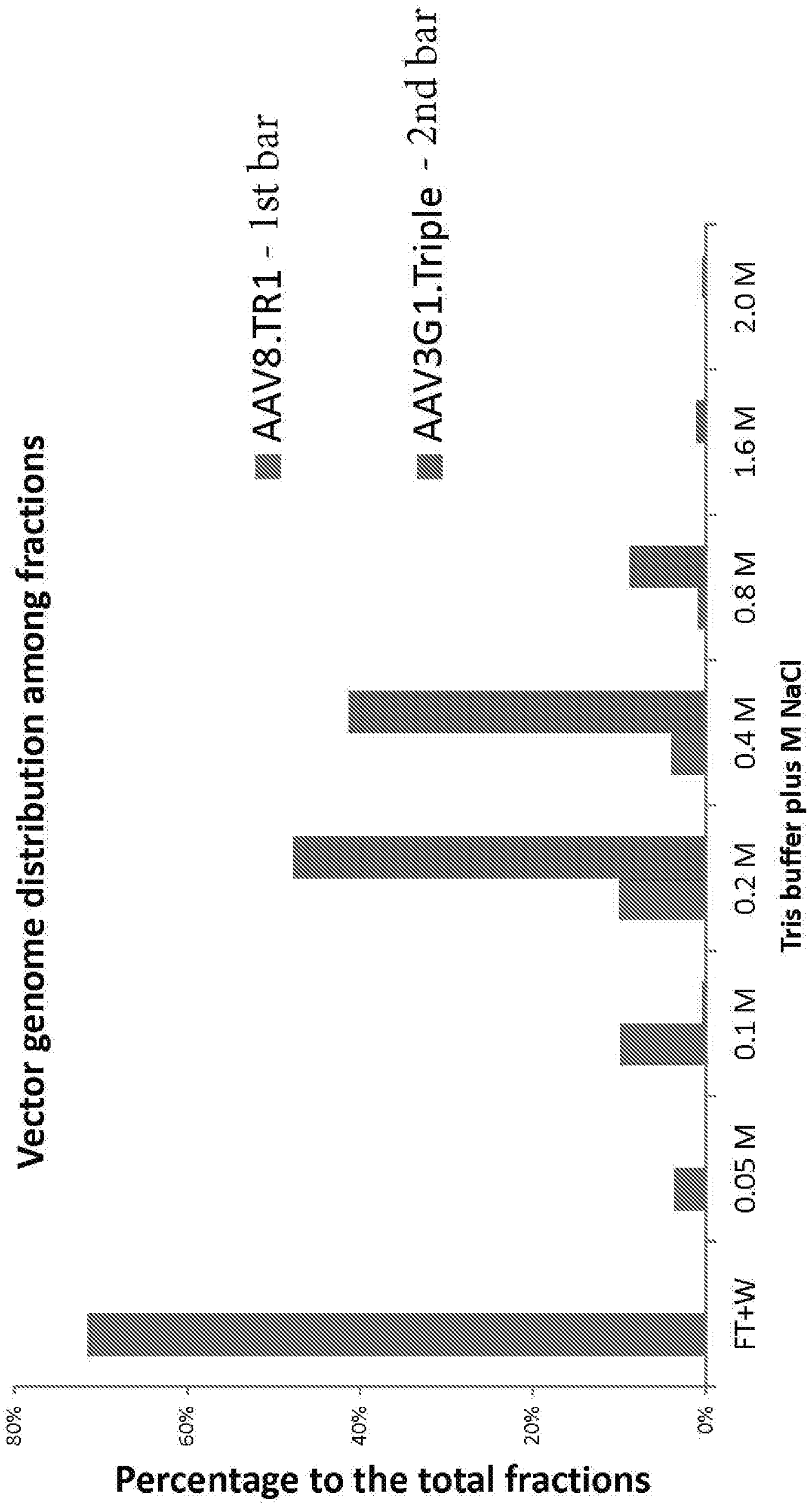
FIG. 8B. The charge reduction in AAV8.TR1 decreases its heparin affinity. Equal gc of AAV8.TR1.TBG.hF9co.WPRE.bGH and AAV3G1.CB7.CI.luciferase.RBG were mixed together in Tris buffer (pH 7.4, 0.01 M), loaded onto heparin column and washed sequentially with various buffers. Fractions were collected during the process: FT+W, flow-through plus wash with Tris buffer, 0.05 M-2.0 M. Tris buffer plus 0.05-2.0 M NaCl. Vector distributions were measured by qPCR with bGH and RBG probes.
Figure 8C:
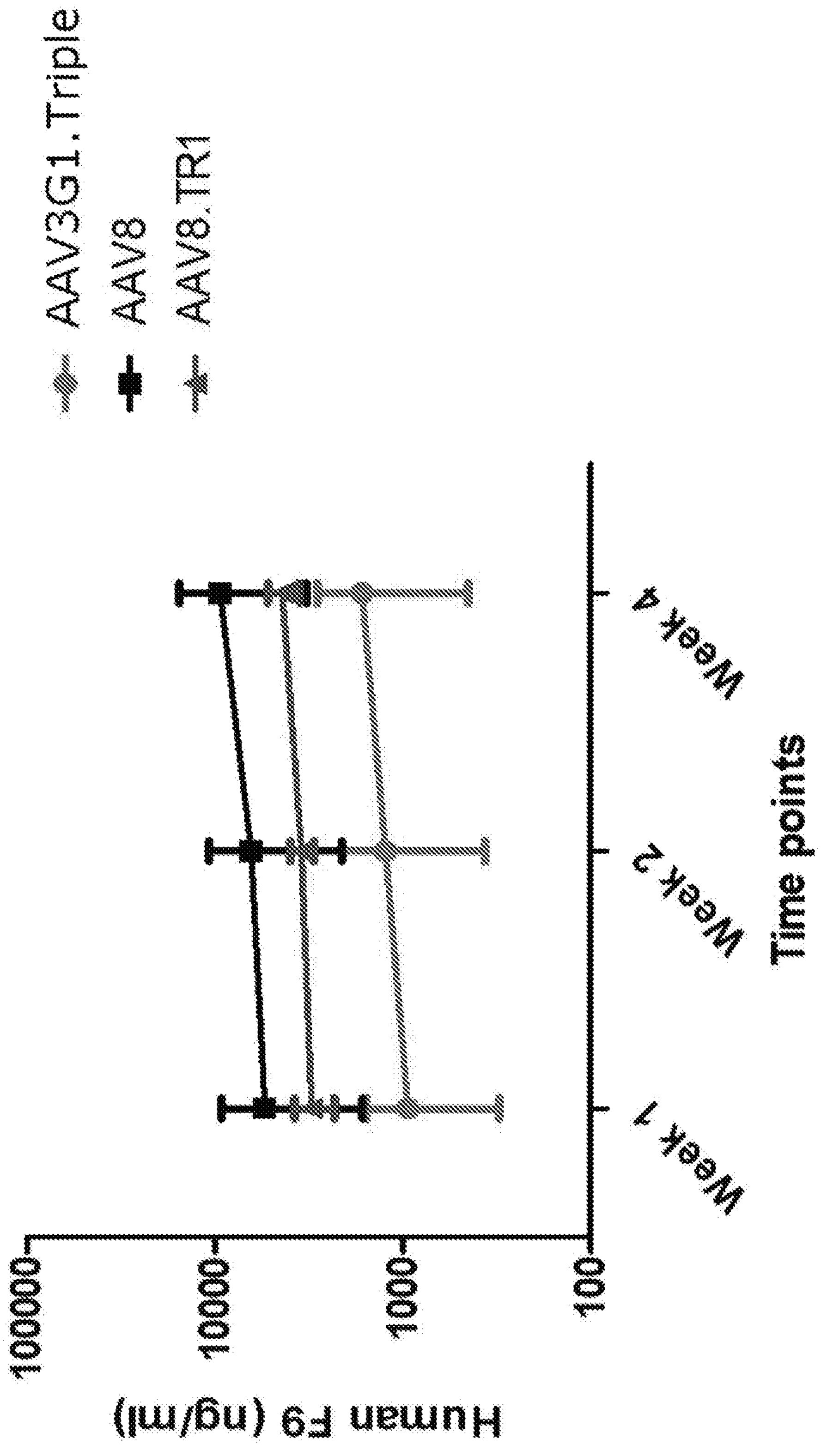
FIG. 8C shows charge reduction of AAV3G1, resulting the in the mutant AAV8.TR1, restores liver transduction partially. B6 mice were administrated intravenously with AAV.TBG.hF9co. WPRE.RBG at a dose of 1e10 gc/mouse, 5 mouse/group. Plasma was collected week 1, 2 and 4 after vector injection and measured by human F9 ELISA.
Figure 8D:
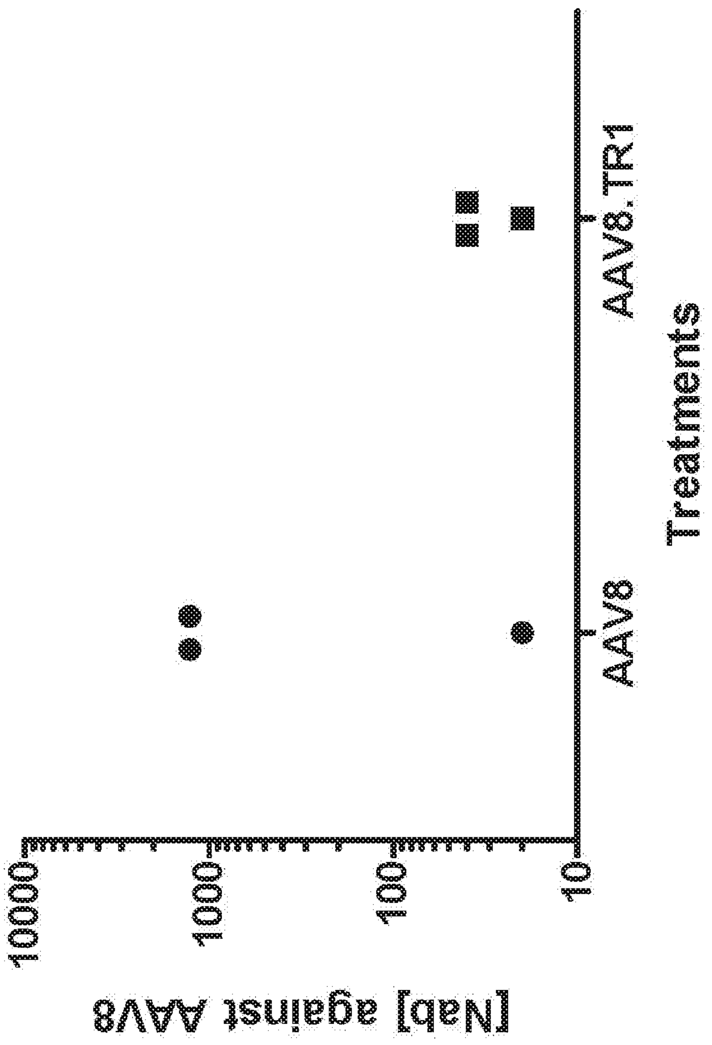
FIG. 8D provides results of in vitro Huh7 Nab assy. Reporter:CB7.CI.ffluciferase; M.O.I. ~1e3. The samples were Week 4 plasma from 3 animals each group of the same study as FIG. 8C.
Figure 8E:
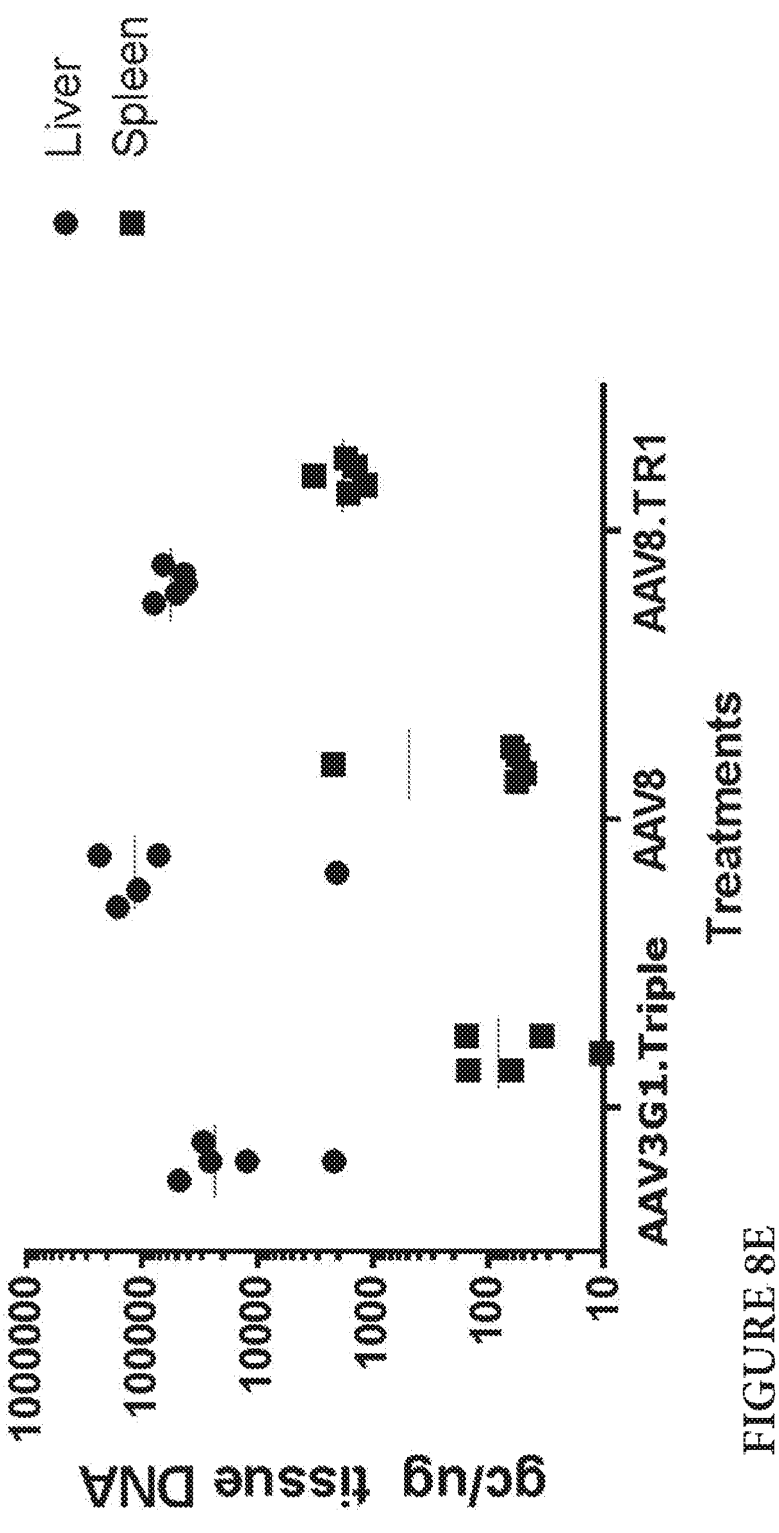
FIG. 8E provides the vector genome copy distribution from the mice of FIG. 8C.
Figure 13A:
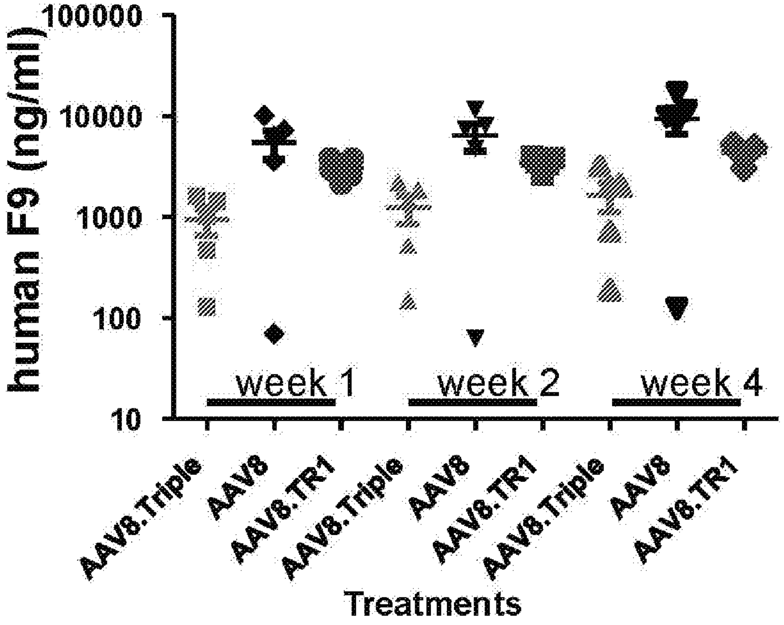
FIG. 13A is a graph showing human F9 expression (ng/mL) in mice (5 mice/group) injected with AAV.TBG.human F9 at 1e10 gc/mouse, i.v. Plasma was collected 1, 2 and 4 weeks after treatment.
Figure 13B:
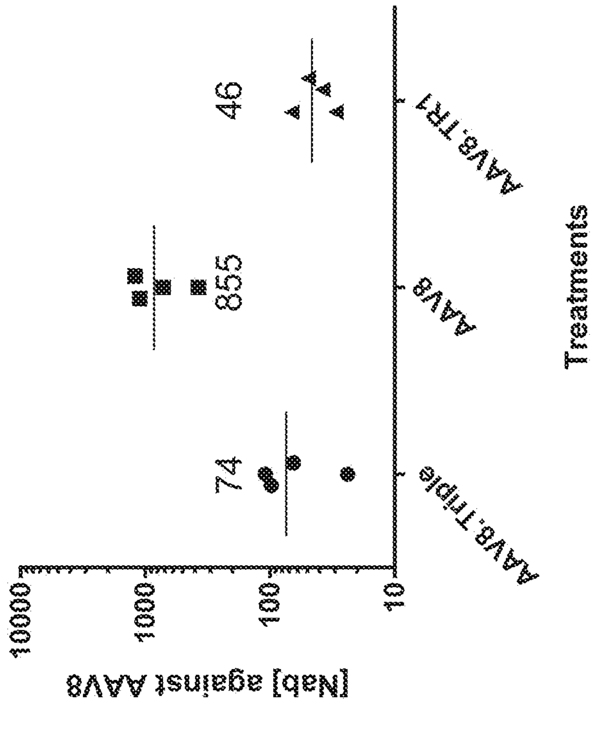
FIG. 13B is a graph showing neutralizing antibody titer against AAV8 at week 4 in the mice of FIG. 13A. Huh7 cells were used with AAV8.CB7. Luciferase at a final concentration of 1e9 gc/mL. The average of each group is indicated.

The liver transduction of AAV3G1 is down while its muscle transduction is up. We evaluated liver transduction of AAV3G1 in mice with TBG.human F9 (hF9) as the reporter gene. At a dose of $1\times10^{10}$ gc/animal, i.v., F9 expressed in plasma was around 18% of AAV8, at weeks 1, 2 and 4 after vector administration (FIG. 13A). The neutralizing antibody titer against AAV8 from AAV3G1 injected mice was 12 fold less than AAV8 injected animals (FIG. 13B). Consistent to F9 expression data, the vector genome copies in liver of AAV3G1 was 20% of AAV8. For both treatments, the liver/spleen ratio of vector genome DNA was similar, with AAV3G1 being 285 and AAV8 being 237 (FIG. 8E). We then evaluated muscle transduction of AAV3G1 in mice. Three reporter gene cassettes were used: CB7.CI.luciferase, CMV.LacZ and tMCK.hF9. As in FIG. 5*a*, intramuscular injection of 3e10 gc of CB7.luciferase clearly showed that a large amount of AAV8 vectors went to liver, consistent to previous study; in contrast, for AAV3G1, the muscle transduction was much higher than AAV8 and a smaller proportion of vectors went to liver. Intravenous injection showed similar results (FIG. 6*c*). So did CMV.LacZ with both i.m. and i.v (FIGS. 5B, 6A) and tMCK.hF9 with i.m. (FIG. 5C). For tMCK.hF9 i.m. injection, F9 level in the muscle lysate from AAV3G1 injected mice was about 10 fold higher than AAV8; in contrast, plasma F9 level of the two vectors was similar, consistent with previous report that muscle is not an ideal tissue for F9 expression. We also measured the Nab in the tMCK.hF9 study. Consistent with the study described previously in the paper, AAV8 Nab in AAV8-injected mice was higher than AAV3G1-injected mice (around 12 fold) while AAV3G1 Nab in AAV8-injected mice was lower than AAV3G1-injected mice (around 4 fold) (FIG. 5D). The results show that AAV3G1 has better muscle transduction than AAV8 and indicates that the two capsids are serologically different.

The heparin affinity of AAV3G1 is increased and the rational design of reducing its surface charges successfully reduced its heparin affinity and partially restored its murine liver transduction. Liver transduction of AAV3G1 is decreased despite two of its three mutations identified in three rounds of in vivo selection in mouse liver on the AAV8.C41 backbone. Heparin binding assay showed that the affinity of AAV3G1 is increased (FIG. 8A). Binding to heparin or some other negative charged macromolecules could cause the vectors become trapped/captured before they reach hepatocytes. To eliminate heparin binding, we introduced negative charges onto AAV3G1 capsid, by changing SGTH, the HVR.1 mutation, to SDTH, and replacing GGSRP, the HVR.IV mutation, to another negative-charged mutation showing up during the selection process, DGSGL, resulting in a new mutant—AAV8.TR1. The modifications successfully reduced heparin binding (FIG. 8B), and the liver transduction was partially restored (FIG. 13A). The AAV8 Nab titer was 19 fold less than AAV8-treated mice (FIG. 13B). Surprisingly, spleen vector DNA of AAV8.TR1 treated mice was higher than AAV8-treated ones (FIG. 8E). The transduction of AAV3G1 was higher than AAV8 in mice through intranasal vector administration and the rational design of replacing its VP1/2 region with rh.20 improved the transduction further. As shown in FIG. 7*a*, AAV3G1's transduction was higher than AAV8 in mice through intranasal administration. A previous comprehensive study showed various airway transduction among AAVs. By analyzing the data from Table 1 in Limberis, M P et al, (2009). Transduction efficiencies of novel AAV vectors in mouse airway epithelium in vivo and human ciliated airway epithelium in vitro. Mol Ther 17: 294-301, which is incorporated herein by reference, we found that codon 24 is distinct between low score members and high score members of AAV clade E (data not shown), especially between rh.39 and hu.37—the two have only one amino acid difference (A24D) while their scores are quite different (4 vs 13). We reasoned that VP1/2 region may play some role in AAV airway transduction.

By replacing VP1/2 region (1-202) of AAV3G1 with rh.20, we created another mutant called AAV8.T20. Indeed, AAV8.T20's transduction was 8-12 fold higher than AAV8 (FIG. 7B), approaching to AAV9 level (FIG. 7B).

Material and Methods

Animal Studies.

All mice for the study were housed in an Association for Assessment and Accreditation of Laboratory Animal Care-accredited and Public Health Service-assured facility at the University of Pennsylvania. All animal procedures complied with protocols approved by the Institute of Animal Care and Use Committees at the University of Pennsylvania. All mice were bought from the Jackson Laboratory (Bar Harbor, Me.). The mice were C57BL/6J mice (male, 6-8 weeks old) unless specifically described. Plasmid Library construction.

The starting plasmid, pAAVinvivo, is shown in FIG. 14. HVR.VIII mutagenesis library was constructed by PCR with Phusion (Thermo Fisher Scientific, MA) and a degenerate oligo CTACAGAGGAATACGGTATCGTGNNKGA-TAACTTGCAGNNKNNKAACACGGCTCCT NNKNNKNNKNNKGTCAAC AGCCAGGGGGCCTTAC (SEQ ID NO: 85), followed by cloning into pAAVinvivo and transformation into Stbl4 competent cells (Invitrogen, Calif.) by electroporation. The initial libraries of HVR.I and HVRIV were constructed in the same way, with the degenerate oligo CAACCACCTCTA-CAAGCAAATCTCCNNKNNKNNKNNKNNKGGAGC-CACCAACGAC AACACCTACT (SEQ ID NO: 86) for HVR.I and CTACTTGTCTCGGACTCAAACAA-CANNKNNKNNKNNKNNKACGCAGACTCTGGGCT TCAGCCAA (SEQ ID No:87) for HVRIV.

The cloning plasmid was pAAVinvivo.C41—AAV8 VP1 replaced with AAV8.C41 VP1. After round one selection, AAV sequences were retrieved with primers flanked with BsmBI sites and cloned into two new cloning plasmids constructed on pAAVinvivo.C41 by removing the two endogenous BsmBI sites by silent mutations and then introducing two BsmBI sites flanking HVR.I and HVR.IV, respectively. The competent cells used here was MegaX DHIOB™ T1R Electrocomp™ Cells (Invitrogen, Calif.) instead. The virus libraries were made the same way as regular AAV vector preps.

AAV Library Production.

For HVR.VIII, The plasmid library was mixed with pdeltaF6 and pRep and transfected into EK293 cells with Calcium-phosphate method. Three days after transfection, cell lysate was harvest, re-suspended in DPBS and treated with Benzonase (Merck). The lysate was then spinned down to remove debris. The supernatant was the AAV mutagenesis library and stored at −20° C. for further uses. For HVR.I and HVRIV, the libraries were made the same way as regular AAV vectors (see below). The titration was done with real-time PCR.

Selection.

HVR.VIII went through one round of in vitro selection. Specifically, 1e9 genome copies (gc) of the AAV mutagenesis library was mixed with 0.5 μL of ADK8 (AAV8 Nab titer—1:2560) and added up to 1 mL with complete medium. The mixture was incubated at 37° C. for 30 min, and then applied to the 293 cells (MOI, ~1e4). Two days later, the cell was split followed by transfection with the plasmid pAdΔF6 and pRep two days later. Two days after the transfection, AAV fragments were retrieved from the cells by PCR, cloned into Topo vector (Invitrogen) for sequencing, and then cloned into trans plasmids to make AAV.CMV.eGFP vector for further analysis.

HVR.I and HVR.IV went through three rounds of in vivo selection in B6 mice, with a dose of 2.53e10 gc/mouse for HVR.I and 4e10 gc/mouse for HVRIV, 3 mice/group, i.v. injection. Two hours before library injection, 100 uL of hIVIG diluted with DPBS was injection intravenously. For round one, one group of mice was for each HVR, with hIVIG titer 1:40; for round two, two groups were for each HVR, with hIVIG titer 1:40 for group 1 and 1:80 for group 2; for round three, three groups were for each HVR, with hIVIG titer 1:80 for group 1, 1:160 for group 2 and 1:320 for group 3. Two weeks after vector injection, AAV sequences were retrieved from liver by PCR for next library construction described above. AAV vector production AAV vectors were made as described by Lock et al, 2010.

ELISA for canine F9 and human F9. The ELISA for measuring canine F9 was described by Wang et al., 2005. The human F9 ELISA protocol was a modified version of canine F9 ELISA, also developed by Wang et al.

In vitro Nab assay with eGFP as the reporter gene. 1e9 gc of each AAV mutant carrying eGFP cassette was mixed with different monoclonal antibodies (ADK8, AAV8 Nab titer 1:2560, 0.5 μL/well; ADK8/9, AAV8 Nab titer 1:2560, 0.5 μL/well; ADK9, AAV8 Nab titer 1:5, 0.5 μL/well), up to 100 μL with media, incubated at 37° C. for 30 minutes and then applied to 293 cells (5e4 cells/well seeded one day before infection in a 96-well plate). GFP expression was monitored and quantified with Image J. In vitro Nab assay with Luciferase as the reporter gene. Huh7 cells were seeded in 96-well black plates with clear bottom (Corning), 5e4 cells/well. Two days later, AAV vectors were diluted in complete medium and then mixed serum/plasma samples with various dilutions. The mixture was incubated at 37° C. for 30 minutes before transferred to the Huh7 plates. Three days after vector infection, luminescence was read with Clarity™ Luminescence Microplate Reader (BioTek).

Luciferase Assay, In Vivo

For studies with intranasal administration, mice were anaesthetized. D-luciferin (Xenogen) was instilled into the mouse nostril at 15 ug/uL, 10 uL/nostril, 20 uL/mouse. Five minutes later, luminescent images were taken by IVIS® Imaging Systems (Xenogen) and quantified with the software Living Image® 3.2. For other studies, mice were treated the same way except that D-luciferin was given i.p., 10 uL/gram of mouse body weight and that the luminescence was measured 20 minutes after luciferin injection.

Heparin Binding Assay

AAV vectors were diluted in desired buffers (DPBS or Tris buffer) and loaded to HiTrap Heparin HP column (GE Healthcare Life Sciences) by ÄKTA™ FPLC System (GE). The column was then washed sequentially with vector dilution buffer and dilution buffers plus increasing amount of sodium chloride. Fractions were collected during the whole process. Dot blot protocol was described by Tenney et al, 2014.

Another aspect of this study was replacing VP1/2 region (1-202) of AAV3G1 with h.20. By combining the data from Limberis et al.'s study (Limberis, M P et al, (2009). Transduction efficiencies of novel AAV vectors in mouse airway epithelium in vivo and human ciliated airway epithelium in vitro. Mol Ther 17: 294-301, which is incorporated herein by reference) and our sequence analysis, we found the codon 24 differentiation between high lung transduction members and low-lung transduction members within AAV clade E. Because the amino acids of the 1-202 region of the three highest Clade E member, rh.64R1, rh.10 and rh.20, are identical, we replaced this region into AAV3G1, leading to further improvement of AAV3G1's nasal transduction.

Example 4: Comparison of AAV8 and AAV3G1 in Muscle

Figure 15:
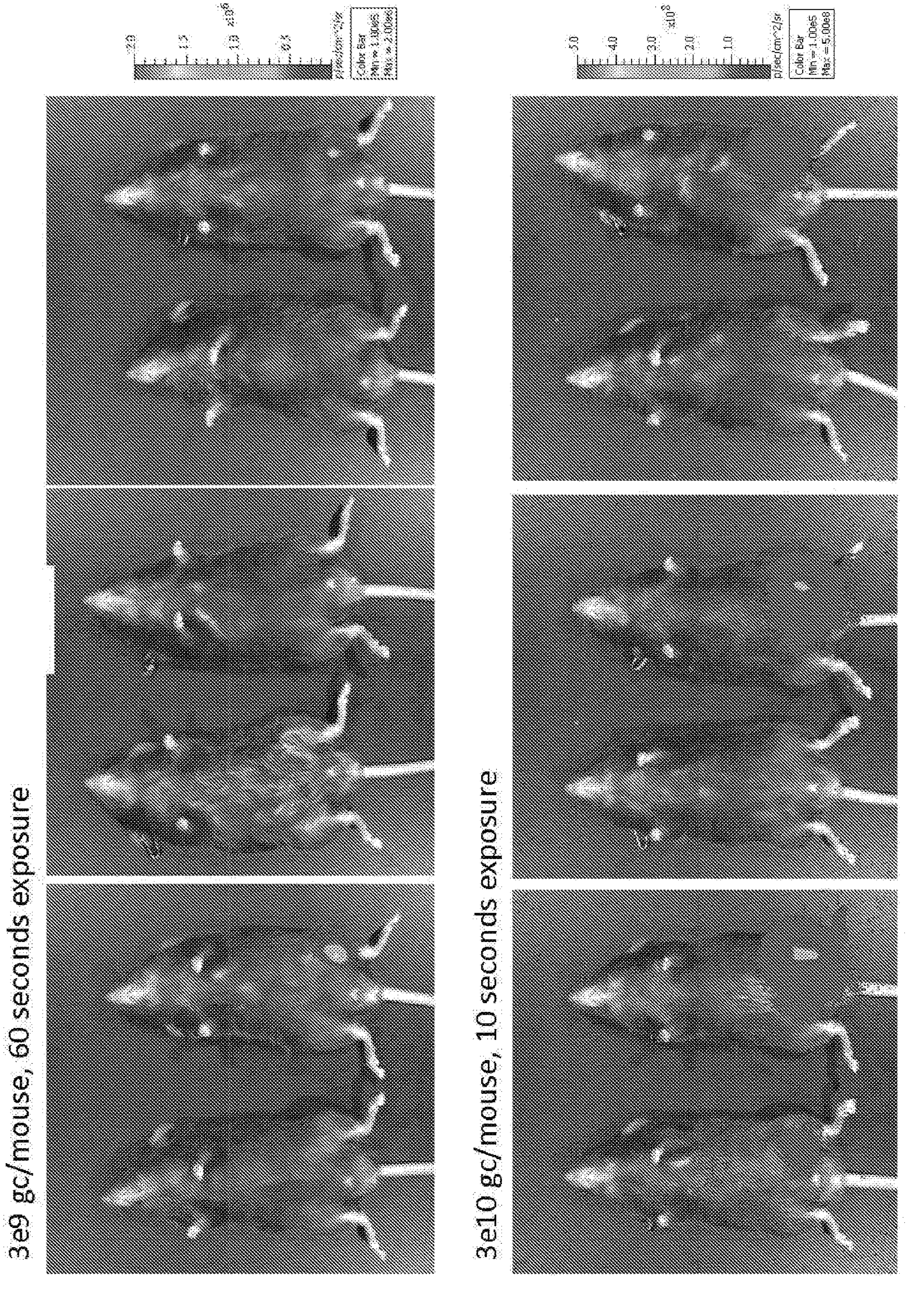
FIG. 15 are photographs of male B6 mice, 3 mice/group, injected i.m. with 3e9 or 3e10 gc/mouse, 1 leg/mouse with AAV3G.tMCK.PI.ffluc.bGH, dd-PCR(PK). Week 1 results are shown. For each figure, the left is AAV8-treated, the right AAV3G1.

Male B6 mice, 3 mice/group, were injected i.m. with 3e9 or 3e10 gc/mouse, 1 leg/mouse with AAV3G1.tMCK.PI.ffluc.bGH, dd-PCR(PK), manufactured and titrated by Vector Core. Week 1 results are shown in FIG. 15. For each figure, the left is AAV8-treated, the right AAV3G1.

Substantial proportion of AAV8 vectors went to liver even though the vectors were injected intramuscularly, consistent to previous studies, and the transgene was expressed in the liver even when controlled by the muscle-specific promoter tMCK. AAV3G1's muscle transduction is much better than AAV8.

Example 5

Neutralizing antibody titers were determined for AAV8, AV83G1 and AAV9 using serum from naïve NHPs. The results confirm that AAV8 and AAV3G1 are serologically distinct.

-continued

| | Animal | | AAV NAb in HEK293 cells[1,2] | | |
|---|---|---|---|---|---|
| # | ID | Time Point | AAV8 | AAV83G1 | AAV9 |
| 1 | RA2125 | Screening | <5 | <5 | <5 |
| 2 | RA2145 | Screening | <5 | <5 | <5 |
| 3 | RA2150 | Screening | <5 | <5 | <5 |
| 4 | RA2153 | Screening | 5* | <5 | <5 |
| 5 | RA2152 | Screening | <5 | <5 | <5 |
| 6 | RA2172 | Screening | <5 | 5* | 5* |
| 7 | RA2309 | Screening | 10* | <5 | <5 |
| 8 | RA2334 | Screening | <5 | <5 | <5 |
| 9 | RA2343 | Screening | <5 | <5 | <5 |
| 10 | RA1971 | Screening | <5 | <5 | <5 |
| 11 | RA0549 | Screening | <5 | <5 | <5 |
| 12 | RA1875 | Screening | <5 | <5 | <5 |
| 13 | RA0875 | Screening | <5 | <5 | <5 |
| 14 | RA1915 | Screening | <5 | <5 | <5 |
| 15 | RA1156 | Screening | <5 | <5 | <5 |
| 16 | BD957KB | Screening | <5 | <5 | <5 |
| 17 | RA0472 | Screening | 10* | <5 | <5 |
| 18 | RA0760 | Screening | >20* | 5* | 5* |

Sequence Listing Free Text

The following information is provided for sequences containing free text under numeric identifier <223>.

| SEQ ID NO: (containing free text) | Free text under <223> |
|---|---|
| 1 | <223> constructed sequence |
| 2 | <223> constructed sequence |
| 3 | <223> constructed sequence |
| 4 | <223> constructed sequence |
| 5 | <223> constructed sequence |
| 6 | <223> constructed sequence |
| 7 | <223> constructed sequence |
| 8 | <223> constructed sequence |
| 9 | <223> constructed sequence |
| 10 | <223> constructed sequence |
| 11 | <223> constructed sequence |
| 12 | <223> constructed sequence |
| 13 | <223> constructed sequence |
| 14 | <223> constructed sequence |
| 15 | <223> constructed sequence |
| 16 | <223> constructed sequence |
| 17 | <223> constructed sequence |
| 18 | <223> constructed sequence |
| 19 | <223> constructed sequence |
| 20 | <223> constructed sequence |
| 21 | <223> constructed sequence |
| 22 | <223> constructed sequence |
| 23 | <223> constructed sequence |
| 24 | <223> constructed sequence |
| 25 | <223> constructed sequence |
| 26 | <223> constructed sequence |
| 27 | <223> constructed sequence |
| 28 | <223> constructed sequence |
| 29 | <223> constructed sequence |
| 30 | <223> constructed sequence |
| 31 | <223> constructed sequence |
| 32 | <223> constructed sequence |
| 33 | <223> constructed sequence |
| 34 | <223> constructed sequence |
| 35 | <223> constructed sequence |
| 36 | <223> constructed sequence |
| 37 | <223> constructed sequence |
| 38 | <223> constructed sequence |
| 39 | <223> constructed sequence |
| 40 | <223> constructed sequence |
| 41 | <223> constructed sequence |
| 42 | <223> constructed sequence |
| 43 | <223> constructed sequence |
| 44 | <223> constructed sequence |
| 45 | <223> Constructed sequence |
| | <220> |
| | <221> misc_feature |
| | <222> (24) . . . (25) |
| | <223> n is a, c, g, or t |
| | <220> |
| | <221> misc_feature |
| | <222> (39) . . . (40) |
| | <223> n is a, c, g, or t |
| | <220> |
| | <221> misc_feature |
| | <222> (42) . . . (43) |
| | <223> n is a, c, g, or t |
| | <220> |
| | <221> misc_feature |
| | <222> (57) . . . (58) |
| | <223> n is a, c, g, or t |
| | <220> |
| | <221> misc_feature |
| | <222> (60) . . . (61) |
| | <223> n is a, c, g, or t |
| | <220> |
| | <221> misc_feature |
| | <222> (63) . . . (64) |
| | <223> n is a, c, g, or t |
| | <220> |
| | <221> misc_feature |
| | <222> (66) . . . (67) |
| | <223> n is a, c, g, or t |
| 46 | <223> Constructed sequence |
| 47 | <223> Constructed sequence |
| 48 | <223> Constructed sequence |
| 49 | <223> Constructed sequence |
| 50 | <223> Constructed sequence |
| 51 | <223> Constructed sequence |
| 52 | <223> Constructed sequence |
| 53 | <223> Constructed sequence |
| 54 | <223> Constructed sequence |
| 55 | <223> Constructed sequence |
| 56 | <223> constructed sequence |
| 57 | <223> Constructed sequence |
| | <220> |
| | <221> misc_feature |
| | <222> (26) . . . (27) |
| | <223> n is a, c, g, or t |
| | <220> |
| | <221> misc_feature |
| | <222> (29) . . . (30) |
| | <223> n is a, c, g, or t |
| | <220> |
| | <221> misc_feature |
| | <222> (32) . . . (33) |
| | <223> n is a, c, g, or t |
| | <220> |
| | <221> misc_feature |
| | <222> (35) . . . (36) |
| | <223> n is a, c, g, or t |
| | <220> |
| | <221> misc_feature |
| | <222> (38) . . . (39) |
| | <223> n is a, c, g, or t |
| 58 | <223> Constructed sequence |
| | <220> |
| | <221> misc_feature |
| | <222> (27) . . . (28) |
| | <223> n is a, c, g, or t |
| | <220> |
| | <221> misc_feature |
| | <222> (30) . . . (31) |
| | <223> n is a, c, g, or t |
| | <220> |
| | <221> misc_feature |
| | <222> (33) . . . (34) |
| | <223> n is a, c, g, or t |
| | <220> |
| | <221> misc_feature |
| | <222> (36) . . . (37) |
| | <223> n is a, c, g, or t |

-continued

| SEQ ID NO: (containing free text) | Free text under <223> |
|---|---|
| | <220> |
| | <221> misc_feature |
| | <222> (39) . . . (40) |
| | <223> n is a, c, g, or t |
| 59 | <223> Constructed sequence |
| | <220> |
| | <221> misc_feature |
| | <222> (26) . . . (27) |
| | <223> n is a, c, g, or t |
| | <220> |
| | <221> misc_feature |
| | <222> (29) . . . (30) |
| | <223> n is a, c, g, or t |
| | <220> |
| | <221> misc_feature |
| | <222> (32) . . . (33) |
| | <223> n is a, c, g, or t |
| | <220> |
| | <221> misc_feature |
| | <222> (35) . . . (36) |
| | <223> n is a, c, g, or t |
| | <220> |
| | <221> misc_feature |
| | <222> (38) . . . (39) |
| | <223> n is a, c, g, or t |
| 60 | <223> Constructed sequence |
| | <220> |
| | <221> misc_feature |
| | <222> (26) . . . (27) |
| | <223> n is a, c, g, or t |
| | <220> |
| | <221> misc_feature |
| | <222> (29) . . . (30) |
| | <223> n is a, c, g, or t |
| | <220> |
| | <221> misc_feature |
| | <222> (32) . . . (33) |
| | <223> n is a, c, g, or t |
| | <220> |
| | <221> misc_feature |
| | <222> (35) . . . (36) |
| | <223> n is a, c, g, or t |
| | <220> |
| | <221> misc_feature |
| | <222> (38) . . . (39) |
| | <223> n is a, c, g, or t |
| 61 | <223> Constructed sequence |
| | <220> |
| | <221> misc_feature |
| | <222> (26) . . . (27) |
| | <223> n is a, c, g, or t |
| | <220> |
| | <221> misc_feature |
| | <222> (29) . . . (30) |
| | <223> n is a, c, g, or t |
| | <220> |
| | <221> misc_feature |
| | <222> (32) . . . (33) |
| | <223> n is a, c, g, or t |
| | <220> |
| | <221> misc_feature |
| | <222> (35) . . . (36) |
| | <223> n is a, c, g, or t |
| | <220> |
| | <221> misc_feature |
| | <222> (38) . . . (39) |
| | <223> n is a, c, g, or t |
| 62 | <223> Constructed sequence |
| | <220> |
| | <221> misc_feature |
| | <222> (27) . . . (28) |
| | <223> n is a, c, g, or t |
| | <220> |
| | <221> misc_feature |
| | <222> (30) . . . (31) |
| | <223> n is a, c, g, or t |

-continued

| SEQ ID NO: (containing free text) | Free text under <223> |
|---|---|
| | <220> |
| | <221> misc_feature |
| | <222> (33) . . . (34) |
| | <223> n is a, c, g, or t |
| | <220> |
| | <221> misc_feature |
| | <222> (36) . . . (37) |
| | <223> n is a, c, g, or t |
| | <220> |
| | <221> misc_feature |
| | <222> (39) . . . (40) |
| | <223> n is a, c, g, or t |
| 63 | <223> Constructed sequence |
| 64 | <223> Constructed sequence |
| 65 | <223> Constructed sequence |
| 66 | <223> Constructed sequence |
| 67 | <223> Constructed sequence |
| 68 | <223> Constructed sequence |
| 69 | <223> major ADK8 epitope in AAV8 HVR.VIII region |
| 70 | <223> mutated c41 ADK8 epitope in AAV8 HVR.VIII region |
| 71 | <223> mutated c42 ADK8 epitope in AAV8 HVR.VIII region |
| 72 | <223> mutated c46 ADK8 epitope in AAV8 HVR.VIII region |
| 73 | <223> mutated g110 ADK8 epitope in AAV8 HVR.VIII region |
| 74 | <223> mutated g112 ADK8 epitope in AAV8 HVR.VIII region |
| 75 | <223> mutated g113 ADK8 epitope in AAV8 HVR.VIII region |
| 76 | <223> mutated g115 ADK8 epitope in AAV8 HVR.VIII region |
| 77 | <223> mutated g117 ADK8 epitope in AAV8 HVR.VIII region |
| 78 | <223> Constructed sequence |
| 79 | <223> Constructed sequence |
| 80 | <223> Constructed sequence |
| 81 | <223> Constructed sequence |
| 82 | <223> Constructed sequence |
| 83 | <223> Constructed sequence |
| 84 | <223> Constructed sequence |
| 85 | <223> Constructed sequence |
| | <220> |
| | <221> misc_feature |
| | <222> (24) . . . (25) |
| | <223> n is a, c, g, or t |
| | <220> |
| | <221> misc_feature |
| | <222> (39) . . . (40) |
| | <223> n is a, c, g, or t |
| | <220> |
| | <221> misc_feature |
| | <222> (42) . . . (43) |
| | <223> n is a, c, g, or t |
| | <220> |
| | <221> misc_feature |
| | <222> (57) . . . (58) |
| | <223> n is a, c, g, or t |
| | <220> |
| | <221> misc_feature |
| | <222> (60) . . . (61) |
| | <223> n is a, c, g, or t |
| | <220> |
| | <221> misc_feature |
| | <222> (63) . . . (64) |
| | <223> n is a, c, g, or t |
| | <220> |
| | <221> misc_feature |
| | <222> (66) . . . (67) |
| | <223> n is a, c, g, or t |
| 86 | <223> constructed sequence |
| | <220> |
| | <221> misc_feature |
| | <222> (26) . . . (27) |

-continued

| SEQ ID NO: (containing free text) | Free text under <223> |
| --- | --- |
| | <223> n is a, c, g, or t<br><220><br><221> misc_feature<br><222> (29) . . . (30)<br><223> n is a, c, g, or t<br><220><br><221> misc_feature<br><222> (32) . . . (33)<br><223> n is a, c, g, or t<br><220><br><221> misc_feature<br><222> (35) . . . (36)<br><223> n is a, c, g, or t<br><220><br><221> misc_feature<br><222> (38) . . . (39)<br><223> n is a, c, g, or t |
| 87 | <223> Constructed sequence<br><220><br><221> misc_feature<br><222> (26) . . . (27)<br><223> n is a, c, g, or t<br><220><br><221> misc_feature<br><222> (29) . . . (30)<br><223> n is a, c, g, or t<br><220> |

-continued

| SEQ ID NO: (containing free text) | Free text under <223> |
| --- | --- |
| | <221> misc_feature<br><222> (32) . . . (33)<br><223> n is a, c, g, or t<br><220><br><221> misc_feature<br><222> (35) . . . (36)<br><223> n is a, c, g, or t<br><220><br><221> misc_feature<br><222> (38) . . . (39)<br><223> n is a, c, g, or t |
| 88 | <223> AAV rh.20 capsid protein |

All publications cited in this specification are incorporated herein by reference in their entireties, as is U.S. Provisional Patent Application No. 62/323,389, filed Apr. 15, 2016. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

What is claimed is:

1. An adeno-associated virus (AAV) having a capsid comprising a vp3 capsid protein having at least the following mutations, as compared to native AAV8: N263S, S266H, T457S, A583G, Q588L, Q589Y, Q594G, I595S, G596V and T597F, wherein the native AAV8 is encoded by SEQ ID NO: 34 and wherein the capsid is encoded by SEQ ID NO: 17, SEQ ID NO: 19 or SEQ ID NO: 21, or a sequence sharing at least 80% identity therewith.

2. The AAV according to claim 1, wherein the N263S mutation comprises SEQ ID NO: 79 or SEQ ID NO: 80.

3. The AAV according to claim 1, wherein the T457S mutation comprises SEQ ID NO: 81.

4. The AAV according to claim 1, wherein the A583G mutation comprises SEQ ID NO: 70.

5. The AAV according to claim 1, wherein the vp3 capsid protein comprises mutations set forth in SEQ ID NO: 70 and SEQ ID NO: 79.

6. The AAV according to claim 1, wherein the vp3 capsid protein comprises mutations set forth in SEQ ID NO: 70, SEQ ID NO: 80 and SEQ ID NO: 82.

7. The AAV according to claim 4, wherein the capsid comprises vp1 and/or vp2 unique regions derived from a different AAV than the AAV supplying the vp3 unique region.

8. The AAV according to claim 7, wherein the AAV supplying the vp1 and vp2 sequences is rh.20.

9. A host cell transfected with an AAV according to claim 1.

10. A composition comprising at least an AAV according to claim 1 and a physiologically compatible carrier, buffer, adjuvant, and/or diluent.

11. A method of delivering a transgene to a cell, said method comprising the step of contacting the cell with an AAV according to claim 1, wherein said AAV comprises the transgene.

12. A nucleic acid encoding the vp3 capsid protein according to claim 1.

* * * * *

SEQUENCE LISTING

```
<160> NUMBER OF SEQ ID NOS: 88

<210> SEQ ID NO 1
<211> LENGTH: 2217
<212> TYPE: DNA
<213> ORGANISM: Artificial Sequence
<220> FEATURE:
<223> OTHER INFORMATION: constructed sequence

<400> SEQUENCE: 1

atggctgccg atggttatct tccagattgg ctcgaggaca acctctctga gggcattcgc      60

gagtggtggg cgctgaaacc tggagccccg aagcccaaag ccaaccagca aaagcaggac     120

gacggccggg gtctggtgct tcctggctac aagtacctcg gacccttcaa cggactcgac     180

aagggggagc ccgtcaacgc ggcggacgca gcggccctcg agcacgacaa ggcctacgac     240

cagcagctgc aggcgggtga caatccgtac ctgcggtata accacgccga cgccgagttt     300

caggagcgtc tgcaagaaga tacgtctttt gggggcaacc tcgggcgagc agtcttccag     360

gccaagaagc gggttctcga acctctcggt ctggttgagg aaggcgctaa gacggctcct     420

ggaaagaaga gaccggtaga gccatcaccc cagcgttctc cagactcctc tacgggcatc     480

ggcaagaaag gccaacagcc cgccagaaaa agactcaatt ttggtcagac tggcgactca     540

gagtcagttc cagaccctca acctctcgga gaacctccag cagcgccctc tggtgtggga     600

cctaatacaa tggctgcagg cggtggcgca ccaatggcag acaataacga aggcgccgac     660

ggagtgggta gttcctcggg aaattggcat tgcgattcca catggctggg cgacagagtc     720

atcaccacca gcacccgaac ctgggccctg cccacctaca acaaccacct ctacaagcaa     780

atctccaacg ggacatcggg aggagccacc aacgacaaca cctacttcgg ctacagcacc     840

ccctgggggt attttgactt taacagattc cactgccact tttcaccacg tgactggcag     900

cgactcatca acaacaactg gggattccgg cccaagagac tcagcttcaa gctcttcaac     960
```

-continued

```
atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgggtg ataacttgca gttgtataac acggctcctg gttcggtgtt tgtcaacagc   1800

caggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

```
<210> SEQ ID NO 2
<211> LENGTH: 738
<212> TYPE: PRT
<213> ORGANISM: Artificial Sequence
<220> FEATURE:
<223> OTHER INFORMATION: constructed sequence

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140
```

-continued

```
Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
```

```
                565                 570                 575

Glu Glu Tyr Gly Ile Val Gly Asp Asn Leu Gln Leu Tyr Asn Thr Ala
            580                 585                 590

Pro Gly Ser Val Phe Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 3
<211> LENGTH: 2217
<212> TYPE: DNA
<213> ORGANISM: Artificial Sequence
<220> FEATURE:
<223> OTHER INFORMATION: constructed sequence

<400> SEQUENCE: 3

atggctgccg atggttatct tccagattgg ctcgaggaca acctctctga gggcattcgc      60

gagtggtggg cgctgaaacc tggagccccg aagcccaaag ccaaccagca aaagcaggac     120

gacggccggg gtctggtgct tcctggctac aagtacctcg gacccttcaa cggactcgac     180

aagggggagc ccgtcaacgc ggcggacgca gcggccctcg agcacgacaa ggcctacgac     240

cagcagctgc aggcgggtga caatccgtac ctgcggtata accacgccga cgccgagttt     300

caggagcgtc tgcaagaaga tacgtctttt gggggcaacc tcgggcgagc agtcttccag     360

gccaagaagc gggttctcga acctctcggt ctggttgagg aaggcgctaa gacggctcct     420

ggaaagaaga gaccggtaga gccatcaccc cagcgttctc cagactcctc tacgggcatc     480

ggcaagaaag gccaacagcc cgccagaaaa agactcaatt ttggtcagac tggcgactca     540

gagtcagttc cagaccctca acctctcgga gaacctccag cagcgccctc tggtgtggga     600

cctaatacaa tggctgcagg cggtggcgca ccaatggcag acaataacga aggcgccgac     660

ggagtgggta gttcctcggg aaattggcat tgcgattcca catggctggg cgacagagtc     720

atcaccacca gcacccgaac ctgggccctg cccacctaca acaaccacct ctacaagcaa     780

atctccaacg ggacatcggg aggagccacc aacgacaaca cctacttcgg ctacagcacc     840

ccctgggggt attttgactt taacagattc cactgccact tttcaccacg tgactggcag     900

cgactcatca acaacaactg gggattccgg cccaagagac tcagcttcaa gctcttcaac     960

atccaggtca aggaggtcac gcagaatgaa ggcaccaaga ccatcgccaa taacctcacc    1020

agcaccatcc aggtgtttac ggactcggag taccagctgc cgtacgttct cggctctgcc    1080
```

```
caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgtctg ataacttgca gtttcgtaac acggctcctt tgtggtcttc tgtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

<210> SEQ ID NO 4
<211> LENGTH: 738
<212> TYPE: PRT
<213> ORGANISM: Artificial Sequence
<220> FEATURE:
<223> OTHER INFORMATION: constructed sequence

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

-continued

```
Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ser Asp Asn Leu Gln Phe Arg Asn Thr Ala
```

-continued

```
            580                 585                 590

Pro Leu Trp Ser Ser Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 5
<211> LENGTH: 2217
<212> TYPE: DNA
<213> ORGANISM: Artificial Sequence
<220> FEATURE:
<223> OTHER INFORMATION: constructed sequence

<400> SEQUENCE: 5

```
atggctgccg atggttatct tccagattgg ctcgaggaca acctctctga gggcattcgc      60

gagtggtggg cgctgaaacc tggagccccg aagcccaaag ccaaccagca aaagcaggac     120

gacggccggg gtctggtgct tcctggctac aagtacctcg gacccttcaa cggactcgac     180

aagggggagc ccgtcaacgc ggcggacgca gcggccctcg agcacgacaa ggcctacgac     240

cagcagctgc aggcgggtga caatccgtac ctgcggtata accacgccga cgccgagttt     300

caggagcgtc tgcaagaaga tacgtctttt gggggcaacc tcgggcgagc agtcttccag     360

gccaagaagc gggttctcga acctctcggt ctggttgagg aaggcgctaa gacggctcct     420

ggaaagaaga gaccggtaga gccatcaccc cagcgttctc cagactcctc tacgggcatc     480

ggcaagaaag gccaacagcc cgccagaaaa agactcaatt ttggtcagac tggcgactca     540

gagtcagttc cagaccctca acctctcgga gaacctccag cagcgccctc tggtgtggga     600

cctaatacaa tggctgcagg cggtggcgca ccaatggcag acaataacga aggcgccgac     660

ggagtgggta gttcctcggg aaattggcat tgcgattcca catggctggg cgacagagtc     720

atcaccacca gcacccgaac ctgggccctg cccacctaca acaaccacct ctacaagcaa     780

atctccaacg ggacatcggg aggagccacc aacgacaaca cctacttcgg ctacagcacc     840

ccctgggggt attttgactt taacagattc cactgccact tttcaccacg tgactggcag     900

cgactcatca acaacaactg gggattccgg cccaagagac tcagcttcaa gctcttcaac     960

atccaggtca aggaggtcac gcagaatgaa ggcaccaaga ccatcgccaa taacctcacc    1020

agcaccatcc aggtgtttac ggactcggag taccagctgc cgtacgttct cggctctgcc    1080

caccagggct gcctgcctcc gttcccggcg gacgtgttca tgattcccca gtacggctac    1140
```

-continued

```
ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgaatg ataacttgca ggtttgtaac acggctcctg atgatgttat ggtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

<210> SEQ ID NO 6
<211> LENGTH: 738
<212> TYPE: PRT
<213> ORGANISM: Artificial Sequence
<220> FEATURE:
<223> OTHER INFORMATION: constructed sequence

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175
```

-continued

```
Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Asn Asp Asn Leu Gln Val Cys Asn Thr Ala
            580                 585                 590

Pro Asp Asp Val Met Val Asn Ser Gln Gly Ala Leu Pro Gly Met Val
```

-continued

```
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 7
<211> LENGTH: 2217
<212> TYPE: DNA
<213> ORGANISM: Artificial Sequence
<220> FEATURE:
<223> OTHER INFORMATION: constructed sequence

<400> SEQUENCE: 7

atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900

cgactcatca acaacaactg gggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260
```

```
gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgtgtg ataacttgca gggttataac acggctcctc tgtgtgttgc tgtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

```
<210> SEQ ID NO 8
<211> LENGTH: 738
<212> TYPE: PRT
<213> ORGANISM: Artificial Sequence
<220> FEATURE:
<223> OTHER INFORMATION: constructed sequence

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190
```

-continued

```
Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Cys Asp Asn Leu Gln Gly Tyr Asn Thr Ala
            580                 585                 590

Pro Leu Cys Val Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
```

```
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 9
<211> LENGTH: 2217
<212> TYPE: DNA
<213> ORGANISM: Artificial Sequence
<220> FEATURE:
<223> OTHER INFORMATION: constructed sequence

<400> SEQUENCE: 9

atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900

cgactcatca acaacaactg gggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320
```

-continued

```
attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtggttg ataacttgca gtttcttaac acggctcctg ctggtgaggc ggtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaacccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

```
<210> SEQ ID NO 10
<211> LENGTH: 738
<212> TYPE: PRT
<213> ORGANISM: Artificial Sequence
<220> FEATURE:
<223> OTHER INFORMATION: constructed sequence

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205
```

-continued

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Val Asp Asn Leu Gln Phe Leu Asn Thr Ala
            580                 585                 590

Pro Ala Gly Glu Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
```

```
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 11
<211> LENGTH: 2217
<212> TYPE: DNA
<213> ORGANISM: Artificial Sequence
<220> FEATURE:
<223> OTHER INFORMATION: constructed sequence

<400> SEQUENCE: 11

atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900

cgactcatca acaacaactg gggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440
```

```
ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgcttg ataacttgca ggatggtaac acggctcctg gtgcgtgtgg tgtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

```
<210> SEQ ID NO 12
<211> LENGTH: 738
<212> TYPE: PRT
<213> ORGANISM: Artificial Sequence
<220> FEATURE:
<223> OTHER INFORMATION: constructed sequence

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220
```

-continued

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Leu Asp Asn Leu Gln Asp Gly Asn Thr Ala
            580                 585                 590

Pro Gly Ala Cys Gly Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
```

645 650 655

Pro Ala Asp Pro Pro Thr Thr Phe Asn Gln Ser Lys Leu Asn Ser Phe
660 665 670

Ile Thr Gln Tyr Ser Thr Gly Gln Val Ser Val Glu Ile Glu Trp Glu
675 680 685

Leu Gln Lys Glu Asn Ser Lys Arg Trp Asn Pro Glu Ile Gln Tyr Thr
690 695 700

Ser Asn Tyr Tyr Lys Ser Thr Ser Val Asp Phe Ala Val Asn Thr Glu
705 710 715 720

Gly Val Tyr Ser Glu Pro Arg Pro Ile Gly Thr Arg Tyr Leu Thr Arg
725 730 735

Asn Leu

<210> SEQ ID NO 13
<211> LENGTH: 2217
<212> TYPE: DNA
<213> ORGANISM: Artificial Sequence
<220> FEATURE:
<223> OTHER INFORMATION: constructed sequence

<400> SEQUENCE: 13
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttgtctcgg actcaaacaa caggaggcac ggcaaatacg 1380
cagactctgg gcttcagcca aggtgggcct aatacaatgg ccaatcaggc aaagaactgg 1440
ctgccaggac cctgttaccg ccaacaacgc gtctcaacga caaccgggca aaacaacaat 1500

```
agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgtggg ataacttgca gtctgagaac acggctcctt cggagacttc tgtcaacagc   1800

cagggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

<210> SEQ ID NO 14
<211> LENGTH: 738
<212> TYPE: PRT
<213> ORGANISM: Artificial Sequence
<220> FEATURE:
<223> OTHER INFORMATION: constructed sequence

<400> SEQUENCE: 14

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240
```

-continued

```
Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Trp Asp Asn Leu Gln Ser Glu Asn Thr Ala
            580                 585                 590

Pro Ser Glu Thr Ser Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
```

```
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 15
<211> LENGTH: 2217
<212> TYPE: DNA
<213> ORGANISM: Artificial Sequence
<220> FEATURE:
<223> OTHER INFORMATION: constructed sequence

<400> SEQUENCE: 15

atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900

cgactcatca acaacaactg gggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620
```

-continued

```
gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtgtctg ataacttgca gtcttgtaac acggctcctt ttgcgggtgc ggtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

<210> SEQ ID NO 16
<211> LENGTH: 738
<212> TYPE: PRT
<213> ORGANISM: Artificial Sequence
<220> FEATURE:
<223> OTHER INFORMATION: constructed sequence

<400> SEQUENCE: 16

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

-continued

```
Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ser Asp Asn Leu Gln Ser Cys Asn Thr Ala
            580                 585                 590

Pro Phe Ala Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
```

-continued

```
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 17
<211> LENGTH: 2214
<212> TYPE: DNA
<213> ORGANISM: Artificial Sequence
<220> FEATURE:
<223> OTHER INFORMATION: constructed sequence

<400> SEQUENCE: 17

atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctcctctg gtactcatgg agccaccaac gacaacacct acttcggcta cagcaccccc    840

tgggggtatt ttgactttaa cagattccac tgccactttt caccacgtga ctggcagcga    900

ctcatcaaca acaactgggg attccggccc aagagactca gcttcaagct cttcaacatc    960

caggtcaagg aggtcacgca gaatgaaggc accaagacca tcgccaataa cctcaccagc   1020

accatccagg tgtttacgga ctcggagtac cagctgccgt acgttctcgg ctctgcccac   1080

cagggctgcc tgcctccgtt cccggcggac gtgttcatga ttccccagta cggctaccta   1140

acactcaaca acggtagtca ggccgtggga cgctcctcct tctactgcct ggaatacttt   1200

ccttcgcaga tgctgagaac cggcaacaac ttccagttta cttacacctt cgaggacgtg   1260

cctttccaca gcagctacgc ccacagccag agcttggacc ggctgatgaa tcctctgatt   1320

gaccagtacc tgtactactt gtctcggact caaacaacag gtgggagtag gcctacgcag   1380

actctgggct tcagccaagg tgggcctaat acaatggcca atcaggcaaa gaactggctg   1440

ccaggaccct gttaccgcca acaacgcgtc tcaacgacaa ccgggcaaaa caacaatagc   1500

aactttgcct ggactgctgg gaccaaatac catctgaatg gaagaaattc attggctaat   1560

cctggcatcg ctatggcaac acacaaagac gacgaggagc gtttttttcc cagtaacggg   1620

atcctgattt ttggcaaaca aaatgctgcc agagacaatg cggattacag cgatgtcatg   1680
```

-continued

```
ctcaccagcg aggaagaaat caaaaccact aaccctgtgg ctacagagga atacggtatc   1740

gtgggtgata acttgcagtt gtataacacg gctcctggtt cggtgtttgt caacagccag   1800

ggggccttac ccggtatggt ctggcagaac cgggacgtgt acctgcaggg tcccatctgg   1860

gccaagattc ctcacacgga cggcaacttc cacccgtctc cgctgatggg cggctttggc   1920

ctgaaacatc ctccgcctca gatcctgatc aagaacacgc ctgtacctgc ggatcctccg   1980

accaccttca accagtcaaa gctgaactct ttcatcacgc aatacagcac cggacaggtc   2040

agcgtggaaa ttgaatggga gctgcagaag gaaaacagca agcgctggaa ccccgagatc   2100

cagtacacct ccaactacta caaatctaca agtgtggact ttgctgttaa tacagaaggc   2160

gtgtactctg aaccccgccc cattggcacc cgttacctca cccgtaatct gtaa         2214
```

<210> SEQ ID NO 18
<211> LENGTH: 737
<212> TYPE: PRT
<213> ORGANISM: Artificial Sequence
<220> FEATURE:
<223> OTHER INFORMATION: constructed sequence

<400> SEQUENCE: 18

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gly Thr His Gly Ala Thr Asn Asp Asn
            260                 265                 270
```

-continued

```
Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Ser Arg Pro Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Gly Asp Asn Leu Gln Leu Tyr Asn Thr Ala Pro
            580                 585                 590

Gly Ser Val Phe Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
```

```
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu


<210> SEQ ID NO 19
<211> LENGTH: 2214
<212> TYPE: DNA
<213> ORGANISM: Artificial Sequence
<220> FEATURE:
<223> OTHER INFORMATION: constructed sequence

<400> SEQUENCE: 19

atggctgccg atggttatct tccagattgg ctcgaggaca acctctctga gggcattcgc     60

gagtggtggg acttgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagacag gccagcagcc cgcgaaaaag agactcaact ttgggcagac tggcgactca    540

gagtcagtgc ccgaccctca accaatcgga gaacccccg caggcccctc tggtctggga    600

tctggtacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctcctctg gtactcatgg agccaccaac gacaacacct acttcggcta cagcaccccc    840

tgggggtatt ttgactttaa cagattccac tgccactttt caccacgtga ctggcagcga    900

ctcatcaaca acaactgggg attccggccc aagagactca gcttcaagct cttcaacatc    960

caggtcaagg aggtcacgca gaatgaaggc accaagacca tcgccaataa cctcaccagc   1020

accatccagg tgtttacgga ctcggagtac cagctgccgt acgttctcgg ctctgcccac   1080

cagggctgcc tgcctccgtt cccggcggac gtgttcatga ttccccagta cggctaccta   1140

acactcaaca acggtagtca ggccgtggga cgctcctcct tctactgcct ggaatacttt   1200

ccttcgcaga tgctgagaac cggcaacaac ttccagttta cttacacctt cgaggacgtg   1260

cctttccaca gcagctacgc ccacagccag agcttggacc ggctgatgaa tcctctgatt   1320

gaccagtacc tgtactactt gtctcggact caaacaacag gtgggagtag gcctacgcag   1380

actctgggct tcagccaagg tgggcctaat acaatggcca atcaggcaaa gaactggctg   1440

ccaggaccct gttaccgcca acaacgcgtc tcaacgacaa ccgggcaaaa caacaatagc   1500

aactttgcct ggactgctgg gaccaaatac catctgaatg gaagaaattc attggctaat   1560

cctggcatcg ctatggcaac acacaaagac gacgaggagc gtttttttcc cagtaacggg   1620

atcctgattt ttggcaaaca aaatgctgcc agagacaatg cggattacag cgatgtcatg   1680

ctcaccagcg aggaagaaat caaaaccact aaccctgtgg ctacagagga atacggtatc   1740

gtgggtgata acttgcagtt gtataacacg gctcctggtt cggtgtttgt caacagccag   1800
```

```
ggggccttac ccggtatggt ctggcagaac cgggacgtgt acctgcaggg tcccatctgg   1860

gccaagattc ctcacacgga cggcaacttc cacccgtctc cgctgatggg cggctttggc   1920

ctgaaacatc ctccgcctca gatcctgatc aagaacacgc ctgtacctgc ggatcctccg   1980

accaccttca accagtcaaa gctgaactct ttcatcacgc aatacagcac cggacaggtc   2040

agcgtggaaa ttgaatggga gctgcagaag gaaaacagca agcgctggaa ccccgagatc   2100

cagtacacct ccaactacta caaatctaca agtgtggact ttgctgttaa tacagaaggc   2160

gtgtactctg aaccccgccc cattggcacc cgttacctca cccgtaatct gtaa         2214
```

<210> SEQ ID NO 20
<211> LENGTH: 737
<212> TYPE: PRT
<213> ORGANISM: Artificial Sequence
<220> FEATURE:
<223> OTHER INFORMATION: constructed sequence

<400> SEQUENCE: 20

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gly Thr His Gly Ala Thr Asn Asp Asn
            260                 265                 270

Thr Tyr Phe Gly Tyr Ser Thr Pro Trp Gly Tyr Phe Asp Phe Asn Arg
        275                 280                 285
```

-continued

```
Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Ser Arg Pro Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Gly Asp Asn Leu Gln Leu Tyr Asn Thr Ala Pro
            580                 585                 590

Gly Ser Val Phe Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
```

705 710 715 720

Val Tyr Ser Glu Pro Arg Pro Ile Gly Thr Arg Tyr Leu Thr Arg Asn
725 730 735

Leu

<210> SEQ ID NO 21
<211> LENGTH: 2214
<212> TYPE: DNA
<213> ORGANISM: Artificial Sequence
<220> FEATURE:
<223> OTHER INFORMATION: constructed sequence

<400> SEQUENCE: 21
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctcctctg atactcatgg agccaccaac gacaacacct acttcggcta cagcaccccc 840
tgggggtatt ttgactttaa cagattccac tgccactttt caccacgtga ctggcagcga 900
ctcatcaaca acaactgggg attccggccc aagagactca gcttcaagct cttcaacatc 960
caggtcaagg aggtcacgca gaatgaaggc accaagacca tcgccaataa cctcaccagc 1020
accatccagg tgtttacgga ctcggagtac cagctgccgt acgttctcgg ctctgcccac 1080
cagggctgcc tgcctccgtt cccggcggac gtgttcatga ttccccagta cggctaccta 1140
acactcaaca acggtagtca ggccgtggga cgctcctcct tctactgcct ggaatacttt 1200
ccttcgcaga tgctgagaac cggcaacaac ttccagttta cttacacctt cgaggacgtg 1260
cctttccaca gcagctacgc ccacagccag agcttggacc ggctgatgaa tcctctgatt 1320
gaccagtacc tgtactactt gtctcggact caaacaacag atgggtctgg gctgacgcag 1380
actctgggct tcagccaagg tgggcctaat acaatggcca atcaggcaaa gaactggctg 1440
ccaggaccct gttaccgcca acaacgcgtc tcaacgacaa ccgggcaaaa caacaatagc 1500
aactttgcct ggactgctgg gaccaaatac catctgaatg gaagaaattc attggctaat 1560
cctggcatcg ctatggcaac acacaaagac gacgaggagc gttttttttcc cagtaacggg 1620 atcctgattt ttggcaaaca aaatgctgcc agagacaatg cggattacag cgatgtcatg 1680
ctcaccagcg aggaagaaat caaaaccact aaccctgtgg ctacagagga atacggtatc 1740
gtgggtgata acttgcagtt gtataacacg gctcctggtt cggtgtttgt caacagccag 1800
ggggccttac ccggtatggt ctggcagaac cgggacgtgt acctgcaggg tcccatctgg 1860

```
gccaagattc ctcacacgga cggcaacttc cacccgtctc cgctgatggg cggctttggc   1920

ctgaaacatc ctccgcctca gatcctgatc aagaacacgc ctgtacctgc ggatcctccg   1980

accaccttca accagtcaaa gctgaactct ttcatcacgc aatacagcac cggacaggtc   2040

agcgtggaaa ttgaatggga gctgcagaag gaaaacagca agcgctggaa ccccgagatc   2100

cagtacacct ccaactacta caaatctaca agtgtggact ttgctgttaa tacagaaggc   2160

gtgtactctg aaccccgccc cattggcacc cgttacctca cccgtaatct gtaa         2214
```

<210> SEQ ID NO 22
<211> LENGTH: 737
<212> TYPE: PRT
<213> ORGANISM: Artificial Sequence
<220> FEATURE:
<223> OTHER INFORMATION: constructed sequence

<400> SEQUENCE: 22

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Asp Thr His Gly Ala Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

-continued

```
Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Asp Gly Ser Gly Leu Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Gly Asp Asn Leu Gln Leu Tyr Asn Thr Ala Pro
            580                 585                 590

Gly Ser Val Phe Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
```

-continued 725 730 735

Leu

<210> SEQ ID NO 23
<211> LENGTH: 2214
<212> TYPE: DNA
<213> ORGANISM: Artificial Sequence
<220> FEATURE:
<223> OTHER INFORMATION: constructed sequence

<400> SEQUENCE: 23
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctcctctg gtactcatgg agccaccaac gacaacacct acttcggcta cagcaccccc 840
tgggggtatt ttgactttaa cagattccac tgccactttt caccacgtga ctggcagcga 900
ctcatcaaca acaactgggg attccggccc aagagactca gcttcaagct cttcaacatc 960
caggtcaagg aggtcacgca gaatgaaggc accaagacca tcgccaataa cctcaccagc 1020
accatccagg tgtttacgga ctcggagtac cagctgccgt acgttctcgg ctctgcccac 1080
cagggctgcc tgcctccgtt cccggcggac gtgttcatga ttccccagta cggctaccta 1140
acactcaaca acggtagtca ggccgtggga cgctcctcct tctactgcct ggaatacttt 1200
ccttcgcaga tgctgagaac cggcaacaac ttccagttta cttacacctt cgaggacgtg 1260
cctttccaca gcagctacgc ccacagccag agcttggacc ggctgatgaa tcctctgatt 1320
gaccagtacc tgtactactt gtctcggact caaacaacag gtgggagtag gcctacgcag 1380
actctgggct tcagccaagg tggccctaat acaatggcca atcaggcaaa gaactggctg 1440
ccaggaccct gttaccgcca acaacgcgtc tcaacgacaa ccgggcaaaa caacaatagc 1500
aactttgcct ggactgctgg gaccaaatac catctgaatg gaagaaattc attggctaat 1560
cctggcatcg ctatggcaac acacaaagac gacgaggagc gtttttttcc cagtaacggg 1620
atcctgattt ttggcaaaca aaatgctgcc agagacaatg cggattacag cgatgtcatg 1680
ctcaccagcg aggaagaaat caaaaccact aaccctgtgg ctacagagga atacggtatc 1740
gtggcagata acttgcagca gcaaaacacg gctcctcaaa ttggaactgt caacagccag 1800
ggggccttac ccggtatggt ctggcagaac cgggacgtgt acctgcaggg tcccatctgg 1860
gccaagattc ctcacacgga cggcaacttc cacccgtctc cgctgatggg cggctttggc 1920
ctgaaacatc ctccgcctca gatcctgatc aagaacacgc ctgtacctgc ggatcctccg 1980

-continued accaccttca accagtcaaa gctgaactct ttcatcacgc aatacagcac cggacaggtc 2040
agcgtggaaa ttgaatggga gctgcagaag gaaaacagca agcgctggaa ccccgagatc 2100
cagtacacct ccaactacta caaatctaca agtgtggact ttgctgttaa tacagaaggc 2160
gtgtactctg aaccccgccc cattggcacc cgttacctca cccgtaatct gtaa 2214

<210> SEQ ID NO 24
<211> LENGTH: 737
<212> TYPE: PRT
<213> ORGANISM: Artificial Sequence
<220> FEATURE:
<223> OTHER INFORMATION: constructed sequence

<400> SEQUENCE: 24

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Ser Gly Thr His Gly Ala Thr Asn Asp Asn
260 265 270

Thr Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Ser Phe Lys Leu Phe Asn Ile
305 310 315 320

-continued

```
Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Ser Arg Pro Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Ala Asp Asn Leu Gln Gln Gln Asn Thr Ala Pro
            580                 585                 590

Gln Ile Gly Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 25
<211> LENGTH: 2214
<212> TYPE: DNA
<213> ORGANISM: Artificial Sequence
<220> FEATURE:
<223> OTHER INFORMATION: constructed sequence

<400> SEQUENCE: 25
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctcctctg gtactcatgg agccaccaac gacaacacct acttcggcta cagcaccccc 840
tgggggtatt ttgactttaa cagattccac tgccactttt caccacgtga ctggcagcga 900
ctcatcaaca acaactgggg attccggccc aagagactca gcttcaagct cttcaacatc 960
caggtcaagg aggtcacgca gaatgaaggc accaagacca tcgccaataa cctcaccagc 1020
accatccagg tgtttacgga ctcggagtac cagctgccgt acgttctcgg ctctgcccac 1080
cagggctgcc tgcctccgtt cccggcggac gtgttcatga ttccccagta cggctaccta 1140
acactcaaca acggtagtca ggccgtggga cgctcctcct tctactgcct ggaatacttt 1200
ccttcgcaga tgctgagaac cggcaacaac ttccagttta cttacacctt cgaggacgtg 1260
cctttccaca gcagctacgc ccacagccag agcttggacc ggctgatgaa tcctctgatt 1320
gaccagtacc tgtactactt gtctcggact caaacaacag gaggcacggc aaatacgcag 1380
actctgggct tcagccaagg tggccctaat acaatggcca atcaggcaaa gaactggctg 1440
ccaggaccct gttaccgcca acaacgcgtc tcaacgacaa ccgggcaaaa caacaatagc 1500
aactttgcct ggactgctgg gaccaaatac catctgaatg gaagaaattc attggctaat 1560
cctggcatcg ctatggcaac acacaaagac gacgaggagc gtttttttcc cagtaacggg 1620
atcctgattt ttggcaaaca aaatgctgcc agagacaatg cggattacag cgatgtcatg 1680
ctcaccagcg aggaagaaat caaaaccact aaccctgtgg ctacagagga atacggtatc 1740
gtgggtgata acttgcagtt gtataacacg gctcctggtt cggtgtttgt caacagccag 1800
ggggccttac ccggtatggt ctggcagaac cgggacgtgt acctgcaggg tcccatctgg 1860
gccaagattc ctcacacgga cggcaacttc cacccgtctc cgctgatggg cggctttggc 1920
ctgaaacatc ctccgcctca gatcctgatc aagaacacgc ctgtacctgc ggatcctccg 1980
accaccttca accagtcaaa gctgaactct ttcatcacgc aatacagcac cggacaggtc 2040

```
agcgtggaaa ttgaatggga gctgcagaag gaaaacagca agcgctggaa ccccgagatc   2100

cagtacacct ccaactacta caaatctaca agtgtggact ttgctgttaa tacagaaggc   2160

gtgtactctg aacccgccc cattggcacc cgttacctca cccgtaatct gtaa          2214
```

<210> SEQ ID NO 26
<211> LENGTH: 737
<212> TYPE: PRT
<213> ORGANISM: Artificial Sequence
<220> FEATURE:
<223> OTHER INFORMATION: constructed sequence

<400> SEQUENCE: 26

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gly Thr His Gly Ala Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335
```

```
Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Gly Asp Asn Leu Gln Leu Tyr Asn Thr Ala Pro
            580                 585                 590

Gly Ser Val Phe Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 27

<211> LENGTH: 2214
<212> TYPE: DNA
<213> ORGANISM: Artificial Sequence
<220> FEATURE:
<223> OTHER INFORMATION: constructed sequence

<400> SEQUENCE: 27
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctcctctg gtactcatgg agccaccaac gacaacacct acttcggcta cagcaccccc 840
tgggggtatt ttgactttaa cagattccac tgccactttt caccacgtga ctggcagcga 900
ctcatcaaca acaactgggg attccggccc aagagactca gcttcaagct cttcaacatc 960
caggtcaagg aggtcacgca gaatgaaggc accaagacca tcgccaataa cctcaccagc 1020
accatccagg tgtttacgga ctcggagtac cagctgccgt acgttctcgg ctctgcccac 1080
cagggctgcc tgcctccgtt cccggcggac gtgttcatga ttccccagta cggctaccta 1140
acactcaaca acggtagtca ggccgtggga cgctcctcct tctactgcct ggaatacttt 1200
ccttcgcaga tgctgagaac cggcaacaac ttccagttta cttacacctt cgaggacgtg 1260
cctttccaca gcagctacgc ccacagccag agcttggacc ggctgatgaa tcctctgatt 1320
gaccagtacc tgtactactt gtctcggact caaacaacag gaggcacggc aaatacgcag 1380
actctgggct tcagccaagg tgggcctaat acaatggcca atcaggcaaa gaactggctg 1440
ccaggaccct gttaccgcca acaacgcgtc tcaacgacaa ccgggcaaaa caacaatagc 1500
aactttgcct ggactgctgg gaccaaatac catctgaatg gaagaaattc attggctaat 1560
cctggcatcg ctatggcaac acacaaagac gacgaggagc gtttttttcc cagtaacggg 1620
atcctgattt ttggcaaaca aaatgctgcc agagacaatg cggattacag cgatgtcatg 1680
ctcaccagcg aggaagaaat caaaaccact aaccctgtgg ctacagagga atacggtatc 1740
gtggcagata acttgcagca gcaaaacacg gctcctcaaa ttggaactgt caacagccag 1800
ggggccttac ccggtatggt ctggcagaac cgggacgtgt acctgcaggg tcccatctgg 1860
gccaagattc ctcacacgga cggcaacttc cacccgtctc cgctgatggg cggctttggc 1920
ctgaaacatc ctccgcctca gatcctgatc aagaacacgc ctgtacctgc ggatcctccg 1980
accaccttca accagtcaaa gctgaactct ttcatcacgc aatacagcac cggacaggtc 2040
agcgtggaaa ttgaatggga gctgcagaag gaaaacagca agcgctggaa ccccgagatc 2100
cagtacacct ccaactacta caaatctaca agtgtggact ttgctgttaa tacagaaggc 2160
gtgtactctg aaccccgccc cattggcacc cgttacctca cccgtaatct gtaa 2214

<210> SEQ ID NO 28
<211> LENGTH: 737
<212> TYPE: PRT
<213> ORGANISM: Artificial Sequence
<220> FEATURE:
<223> OTHER INFORMATION: constructed sequence

<400> SEQUENCE: 28

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Ser Gly Thr His Gly Ala Thr Asn Asp Asn
260 265 270

Thr Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Ser Phe Lys Leu Phe Asn Ile
305 310 315 320

Gln Val Lys Glu Val Thr Gln Asn Glu Gly Thr Lys Thr Ile Ala Asn
325 330 335

Asn Leu Thr Ser Thr Ile Gln Val Phe Thr Asp Ser Glu Tyr Gln Leu
340 345 350

```
Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Ala Asp Asn Leu Gln Gln Gln Asn Thr Ala Pro
            580                 585                 590

Gln Ile Gly Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 29
<211> LENGTH: 2217
<212> TYPE: DNA
<213> ORGANISM: Artificial Sequence
<220> FEATURE:
<223> OTHER INFORMATION: constructed sequence

<400> SEQUENCE: 29
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttgtctcgg actcaaacaa caggtgggag taggcctacg 1380
cagactctgg gcttcagcca aggtgggcct aatacaatgg ccaatcaggc aaagaactgg 1440
ctgccaggac cctgttaccg ccaacaacgc gtctcaacga caaccgggca aaacaacaat 1500
agcaactttg cctggactgc tgggaccaaa taccatctga atggaagaaa ttcattggct 1560
aatcctggca tcgctatggc aacacacaaa gacgacgagg agcgtttttt tcccagtaac 1620
gggatcctga tttttggcaa acaaaatgct gccagagaca atgcggatta cagcgatgtc 1680
atgctcacca gcgaggaaga aatcaaaacc actaaccctg tggctacaga ggaatacggt 1740
atcgtggcag ataacttgca gcagcaaaac acggctcctc aaattggaac tgtcaacagc 1800 caggggggcct tacccggtat ggtctggcag aaccgggacg tgtacctgca gggtcccatc 1860
tgggccaaga ttcctcacac ggacggcaac ttccacccgt ctccgctgat gggcggcttt 1920
ggcctgaaac atcctccgcc tcagatcctg atcaagaaca cgcctgtacc tgcggatcct 1980
ccgaccacct tcaaccagtc aaagctgaac tctttcatca cgcaatacag caccggacag 2040
gtcagcgtgg aaattgaatg ggagctgcag aaggaaaaca gcaagcgctg gaaccccgag 2100
atccagtaca cctccaacta ctacaaatct acaagtgtgg actttgctgt taatacagaa 2160
ggcgtgtact ctgaaccccg ccccattggc acccgttacc tcacccgtaa tctgtaa 2217

<210> SEQ ID NO 30
<211> LENGTH: 738
<212> TYPE: PRT
<213> ORGANISM: Artificial Sequence
<220> FEATURE:
<223> OTHER INFORMATION: constructed sequence

<400> SEQUENCE: 30

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365
```

-continued

```
Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Ser Arg Pro Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 31
<211> LENGTH: 2217
<212> TYPE: DNA
<213> ORGANISM: Artificial Sequence
<220> FEATURE:
<223> OTHER INFORMATION: constructed sequence

<400> SEQUENCE: 31
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttgtctcgg actcaaacaa caggtgggag taggcctacg 1380
cagactctgg gcttcagcca aggtgggcct aatacaatgg ccaatcaggc aaagaactgg 1440
ctgccaggac cctgttaccg ccaacaacgc gtctcaacga caaccgggca aaacaacaat 1500
agcaactttg cctggactgc tgggaccaaa taccatctga atggaagaaa ttcattggct 1560
aatcctggca tcgctatggc aacacacaaa gacgacgagg agcgtttttt tcccagtaac 1620
gggatcctga tttttggcaa acaaaatgct gccagagaca atgcggatta cagcgatgtc 1680
atgctcacca gcgaggaaga aatcaaaacc actaaccctg tggctacaga ggaatacggt 1740
atcgtgggtg ataacttgca gttgtataac acggctcctg gttcggtgtt tgtcaacagc 1800 caggggggcct tacccggtat ggtctggcag aaccgggacg tgtacctgca gggtcccatc 1860
tgggccaaga ttcctcacac ggacggcaac ttccacccgt ctccgctgat gggcggcttt 1920
ggcctgaaac atcctccgcc tcagatcctg atcaagaaca cgcctgtacc tgcggatcct 1980
ccgaccacct tcaaccagtc aaagctgaac tctttcatca cgcaatacag caccggacag 2040
gtcagcgtgg aaattgaatg ggagctgcag aaggaaaaca gcaagcgctg gaaccccgag 2100
atccagtaca cctccaacta ctacaaatct acaagtgtgg actttgctgt taatacagaa 2160
ggcgtgtact ctgaaccccg ccccattggc acccgttacc tcacccgtaa tctgtaa 2217

<210> SEQ ID NO 32
<211> LENGTH: 738

<212> TYPE: PRT
<213> ORGANISM: Artificial Sequence
<220> FEATURE:
<223> OTHER INFORMATION: constructed sequence

<400> SEQUENCE: 32

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380
```

```
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Ser Arg Pro Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Gly Asp Asn Leu Gln Leu Tyr Asn Thr Ala
            580                 585                 590

Pro Gly Ser Val Phe Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 33
<211> LENGTH: 2217
<212> TYPE: DNA
<213> ORGANISM: Artificial Sequence
<220> FEATURE:
<223> OTHER INFORMATION: constructed sequence

<400> SEQUENCE: 33

atggctgccg atggttatct tccagattgg ctcgaggaca acctctctga gggcattcgc     60
```

-continued

```
gagtggtggg cgctgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca acaaccacct ctacaagcaa    780
atctccaacg ggacatcggg aggagccacc aacgacaaca cctacttcgg ctacagcacc    840
ccctgggggt attttgactt taacagattc cactgccact tttcaccacg tgactggcag    900
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca acaacggtag tcaggccgtg ggacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga tttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgca gcagcaaaac acggctcctc aaattggaac tgtcaacagc   1800
caggggggcct tacccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctgtaa      2217
```

<210> SEQ ID NO 34
<211> LENGTH: 738
<212> TYPE: PRT
<213> ORGANISM: Artificial Sequence
<220> FEATURE:

<223> OTHER INFORMATION: constructed sequence

<400> SEQUENCE: 34

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Asn Gly Thr Ser Gly Gly Ala Thr Asn Asp
260 265 270

Asn Thr Tyr Phe Gly Tyr Ser Thr Pro Trp Gly Tyr Phe Asp Phe Asn
275 280 285

Arg Phe His Cys His Phe Ser Pro Arg Asp Trp Gln Arg Leu Ile Asn
290 295 300

Asn Asn Trp Gly Phe Arg Pro Lys Arg Leu Ser Phe Lys Leu Phe Asn
305 310 315 320

Ile Gln Val Lys Glu Val Thr Gln Asn Glu Gly Thr Lys Thr Ile Ala
325 330 335

Asn Asn Leu Thr Ser Thr Ile Gln Val Phe Thr Asp Ser Glu Tyr Gln
340 345 350

Leu Pro Tyr Val Leu Gly Ser Ala His Gln Gly Cys Leu Pro Pro Phe
355 360 365

Pro Ala Asp Val Phe Met Ile Pro Gln Tyr Gly Tyr Leu Thr Leu Asn
370 375 380

Asn Gly Ser Gln Ala Val Gly Arg Ser Ser Phe Tyr Cys Leu Glu Tyr
385 390 395 400

```
Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 35
<211> LENGTH: 594
<212> TYPE: DNA
<213> ORGANISM: Artificial Sequence
<220> FEATURE:
<223> OTHER INFORMATION: constructed sequence

<400> SEQUENCE: 35

```
ctggcgactc agagtcagtt ccagaccctc aacctctcgg agaacctcca gcagcgccct      60

ctggtgtggg acctaataca atggctgcag gcggtggcgc accaatggca gacaataacg     120
```

-continued

```
aaggcgccga cggagtgggt agttcctcgg gaaattggca ttgcgattcc acatggctgg    180

gcgacagagt catcaccacc agcacccgaa cctgggccct gcccacctac aacaaccacc    240

tctacaagca aatctccaac gggacatcgg gaggagccac caacgacaac acctacttcg    300

gctacagcac cccctggggg tattttgact ttaacagatt ccactgccac ttttcaccac    360

gtgactggca gcgactcatc aacaacaact ggggattccg gcccaagaga ctcagcttca    420

agctcttcaa catccaggtc aaggaggtca cgcagaatga aggcaccaag accatcgcca    480

ataacctcac cagcaccatc caggtgttta cggactcgga gtaccagctg ccgtacgttc    540

tcggctctgc ccaccagggc tgcctgcctc cgttcccggc ggacgtgttc atga          594
```

<210> SEQ ID NO 36
<211> LENGTH: 197
<212> TYPE: PRT
<213> ORGANISM: Artificial Sequence
<220> FEATURE:
<223> OTHER INFORMATION: constructed sequence

<400> SEQUENCE: 36

```
Leu Ala Thr Gln Ser Gln Phe Gln Thr Leu Asn Leu Ser Glu Asn Leu
1               5                   10                  15

Gln Gln Arg Pro Leu Val Trp Asp Leu Ile Gln Trp Leu Gln Ala Val
            20                  25                  30

Ala His Gln Trp Gln Thr Ile Thr Lys Ala Pro Thr Glu Trp Val Val
        35                  40                  45

Pro Arg Glu Ile Gly Ile Ala Ile Pro His Gly Trp Ala Thr Glu Ser
    50                  55                  60

Ser Pro Pro Ala Pro Glu Pro Gly Pro Cys Pro Pro Thr Thr Thr Thr
65                  70                  75                  80

Ser Thr Ser Lys Ser Pro Thr Gly His Arg Glu Glu Pro Pro Thr Thr
                85                  90                  95

Thr Pro Thr Ser Ala Thr Ala Pro Pro Gly Gly Ile Leu Thr Leu Thr
            100                 105                 110

Asp Ser Thr Ala Thr Phe His His Val Thr Gly Ser Asp Ser Ser Thr
        115                 120                 125

Thr Thr Gly Asp Ser Gly Pro Arg Asp Ser Ala Ser Ser Ser Ser Thr
    130                 135                 140

Ser Arg Ser Arg Arg Ser Arg Arg Met Lys Ala Pro Arg Pro Ser Pro
145                 150                 155                 160

Ile Thr Ser Pro Ala Pro Ser Arg Cys Leu Arg Thr Arg Ser Thr Ser
                165                 170                 175

Cys Arg Thr Phe Ser Ala Leu Pro Thr Arg Ala Ala Cys Leu Arg Ser
            180                 185                 190

Arg Arg Thr Cys Ser
        195
```

<210> SEQ ID NO 37
<211> LENGTH: 591
<212> TYPE: DNA
<213> ORGANISM: Artificial Sequence
<220> FEATURE:
<223> OTHER INFORMATION: constructed sequence

<400> SEQUENCE: 37

```
ctggcgactc agagtcagtt ccagaccctc aacctctcgg agaacctcca gcagcgccct     60

ctggtgtggg acctaataca atggctgcag gcggtggcgc accaatggca gacaataacg    120
```

-continued aaggcgccga cggagtgggt agttcctcgg gaaattggca ttgcgattcc acatggctgg 180
gcgacagagt catcaccacc agcacccgaa cctgggccct gcccacctac aacaaccacc 240
tctacaagca aatctcctct ggtactcatg gagccaccaa cgacaacacc tacttcggct 300
acagcacccc ctgggggtat tttgacttta acagattcca ctgccacttt tcaccacgtg 360
actggcagcg actcatcaac aacaactggg gattccggcc caagagactc agcttcaagc 420
tcttcaacat ccaggtcaag gaggtcacgc agaatgaagg caccaagacc atcgccaata 480
acctcaccag caccatccag gtgtttacgg actcggagta ccagctgccg tacgttctcg 540
gctctgccca ccagggctgc ctgcctccgt tcccggcgga cgtgttcatg a 591

<210> SEQ ID NO 38
<211> LENGTH: 196
<212> TYPE: PRT
<213> ORGANISM: Artificial Sequence
<220> FEATURE:
<223> OTHER INFORMATION: constructed sequence

<400> SEQUENCE: 38

Leu Ala Thr Gln Ser Gln Phe Gln Thr Leu Asn Leu Ser Glu Asn Leu
1 5 10 15

Gln Gln Arg Pro Leu Val Trp Asp Leu Ile Gln Trp Leu Gln Ala Val
20 25 30

Ala His Gln Trp Gln Thr Ile Thr Lys Ala Pro Thr Glu Trp Val Val
35 40 45

Pro Arg Glu Ile Gly Ile Ala Ile Pro His Gly Trp Ala Thr Glu Ser
50 55 60

Ser Pro Pro Ala Pro Glu Pro Gly Pro Cys Pro Pro Thr Thr Thr Thr
65 70 75 80

Ser Thr Ser Lys Ser Pro Leu Val Leu Met Glu Pro Pro Thr Thr Thr
85 90 95

Pro Thr Ser Ala Thr Ala Pro Pro Gly Gly Ile Leu Thr Leu Thr Asp
100 105 110

Ser Thr Ala Thr Phe His His Val Thr Gly Ser Asp Ser Ser Thr Thr
115 120 125

Thr Gly Asp Ser Gly Pro Arg Asp Ser Ala Ser Ser Ser Ser Thr Ser
130 135 140

Arg Ser Arg Arg Ser Arg Arg Met Lys Ala Pro Arg Pro Ser Pro Ile
145 150 155 160

Thr Ser Pro Ala Pro Ser Arg Cys Leu Arg Thr Arg Ser Thr Ser Cys
165 170 175

Arg Thr Phe Ser Ala Leu Pro Thr Arg Ala Ala Cys Leu Arg Ser Arg
180 185 190

Arg Thr Cys Ser
195

<210> SEQ ID NO 39
<211> LENGTH: 5500
<212> TYPE: DNA
<213> ORGANISM: Artificial Sequence
<220> FEATURE:
<223> OTHER INFORMATION: constructed sequence

<400> SEQUENCE: 39
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120

-continued

```
aggggttcct tgtagttaat gattaacccg ccatgctact tatctacgta gccatgctct    180
aggaagatcg gaattcgccc ttaagctagc aaaaaccaac acacagatcc aatgaaaata    240
aggatctttt atttctagat tagggcaagg cggagccgga ggcgatggcg tgctcggtca    300
ggtgccactt ctggttcttg gcgtcgctgc ggtcctcgcg ggtcagcttg tgctggatga    360
agtgccagtc gggcatcttg cggggcacgg acttggcctt gtacacggtg tcgaactggc    420
agcgcaagcg gccaccgtcc ttcagcagca ggtacatgct cacgtcgccc ttcaagatgc    480
cctgcttggg cacggggatg atcttctcgc aggagggctc ccagttgtcg gtcatcttct    540
tcatcacggg gccgtcggcg gggaagttca cgccgtagaa cttggactcg tggtacatgc    600
agttctcctc cacgctcacg gtgatgtcgg cgttgcagat gcacacggcg ccgtcctcga    660
acaggaagga gcggtcccag gtgtagccgg cggggcagga gttcttgaag tagtcgacga    720
tgtcctgggg gtactcggtg aacacgcggt tgccgtacat gaaggcggcg gacaagatgt    780
cctcggcgaa gggcaagggg ccgccctcca ccacgcacag gttgatggcc tgcttgccct    840
tgaaggggta gccgatgccc tcgccggtga tcacgaactt gtggccgtcc acgcagccct    900
ccatgcggta cttcatggtc atctccttgg tcaggccgtg cttggactgg gccatggtgg    960
ctctagatcg aaaggcccgg agatgaggaa gaggagaaca gcgcggcaga cgtgcgcttt   1020
tgaagcgtgc agaatgccgg gcctccggag gaccttcggg cgcccgcccc gcccctgagc   1080
ccgcccctga gcccgccccc ggacccaccc cttcccagcc tctgagccca gaaagcgaag   1140
gagcaaagct gctattggcc gctgccccaa aggcctaccc gcttccattg ctcagcggtg   1200
ctgtccatct gcacgagact agctagtgag acgtgctact tccatttgtc acgtcctgca   1260
cgacgcgagc tgcggggcgg gggggaactt cctgactagg ggaggagtag aaggtggcgc   1320
gaaggggcca ccaaagaacg gagccggttg gcgcctaccg gtggatgtgg aatgtgtgcg   1380
aggccagagg ccacttgtgt agcgccaagt gcccagcggg gctgctaaag cgcatgctcc   1440
agactgcctt gggaaaagcg cctcccctac ccggtagcta gctagttatt aatagtaatc   1500
aattacgggg tcattagttc atagcccata tatggagttc cgcgttacat aacttacggt   1560
aaatggcccg cctggctgac cgcccaacga cccccgccca ttgacgtcaa taatgacgta   1620
tgttcccata gtaacgccaa tagggacttt ccattgacgt caatgggtgg agtatttacg   1680
gtaaactgcc cacttggcag tacatcaagt gtatcatatg ccaagtacgc cccctattga   1740
cgtcaatgac ggtaaatggc ccgcctggca ttatgcccag tacatgacct tatgggactt   1800
tcctacttgg cagtacatct acgtattagt catcgctatt accatggtga tgcggttttg   1860
gcagtacatc aatgggcgtg gatagcggtt tgactcacgg ggatttccaa gtctccaccc   1920
cattgacgtc aatgggagtt tgttttggca ccaaaatcaa cgggactttc caaaatgtcg   1980
taacaactcc gccccattga cgcaaatggg cggtaggcgt gtacggtggg aggtctatat   2040
aagcagagct ggtttagtga accgtcagat cctgcatgaa gcttcgatca actacgcaga   2100
caggtaccaa aacaaatgtt ctcgtcacgt gggcatgaat ctgatgctgt ttccctgcag   2160
acaatgcgag agaatgaatc agaattcaaa tatctgcttc actcacggac agaaagactg   2220
tttagagtgc tttcccgtgt cagaatctca acccgtttct gtcgtcaaaa aggcgtatca   2280
gaaactgtgc tacattcatc atatcatggg aaaggtgcca gacgcttgca ctgcctgcga   2340
tctggtcaat gtggatttgg atgactgcat ctttgaacaa taaatgattt aaatcaggta   2400
tggcaggtgc taagtactag ttaatcaata aaccggacat tcgaaaggct gcggtcgaac   2460
gcatgctggg gactcgagtt aagggcgaat tcccgataag gatcttccta gagcatggct   2520
```

```
acgtagataa gtagcatggc gggttaatca ttaactacaa ggaaccccta gtgatggagt   2580
tggccactcc ctctctgcgc gctcgctcgc tcactgaggc cgggcgacca aaggtcgccc   2640
gacgcccggg ctttgcccgg gcggcctcag tgagcgagcg agcgcgcagc cttaattaac   2700
ctaattcact ggccgtcgtt ttacaacgtc gtgactggga aaaccctggc gttacccaac   2760
ttaatcgcct tgcagcacat ccccctttcg ccagctggcg taatagcgaa gaggcccgca   2820
ccgatcgccc ttcccaacag ttgcgcagcc tgaatggcga atgggacgcg ccctgtagcg   2880
gcgcattaag cgcggcgggt gtggtggtta cgcgcagcgt gaccgctaca cttgccagcg   2940
ccctagcgcc cgctcctttc gctttcttcc cttcctttct cgccacgttc gccggctttc   3000
cccgtcaagc tctaaatcgg gggctccctt tagggttccg atttagtgct ttacggcacc   3060
tcgaccccaa aaaacttgat tagggtgatg gttcacgtag tgggccatcg ccccgataga   3120
cggtttttcg ccctttgacg ctggagttca cgttcctcaa tagtggactc ttgttccaaa   3180
ctggaacaac actcaaccct atctcggtct attcttttga tttataaggg atttttccga   3240
tttcggccta ttggttaaaa aatgagctga tttaacaaaa atttaacgcg aattttaaca   3300
aaatattaac gtttataatt tcaggtggca tctttcgggg aaatgtgcgc ggaaccccta   3360
tttgtttatt tttctaaata cattcaaata tgtatccgct catgagacaa taaccctgat   3420
aaatgcttca ataatattga aaaaggaaga gtatgagtat tcaacatttc cgtgtcgccc   3480
ttattccctt ttttgcggca ttttgccttc ctgtttttgc tcacccagaa acgctggtga   3540
aagtaaaaga tgctgaagat cagttgggtg cacgagtggg ttacatcgaa ctggatctca   3600
atagtggtaa gatccttgag agttttcgcc ccgaagaacg ttttccaatg atgagcactt   3660
ttaaagttct gctatgtggc gcggtattat cccgtattga cgccgggcaa gagcaactcg   3720
gtcgccgcat acactattct cagaatgact tggttgagta ctcaccagtc acagaaaagc   3780
atcttacgga tggcatgaca gtaagagaat tatgcagtgc tgccataacc atgagtgata   3840
acactgcggc caacttactt ctgacaacga tcggaggacc gaaggagcta accgcttttt   3900
tgcacaacat gggggatcat gtaactcgcc ttgatcgttg ggaaccggag ctgaatgaag   3960
ccataccaaa cgacgagcgt gacaccacga tgcctgtagt aatggtaaca acgttgcgca   4020
aactattaac tggcgaacta cttactctag cttcccggca acaattaata gactggatgg   4080
aggcggataa agttgcagga ccacttctgc gctcggccct tccggctggc tggtttattg   4140
ctgataaatc tggagccggt gagcgtgggt ctcgcggtat cattgcagca ctggggccag   4200
atggtaagcc ctcccgtatc gtagttatct acacgacggg gagtcaggca actatggatg   4260
aacgaaatag acagatcgct gagataggtg cctcactgat taagcattgg taactgtcag   4320
accaagttta ctcatatata ctttagattg atttaaaact tcatttttaa tttaaaagga   4380
tctaggtgaa gatccttttt gataatctca tgaccaaaat cccttaacgt gagttttcgt   4440
tccactgagc gtcagacccc gtagaaaaga tcaaaggatc ttcttgagat cctttttttc   4500
tgcgcgtaat ctgctgcttg caaacaaaaa aaccaccgct accagcggtg gtttgtttgc   4560
cggatcaaga gctaccaact ctttttccga aggtaactgg cttcagcaga gcgcagatac   4620
caaatactgt ccttctagtg tagccgtagt taggccacca cttcaagaac tctgtagcac   4680
cgcctacata cctcgctctg ctaatcctgt taccagtggc tgctgccagt ggcgataagt   4740
cgtgtcttac cgggttggac tcaagacgat agttaccgga taaggcgcag cggtcgggct   4800
gaacgggggg ttcgtgcaca cagcccagct tggagcgaac gacctacacc gaactgagat   4860
```

acctacagcg tgagctatga gaaagcgcca cgcttcccga agggagaaag gcggacaggt 4920
atccggtaag cggcagggtc ggaacaggag agcgcacgag ggagcttcca gggggaaacg 4980
cctggtatct ttatagtcct gtcgggtttc gccacctctg acttgagcgt cgatttttgt 5040
gatgctcgtc aggggggcgg agcctatgga aaaacgccag caacgcggcc tttttacggt 5100
tcctggcctt ttgctgcggt tttgctcaca tgttctttcc tgcgttatcc cctgattctg 5160
tggataaccg tattaccgcc tttgagtgag ctgataccgc tcgccgcagc cgaacgaccg 5220
agcgcagcga gtcagtgagc gaggaagcgg aagagcgccc aatacgcaaa ccgcctctcc 5280
ccgcgcgttg gccgattcat taatgcagct ggcacgacag gtttcccgac tggaaagcgg 5340
gcagtgagcg caacgcaatt aatgtgagtt agctcactca ttaggcaccc caggctttac 5400
actttatgct tccggctcgt atgttgtgtg gaattgtgag cggataacaa tttcacacag 5460
gaaacagcta tgaccatgat tacgccagat ttaattaagg 5500

<210> SEQ ID NO 40
<211> LENGTH: 4365
<212> TYPE: DNA
<213> ORGANISM: Artificial Sequence
<220> FEATURE:
<223> OTHER INFORMATION: constructed sequence

<400> SEQUENCE: 40
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc tagttattaa tagtaatcaa ttacggggtc 240
attagttcat agcccatata tggagttccg cgttacataa cttacggtaa atggcccgcc 300
tggctgaccg cccaacgacc cccgcccatt gacgtcaata atgacgtatg ttcccatagt 360
aacgccaata gggactttcc attgacgtca atgggtggag tatttacggt aaactgccca 420
cttggcagta catcaagtgt atcatatgcc aagtacgccc cctattgacg tcaatgacgg 480
taaatggccc gcctggcatt atgcccagta catgacctta tgggactttc ctacttggca 540
gtacatctac gtattagtca tcgctattac catggtgatg cggttttggc agtacatcaa 600
tgggcgtgga tagcggtttg actcacgggg atttccaagt ctccacccca ttgacgtcaa 660
tgggagtttg ttttggcacc aaaatcaacg ggactttcca aaatgtcgta acaactccgc 720
cccattgacg caaatgggcg gtaggcgtgt acggtgggag gtctatataa gcagagctgg 780
tttagtgaac cgtcagatcc tgcatgaagc ttcgatcaac tacgcagaca ggtaccaaaa 840
caaatgttct cgtcacgtgg gcatgaatct gatgctgttt ccctgcagac aatgcgagag 900
aatgaatcag aattcaaata tctgcttcac tcacggacag aaagactgtt tagagtgctt 960
tcccgtgtca gaatctcaac ccgtttctgt cgtcaaaaag gcgtatcaga aactgtgcta 1020
cattcatcat atcatgggaa aggtgccaga cgcttgcact gcctgcgatc tggtcaatgt 1080
ggatttggat gactgcatct ttgaacaata aatgatttaa atcaggtatg gcaggtgcta 1140
actagtgatc cgatcttttt ccctctgcca aaaattatgg ggacatcatg aagccccttg 1200
agcatctgac ttctggctaa taaaggaaat ttattttcat tgcaatagtg tgttggaatt 1260
ttttgtgtct ctcactcgga tctagttaat caataaaccg gacattcgaa aggctgcggt 1320
cgaacgcatg ctggggactc gagttaaggg cgaattcccg attaggatct tcctagagca 1380
tggctacgta gataagtagc atggcgggtt aatcattaac tacaaggaac ccctagtgat 1440

-continued

```
ggagttggcc actccctctc tgcgcgctcg ctcgctcact gaggccgggc gaccaaaggt   1500
cgcccgacgc ccgggctttg cccgggcggc ctcagtgagc gagcgagcgc gcagccttaa   1560
ttaacctaat tcactggccg tcgttttaca acgtcgtgac tgggaaaacc ctggcgttac   1620
ccaacttaat cgccttgcag cacatccccc tttcgccagc tggcgtaata gcgaagaggc   1680
ccgcaccgat cgcccttccc aacagttgcg cagcctgaat ggcgaatggg acgcgccctg   1740
tagcggcgca ttaagcgcgg cgggtgtggt ggttacgcgc agcgtgaccg ctacacttgc   1800
cagcgcccta gcgcccgctc ctttcgcttt cttcccttcc tttctcgcca cgttcgccgg   1860
ctttccccgt caagctctaa atcgggggct ccctttaggg ttccgattta gtgctttacg   1920
gcacctcgac cccaaaaaac ttgattaggg tgatggttca cgtagtgggc catcgccccg   1980
atagacggtt tttcgccctt tgacgctgga gttcacgttc ctcaatagtg gactcttgtt   2040
ccaaactgga acaacactca accctatctc ggtctattct tttgatttat aagggatttt   2100
tccgatttcg gcctattggt taaaaaatga gctgatttaa caaaaattta acgcgaattt   2160
taacaaaata ttaacgttta taatttcagg tggcatcttt cggggaaatg tgcgcggaac   2220
ccctatttgt ttatttttct aaatacattc aaatatgtat ccgctcatga gacaataacc   2280
ctgataaatg cttcaataat attgaaaaag gaagagtatg agtattcaac atttccgtgt   2340
cgcccttatt cccttttttg cggcattttg ccttcctgtt tttgctcacc cagaaacgct   2400
ggtgaaagta aaagatgctg aagatcagtt gggtgcacga gtgggttaca tcgaactgga   2460
tctcaatagt ggtaagatcc ttgagagttt tcgccccgaa gaacgttttc caatgatgag   2520
cacttttaaa gttctgctat gtggcgcggt attatcccgt attgacgccg ggcaagagca   2580
actcggtcgc cgcatacact attctcagaa tgacttggtt gagtactcac cagtcacaga   2640
aaagcatctt acggatggca tgacagtaag agaattatgc agtgctgcca taaccatgag   2700
tgataacact gcggccaact tacttctgac aacgatcgga ggaccgaagg agctaaccgc   2760
ttttttgcac aacatggggg atcatgtaac tcgccttgat cgttgggaac cggagctgaa   2820
tgaagccata ccaaacgacg agcgtgacac cacgatgcct gtagtaatgg taacaacgtt   2880
gcgcaaacta ttaactggcg aactacttac tctagcttcc cggcaacaat taatagactg   2940
gatggaggcg gataaagttg caggaccact tctgcgctcg gcccttccgg ctggctggtt   3000
tattgctgat aaatctggag ccggtgagcg tgggtctcgc ggtatcattg cagcactggg   3060
gccagatggt aagccctccc gtatcgtagt tatctacacg acggggagtc aggcaactat   3120
ggatgaacga aatagacaga tcgctgagat aggtgcctca ctgattaagc attggtaact   3180
gtcagaccaa gtttactcat atatacttta gattgattta aaacttcatt tttaatttaa   3240
aaggatctag gtgaagatcc tttttgataa tctcatgacc aaaatccctt aacgtgagtt   3300
ttcgttccac tgagcgtcag accccgtaga aaagatcaaa ggatcttctt gagatccttt   3360
ttttctgcgc gtaatctgct gcttgcaaac aaaaaaacca ccgctaccag cggtggtttg   3420
tttgccggat caagagctac caactctttt tccgaaggta actggcttca gcagagcgca   3480
gataccaaat actgtccttc tagtgtagcc gtagttaggc caccacttca agaactctgt   3540
agcaccgcct acatacctcg ctctgctaat cctgttacca gtggctgctg ccagtggcga   3600
taagtcgtgt cttaccgggt tggactcaag acgatagtta ccggataagg cgcagcggtc   3660
gggctgaacg gggggttcgt gcacacagcc cagcttggag cgaacgacct acaccgaact   3720
gagataccta cagcgtgagc tatgagaaag cgccacgctt cccgaaggga gaaaggcgga   3780
```

caggtatccg gtaagcggca gggtcggaac aggagagcgc acgagggagc ttccaggggg 3840
aaacgcctgg tatctttata gtcctgtcgg gtttcgccac ctctgacttg agcgtcgatt 3900
tttgtgatgc tcgtcagggg ggcggagcct atggaaaaac gccagcaacg cggccttttt 3960
acggttcctg gccttttgct gcggttttgc tcacatgttc tttcctgcgt tatcccctga 4020
ttctgtggat aaccgtatta ccgcctttga gtgagctgat accgctcgcc gcagccgaac 4080
gaccgagcgc agcgagtcag tgagcgagga agcggaagag cgcccaatac gcaaaccgcc 4140
tctccccgcg cgttggccga ttcattaatg cagctggcac gacaggtttc ccgactggaa 4200
agcgggcagt gagcgcaacg caattaatgt gagttagctc actcattagg caccccaggc 4260
tttacacttt atgcttccgg ctcgtatgtt gtgtggaatt gtgagcggat aacaatttca 4320
cacaggaaac agctatgacc atgattacgc cagatttaat taagg 4365

<210> SEQ ID NO 41
<211> LENGTH: 6627
<212> TYPE: DNA
<213> ORGANISM: Artificial Sequence
<220> FEATURE:
<223> OTHER INFORMATION: constructed sequence

<400> SEQUENCE: 41
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc tagttattaa tagtaatcaa ttacggggtc 240
attagttcat agcccatata tggagttccg cgttacataa cttacggtaa atggcccgcc 300
tggctgaccg cccaacgacc cccgcccatt gacgtcaata atgacgtatg ttcccatagt 360
aacgccaata gggactttcc attgacgtca atgggtggag tatttacggt aaactgccca 420
cttggcagta catcaagtgt atcatatgcc aagtacgccc cctattgacg tcaatgacgg 480
taaatggccc gcctggcatt atgcccagta catgacctta tgggactttc ctacttggca 540
gtacatctac gtattagtca tcgctattac catggtgatg cggttttggc agtacatcaa 600
tgggcgtgga tagcggtttg actcacgggg atttccaagt ctccacccca ttgacgtcaa 660
tgggagtttg ttttggcacc aaaatcaacg ggactttcca aaatgtcgta acaactccgc 720
cccattgacg caaatgggcg gtaggcgtgt acggtgggag gtctatataa gcagagctgg 780
tttagtgaac cgtcagatcc tgcatgaagc ttcgatcaac tacgcagaca ggtaccaaaa 840
caaatgttct cgtcacgtgg gcatgaatct gatgctgttt ccctgcagac aatgcgagag 900
aatgaatcag aattcaaata tctgcttcac tcacggacag aaagactgtt tagagtgctt 960
tcccgtgtca gaatctcaac ccgtttctgt cgtcaaaaag gcgtatcaga aactgtgcta 1020
cattcatcat atcatgggaa aggtgccaga cgcttgcact gcctgcgatc tggtcaatgt 1080
ggatttggat gactgcatct ttgaacaata aatgatttaa atcaggtatg gctgccgatg 1140
gttatcttcc agattggctc gaggacaacc tctctgaggg cattcgcgag tggtgggcgc 1200
tgaaacctgg agccccgaag cccaaagcca accagcaaaa gcaggacgac ggccggggtc 1260
tggtgcttcc tggctacaag tacctcggac ccttcaacgg actcgacaag ggggagcccg 1320
tcaacgcggc ggacgcagcg gccctcgagc acgacaaggc ctacgaccag cagctgcagg 1380
cgggtgacaa tccgtacctg cggtataacc acgccgacgc cgagtttcag gagcgtctgc 1440
aagaagatac gtcttttggg ggcaacctcg ggcgagcagt cttccaggcc aagaagcggg 1500

```
ttctcgaacc tctcggtctg gttgaggaag gcgctaagac ggctcctgga aagaagagac   1560
cggtagagcc atcaccccag cgttctccag actcctctac gggcatcggc aagaaaggcc   1620
aacagcccgc cagaaaaaga ctcaattttg gtcagactgg cgactcagag tcagttccag   1680
accctcaacc tctcggagaa cctccagcag cgccctctgg tgtgggacct aatacaatgg   1740
ctgcaggcgg tggcgcacca atggcagaca ataacgaagg cgccgacgga gtgggtagtt   1800
cctcgggaaa ttggcattgc gattccacat ggctgggcga cagagtcagg agacgcgcac   1860
agatgcgtaa ggagaaaata ccgcatcagg cgccattcgc cattcaggct gcgcaactgt   1920
tgggaagggc gatcggtgcg ggcctcttcg ctattacgcc agctggcgaa aggggggatgt   1980
gctgcaaggc gattcgtctc gcaacaccta cttcggctac agcacccccct gggggtattt   2040
tgactttaac agattccact gccacttttc accacgtgac tggcagcgac tcatcaacaa   2100
caactgggga ttccggccca agagactcag cttcaagctc ttcaacatcc aggtcaagga   2160
ggtcacgcag aatgaaggca ccaagaccat cgccaataac ctcaccagca ccatccaggt   2220
gtttacggac tcggagtacc agctgccgta cgttctcggc tctgcccacc agggctgcct   2280
gcctccgttc ccggcggacg tgttcatgat tccccagtac ggctacctaa cactcaacaa   2340
cggtagtcag gccgtgggac gctcctcctt ctactgcctg gaatactttc cttcgcagat   2400
gctgagaacc ggcaacaact tccagtttac ttacaccttc gaggacgtgc ctttccacag   2460
cagctacgcc cacagccaga gcttggaccg gctgatgaat cctctgattg accagtacct   2520
gtactacttg tctcggactc aaacaacagg aggcacggca aatacgcaga ctctgggctt   2580
cagccaaggt gggcctaata caatggccaa tcaggcaaag aactggctgc caggaccctg   2640
ttaccgccaa caacgcgtgt caacgacaac cgggcaaaac aacaatagca actttgcctg   2700
gactgctggg accaaatacc atctgaatgg aagaaattca ttggctaatc ctggcatcgc   2760
tatggcaaca cacaaagacg acgaggagcg ttttttttccc agtaacggga tcctgatttt   2820
tggcaaacaa aatgctgcca gagacaatgc ggattacagc gatgtcatgc tcaccagcga   2880
ggaagaaatc aaaaccacta accctgtggc tacagaggaa tacggtatcg tgggtgataa   2940
cttgcagttg tataacacgg ctcctggttc ggtgtttgtc aacagccagg gggccttacc   3000
cggtatggtc tggcagaacc gggacgtgta cctgcagggt cccatctggg ccaagattcc   3060
tcacacggac ggcaacttcc acccgtcccc gctgatgggc ggctttggcc tgaaacatcc   3120
tccgcctcag atcctgatca agaacacgcc tgtacctgcg gatcctccga ccaccttcaa   3180
ccagtcaaag ctgaactctt tcatcacgca atacagcacc ggacaggtca gcgtggaaat   3240
tgaatgggag ctgcagaagg aaaacagcaa gcgctggaac cccgagatcc agtacacctc   3300
caactactac aaatctacaa gtgtggactt tgctgttaat acagaaggcg tgtactctga   3360
accccgcccc attggcaccc gttacctcac ccgtaatctg taactagtga tccgatcttt   3420
ttccctctgc caaaaattat ggggacatca tgaagcccct tgagcatctg acttctggct   3480
aataaaggaa atttattttc attgcaatag tgtgttggaa ttttttgtgt ctctcactcg   3540
gatctagtta atcaataaac cggacattcg aaaggctgcg gtcgaacgca tgctggggac   3600
tcgagttaag ggcgaattcc cgattaggat cttcctagag catggctacg tagataagta   3660
gcatggcggg ttaatcatta actacaagga acccctagtg atggagttgg ccactccctc   3720
tctgcgcgct cgctcgctca ctgaggccgg gcgaccaaag gtcgcccgac gcccgggctt   3780
tgcccgggcg gcctcagtga gcgagcgagc gcgcagcctt aattaaccta attcactggc   3840
```

-continued cgtcgtttta caacgtcgtg actgggaaaa ccctggcgtt acccaactta atcgccttgc 3900
agcacatccc cctttcgcca gctggcgtaa tagcgaagag gcccgcaccg atcgcccttc 3960
ccaacagttg cgcagcctga atggcgaatg ggacgcgccc tgtagcggcg cattaagcgc 4020
ggcgggtgtg gtggttacgc gcagcgtgac cgctacactt gccagcgccc tagcgcccgc 4080
tcctttcgct ttcttccctt cctttctcgc cacgttcgcc ggctttcccc gtcaagctct 4140
aaatcggggg ctccctttag ggttccgatt tagtgcttta cggcacctcg accccaaaaa 4200
acttgattag ggtgatggtt cacgtagtgg gccatcgccc cgatagacgg tttttcgccc 4260
tttgacgctg gagttcacgt tcctcaatag tggactcttg ttccaaactg gaacaacact 4320
caaccctatc tcggtctatt cttttgattt ataagggatt tttccgattt cggcctattg 4380
gttaaaaaat gagctgattt aacaaaaatt taacgcgaat tttaacaaaa tattaacgtt 4440
tataatttca ggtggcatct ttcggggaaa tgtgcgcgga acccctattt gtttattttt 4500
ctaaatacat tcaaatatgt atccgctcat gagacaataa ccctgataaa tgcttcaata 4560
atattgaaaa aggaagagta tgagtattca acatttccgt gtcgccctta ttcccttttt 4620
tgcggcattt tgccttcctg tttttgctca cccagaaacg ctggtgaaag taaaagatgc 4680
tgaagatcag ttgggtgcac gagtgggtta catcgaactg gatctcaata gtggtaagat 4740
ccttgagagt tttcgccccg aagaacgttt tccaatgatg agcactttta aagttctgct 4800
atgtggcgcg gtattatccc gtattgacgc cgggcaagag caactcggtc gccgcataca 4860
ctattctcag aatgacttgg ttgagtactc accagtcaca gaaaagcatc ttacggatgg 4920
catgacagta agagaattat gcagtgctgc cataaccatg agtgataaca ctgcggccaa 4980
cttacttctg acaacgatcg gaggaccgaa ggagctaacc gcttttttgc acaacatggg 5040
ggatcatgta actcgccttg atcgttggga accggagctg aatgaagcca taccaaacga 5100
cgagcgtgac accacgatgc ctgtagtaat ggtaacaacg ttgcgcaaac tattaactgg 5160
cgaactactt actctagctt cccggcaaca attaatagac tggatggagg cggataaagt 5220
tgcaggacca cttctgcgct cggcccttcc ggctggctgg tttattgctg ataaatctgg 5280
agccggtgag cgtgggtctc gcggtatcat tgcagcactg gggccagatg gtaagccctc 5340
ccgtatcgta gttatctaca cgacggggag tcaggcaact atggatgaac gaaatagaca 5400
gatcgctgag ataggtgcct cactgattaa gcattggtaa ctgtcagacc aagtttactc 5460
atatatactt tagattgatt taaaacttca tttttaattt aaaaggatct aggtgaagat 5520
cctttttgat aatctcatga ccaaaatccc ttaacgtgag ttttcgttcc actgagcgtc 5580
agaccccgta gaaaagatca aaggatcttc ttgagatcct ttttttctgc gcgtaatctg 5640
ctgcttgcaa acaaaaaaac caccgctacc agcggtggtt tgtttgccgg atcaagagct 5700
accaactctt tttccgaagg taactggctt cagcagagcg cagataccaa atactgtcct 5760
tctagtgtag ccgtagttag gccaccactt caagaactct gtagcaccgc ctacatacct 5820
cgctctgcta atcctgttac cagtggctgc tgccagtggc gataagtcgt gtcttaccgg 5880
gttggactca agacgatagt taccggataa ggcgcagcgg tcgggctgaa cggggggttc 5940
gtgcacacag cccagcttgg agcgaacgac ctacaccgaa ctgagatacc tacagcgtga 6000
gctatgagaa agcgccacgc ttcccgaagg gagaaaggcg gacaggtatc cggtaagcgg 6060
cagggtcgga acaggagagc gcacgaggga gcttccaggg ggaaacgcct ggtatcttta 6120
tagtcctgtc gggtttcgcc acctctgact tgagcgtcga tttttgtgat gctcgtcagg 6180
ggggcggagc ctatggaaaa acgccagcaa cgcggccttt ttacggttcc tggccttttg 6240
ctgcggtttt gctcacatgt tctttcctgc gttatcccct gattctgtgg ataaccgtat 6300
taccgccttt gagtgagctg ataccgctcg ccgcagccga acgaccgagc gcagcgagtc 6360
agtgagcgag gaagcggaag agcgcccaat acgcaaaccg cctctccccg cgcgttggcc 6420
gattcattaa tgcagctggc acgacaggtt tcccgactgg aaagcgggca gtgagcgcaa 6480
cgcaattaat gtgagttagc tcactcatta ggcaccccag gctttacact ttatgcttcc 6540
ggctcgtatg ttgtgtggaa ttgtgagcgg ataacaattt cacacaggaa acagctatga 6600
ccatgattac gccagattta attaagg 6627

<210> SEQ ID NO 42
<211> LENGTH: 6622
<212> TYPE: DNA
<213> ORGANISM: Artificial Sequence
<220> FEATURE:
<223> OTHER INFORMATION: constructed sequence

<400> SEQUENCE: 42
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaagctagc tagttattaa tagtaatcaa ttacggggtc 240
attagttcat agcccatata tggagttccg cgttacataa cttacggtaa atggcccgcc 300
tggctgaccg cccaacgacc cccgcccatt gacgtcaata atgacgtatg ttcccatagt 360
aacgccaata gggactttcc attgacgtca atgggtggag tatttacggt aaactgccca 420
cttggcagta catcaagtgt atcatatgcc aagtacgccc cctattgacg tcaatgacgg 480
taaatggccc gcctggcatt atgcccagta catgacctta tgggactttc ctacttggca 540
gtacatctac gtattagtca tcgctattac catggtgatg cggttttggc agtacatcaa 600
tgggcgtgga tagcggtttg actcacgggg atttccaagt ctccacccca ttgacgtcaa 660
tgggagtttg ttttggcacc aaaatcaacg ggactttcca aaatgtcgta acaactccgc 720
cccattgacg caaatgggcg gtaggcgtgt acggtgggag gtctatataa gcagagctgg 780
tttagtgaac cgtcagatcc tgcatgaagc ttcgatcaac tacgcagaca ggtaccaaaa 840
caaatgttct cgtcacgtgg gcatgaatct gatgctgttt ccctgcagac aatgcgagag 900
aatgaatcag aattcaaata tctgcttcac tcacggacag aaagactgtt tagagtgctt 960
tcccgtgtca gaatctcaac ccgtttctgt cgtcaaaaag gcgtatcaga aactgtgcta 1020
cattcatcat atcatgggaa aggtgccaga cgcttgcact gcctgcgatc tggtcaatgt 1080
ggatttggat gactgcatct ttgaacaata aatgatttaa atcaggtatg gctgccgatg 1140
gttatcttcc agattggctc gaggacaacc tctctgaggg cattcgcgag tggtgggcgc 1200
tgaaacctgg agccccgaag cccaaagcca accagcaaaa gcaggacgac ggccggggtc 1260
tggtgcttcc tggctacaag tacctcggac ccttcaacgg actcgacaag ggggagcccg 1320
tcaacgcggc ggacgcagcg gccctcgagc acgacaaggc ctacgaccag cagctgcagg 1380
cgggtgacaa tccgtacctg cggtataacc acgccgacgc cgagtttcag gagcgtctgc 1440
aagaagatac gtcttttggg ggcaacctcg ggcgagcagt cttccaggcc aagaagcggg 1500
ttctcgaacc tctcggtctg gttgaggaag gcgctaagac ggctcctgga aagaagagac 1560
cggtagagcc atcaccccag cgttctccag actcctctac gggcatcggc aagaaaggcc 1620
aacagcccgc cagaaaaaga ctcaattttg gtcagactgg cgactcagag tcagttccag 1680
accctcaacc tctcggagaa cctccagcag cgccctctgg tgtgggacct aatacaatgg 1740
ctgcaggcgg tggcgcacca atggcagaca ataacgaagg cgccgacgga gtgggtagtt 1800
cctcgggaaa ttggcattgc gattccacat ggctgggcga cagagtcatc accaccagca 1860
cccgaacctg ggccctgccc acctacaaca accacctcta caagcaaatc tccaacggga 1920
catcgggagg agccaccaac gacaacacct acttcggcta cagcaccccc tgggggtatt 1980
ttgactttaa cagattccac tgccactttt caccacgtga ctggcagcga ctcatcaaca 2040
acaactgggg attccggccc aagagactca gcttcaagct cttcaacatc caggtcaagg 2100
aggtcacgca gaatgaaggc accaagacca tcgccaataa cctcaccagc accatccagg 2160
tgtttacgga ctcggagtac cagctgccgt acgttctcgg ctctgcccac cagggctgcc 2220
tgcctccgtt cccggcggac gtgttcatga ttccccagta cggctaccta acactcaaca 2280
acggtagtca ggccgtggga cgctcctcct tctactgcct ggaatacttt ccttcgcaga 2340
tgctgagaac cggcaacaac ttccagttta cttacacctt cgaggacgtg cctttccaca 2400
gcagctacgc ccacagccag agcttggacc ggctgatgaa tcctcggaga cgcgcacaga 2460
tgcgtaagga gaaaataccg catcaggcgc cattcgccat tcaggctgcg caactgttgg 2520
gaagggcgat cggtgcgggc ctcttcgcta ttacgccagc tggcgaaagg gggatgtgct 2580
gcaaggcgat tcgtctcgtg gccaatcagg caaagaactg gctgccagga ccctgttacc 2640
gccaacaacg cgtgtcaacg acaaccgggc aaaacaacaa tagcaacttt gcctggactg 2700
ctgggaccaa ataccatctg aatggaagaa attcattggc taatcctggc atcgctatgg 2760
caacacacaa agacgacgag gagcgttttt ttcccagtaa cgggatcctg atttttggca 2820
aacaaaatgc tgccagagac aatgcggatt acagcgatgt catgctcacc agcgaggaag 2880
aaatcaaaac cactaaccct gtggctacag aggaatacgg tatcgtgggt gataacttgc 2940
agttgtataa cacggctcct ggttcggtgt ttgtcaacag ccaggggggcc ttacccggta 3000
tggtctggca gaaccgggac gtgtacctgc agggtcccat ctgggccaag attcctcaca 3060
cggacggcaa cttccacccg tccccgctga tgggcggctt tggcctgaaa catcctccgc 3120
ctcagatcct gatcaagaac acgcctgtac ctgcggatcc tccgaccacc ttcaaccagt 3180
caaagctgaa ctctttcatc acgcaataca gcaccggaca ggtcagcgtg gaaattgaat 3240
gggagctgca gaaggaaaac agcaagcgct ggaaccccga gatccagtac acctccaact 3300
actacaaatc tacaagtgtg gactttgctg ttaatacaga aggcgtgtac tctgaacccc 3360
gccccattgg cacccgttac ctcacccgta atctgtaact agtgatccga tctttttccc 3420
tctgccaaaa attatgggga catcatgaag ccccttgagc atctgacttc tggctaataa 3480
aggaaattta ttttcattgc aatagtgtgt tggaattttt tgtgtctctc actcggatct 3540
agttaatcaa taaaccggac attcgaaagg ctgcggtcga acgcatgctg gggactcgag 3600
ttaagggcga attcccgatt aggatcttcc tagagcatgg ctacgtagat aagtagcatg 3660
gcgggttaat cattaactac aaggaacccc tagtgatgga gttggccact ccctctctgc 3720
gcgctcgctc gctcactgag gccgggcgac caaaggtcgc ccgacgcccg ggctttgccc 3780
gggcggcctc agtgagcgag cgagcgcgca gccttaatta acctaattca ctggccgtcg 3840
ttttacaacg tcgtgactgg gaaaaccctg gcgttaccca acttaatcgc cttgcagcac 3900
atccccettt cgccagctgg cgtaatagcg aagaggcccg caccgatcgc ccttcccaac 3960
agttgcgcag cctgaatggc gaatgggacg cgccctgtag cggcgcatta agcgcggcgg 4020

-continued gtgtggtggt tacgcgcagc gtgaccgcta cacttgccag cgccctagcg cccgctcctt 4080
tcgctttctt cccttccttt ctcgccacgt tcgccggctt tccccgtcaa gctctaaatc 4140
gggggctccc tttagggttc cgatttagtg ctttacggca cctcgacccc aaaaaacttg 4200
attagggtga tggttcacgt agtgggccat cgccccgata gacggttttt cgccctttga 4260
cgctggagtt cacgttcctc aatagtggac tcttgttcca aactggaaca acactcaacc 4320
ctatctcggt ctattctttt gatttataag ggattttgcc gatttcggcc tattggttaa 4380
aaaatgagct gatttaacaa aaatttaacg cgaattttaa caaaatatta acgtttataa 4440
tttcaggtgg catctttcgg ggaaatgtgc gcggaacccc tatttgttta tttttctaaa 4500
tacattcaaa tatgtatccg ctcatgagac aataaccctg ataaatgctt caataatatt 4560
gaaaaaggaa gagtatgagt attcaacatt tccgtgtcgc ccttattccc ttttttgcgg 4620
cattttgcct tcctgttttt gctcacccag aaacgctggt gaaagtaaaa gatgctgaag 4680
atcagttggg tgcacgagtg ggttacatcg aactggatct caatagtggt aagatccttg 4740
agagttttcg ccccgaagaa cgttttccaa tgatgagcac ttttaaagtt ctgctatgtg 4800
gcgcggtatt atcccgtatt gacgccgggc aagagcaact cggtcgccgc atacactatt 4860
ctcagaatga cttggttgag tactcaccag tcacagaaaa gcatcttacg gatggcatga 4920
cagtaagaga attatgcagt gctgccataa ccatgagtga taacactgcg gccaacttac 4980
ttctgacaac gatcggagga ccgaaggagc taaccgcttt tttgcacaac atgggggatc 5040
atgtaactcg ccttgatcgt tgggaaccgg agctgaatga agccatacca aacgacgagc 5100
gtgacaccac gatgcctgta gtaatggtaa caacgttgcg caaactatta actggcgaac 5160
tacttactct agcttcccgg caacaattaa tagactggat ggaggcggat aaagttgcag 5220
gaccacttct gcgctcggcc cttccggctg gctggtttat tgctgataaa tctggagccg 5280
gtgagcgtgg gtctcgcggt atcattgcag cactggggcc agatggtaag ccctcccgta 5340
tcgtagttat ctacacgacg gggagtcagg caactatgga tgaacgaaat agacagatcg 5400
ctgagatagg tgcctcactg attaagcatt ggtaactgtc agaccaagtt tactcatata 5460
tactttagat tgatttaaaa cttcattttt aatttaaaag gatctaggtg aagatccttt 5520
ttgataatct catgaccaaa atcccttaac gtgagttttc gttccactga gcgtcagacc 5580
ccgtagaaaa gatcaaagga tcttcttgag atcctttttt tctgcgcgta atctgctgct 5640
tgcaaacaaa aaaaccaccg ctaccagcgg tggtttgttt gccggatcaa gagctaccaa 5700
ctctttttcc gaaggtaact ggcttcagca gagcgcagat accaaatact gtccttctag 5760
tgtagccgta gttaggccac cacttcaaga actctgtagc accgcctaca tacctcgctc 5820
tgctaatcct gttaccagtg gctgctgcca gtggcgataa gtcgtgtctt accgggttgg 5880
actcaagacg atagttaccg gataaggcgc agcggtcggg ctgaacgggg ggttcgtgca 5940
cacagcccag cttggagcga acgacctaca ccgaactgag atacctacag cgtgagctat 6000
gagaaagcgc cacgcttccc gaagggagaa aggcggacag gtatccggta agcggcaggg 6060
tcggaacagg agagcgcacg agggagcttc cagggggaaa cgcctggtat ctttatagtc 6120
ctgtcgggtt tcgccacctc tgacttgagc gtcgattttt gtgatgctcg tcaggggggc 6180
ggagcctatg gaaaaacgcc agcaacgcgg cctttttacg gttcctggcc ttttgctgcg 6240
gttttgctca catgttcttt cctgcgttat cccctgattc tgtggataac cgtattaccg 6300
cctttgagtg agctgatacc gctcgccgca gccgaacgac cgagcgcagc gagtcagtga 6360
gcgaggaagc ggaagagcgc ccaatacgca aaccgcctct ccccgcgcgt tggccgattc 6420
attaatgcag ctggcacgac aggtttcccg actggaaagc gggcagtgag cgcaacgcaa 6480
ttaatgtgag ttagctcact cattaggcac cccaggcttt acactttatg cttccggctc 6540
gtatgttgtg tggaattgtg agcggataac aatttcacac aggaaacagc tatgaccatg 6600
attacgccag atttaattaa gg 6622

<210> SEQ ID NO 43
<211> LENGTH: 7336
<212> TYPE: DNA
<213> ORGANISM: Artificial Sequence
<220> FEATURE:
<223> OTHER INFORMATION: constructed sequence

<400> SEQUENCE: 43
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggctct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800

-continued

```
ccagacgctt gcactgcctg cgatctggtc aatgtggatt tggatgactg catctttgaa   1860
caataaatga tttaaatcag gtatggctgc cgatggttat cttccagatt ggctcgagga   1920
caacctctct gagggcattc gcgagtggtg ggcgctgaaa cctggagccc cgaagcccaa   1980
agccaaccag caaaagcagg acgacggccg gggtctggtg cttcctggct acaagtacct   2040
cggacccttc aacggactcg acaaggggga gcccgtcaac gcggcggacg cagcggccct   2100
cgagcacgac aaggcctacg accagcagct gcaggcgggt gacaatccgt acctgcggta   2160
taaccacgcc gacgccgagt ttcaggagcg tctgcaagaa gatacgtctt ttgggggcaa   2220
cctcgggcga gcagtcttcc aggccaagaa gcgggttctc gaacctctcg gtctggttga   2280
ggaaggcgct aagacggctc ctggaaagaa gagaccggta gagccatcac cccagcgttc   2340
tccagactcc tctacgggca tcggcaagaa aggccaacag cccgccagaa aaagactcaa   2400
ttttggtcag actggcgact cagagtcagt tccagaccct caacctctcg gagaacctcc   2460
agcagcgccc tctggtgtgg gacctaatac aatggctgca ggcggtggcg caccaatggc   2520
agacaataac gaaggcgccg acggagtggg tagttcctcg ggaaattggc attgcgattc   2580
cacatggctg ggcgacagag tcatcaccac cagcacccga acctgggccc tgcccaccta   2640
caacaaccac ctctacaagc aaatctccaa cgggacatcg ggaggagcca ccaacgacaa   2700
cacctacttc ggctacagca ccccctgggg gtattttgac tttaacagat tccactgcca   2760
cttttcacca cgtgactggc agcgactcat caacaacaac tggggattcc ggcccaagag   2820
actcagcttc aagctcttca acatccaggt caaggaggtc acgcagaatg aaggcaccaa   2880
gaccatcgcc aataacctca ccagcaccat ccaggtgttt acggactcgg agtaccagct   2940
gccgtacgtt ctcggctctg cccaccaggg ctgcctgcct ccgttcccgg cggacgtgtt   3000
catgattccc cagtacggct acctaacact caacaacggt agtcaggccg tgggacgctc   3060
ctccttctac tgcctggaat actttccttc gcagatgctg agaaccggca acaacttcca   3120
gtttacttac accttcgagg acgtgccttt ccacagcagc tacgcccaca gccagagctt   3180
ggaccggctg atgaatcctc tgattgacca gtacctgtac tacttgtctc ggactcaaac   3240
aacaggaggc acggcaaata cgcagactct gggcttcagc caaggtgggc ctaatacaat   3300
ggccaatcag gcaaagaact ggctgccagg accctgttac cgccaacaac gcgtctcaac   3360
gacaaccggg caaaacaaca atagcaactt tgcctggact gctgggacca aataccatct   3420
gaatggaaga aattcattgg ctaatcctgg catcgctatg gcaacacaca aagacgacga   3480
ggagcgtttt tttcccagta acgggatcct gatttttggc aaacaaaatg ctgccagaga   3540
caatgcggat tacagcgatg tcatgctcac cagcgaggaa gaaatcaaaa ccactaaccc   3600
tgtggctaca gaggaatacg gtatcgtggc agataacttg cagcagcaaa acacggctcc   3660
tcaaattgga actgtcaaca gccagggggc cttacccggt atggtctggc agaaccggga   3720
cgtgtacctg cagggtccca tctgggccaa gattcctcac acggacggca acttccaccc   3780
gtctccgctg atgggcggct ttggcctgaa acatcctccg cctcagatcc tgatcaagaa   3840
cacgcctgta cctgcggatc ctccgaccac cttcaaccag tcaaagctga actctttcat   3900
cacgcaatac agcaccggac aggtcagcgt ggaaattgaa tgggagctgc agaaggaaaa   3960
cagcaagcgc tggaaccccg agatccagta cacctccaac tactacaaat ctacaagtgt   4020
ggactttgct gttaatacag aaggcgtgta ctctgaaccc cgccccattg gcacccgtta   4080
cctcacccgt aatctgtaat tgcctgttaa tcaataaacc ggttgattcg tttcagttga   4140
```

-continued actttggtct ctgcgaaggg cgaattcgtt taaacctgca ggactagagg tcctgtatta 4200
gaggtcacgt gagtgttttg cgacattttg cgacaccatg tggtcacgct gggtatttaa 4260
gcccgagtga gcacgcaggg tctccatttt gaagcgggag gtttgaacgc gcagccgcca 4320
agccgaattc tgcagatatc catcacactg gcggccgctc gactagagcg gccgccaccg 4380
cggtggagct ccagcttttg ttccctttag tgagggttaa ttgcgcgctt ggcgtaatca 4440
tggtcatagc tgtttcctgt gtgaaattgt tatccgctca caattccaca caacatacga 4500
gccggaagca taaagtgtaa agcctggggt gcctaatgag tgagctaact cacattaatt 4560
gcgttgcgct cactgcccgc tttccagtcg ggaaacctgt cgtgccagct gcattaatga 4620
atcggccaac gcgcggggag aggcggtttg cgtattgggc gctcttccgc ttcctcgctc 4680
actgactcgc tgcgctcggt cgttcggctg cggcgagcgg tatcagctca ctcaaaggcg 4740
gtaatacggt tatccacaga atcaggggat aacgcaggaa agaacatgtg agcaaaaggc 4800
cagcaaaagg ccaggaaccg taaaaaggcc gcgttgctgg cgtttttcca taggctccgc 4860
ccccctgacg agcatcacaa aaatcgacgc tcaagtcaga ggtggcgaaa cccgacagga 4920
ctataaagat accaggcgtt tccccctgga agctccctcg tgcgctctcc tgttccgacc 4980
ctgccgctta ccggatacct gtccgccttt ctcccttcgg gaagcgtggc gctttctcat 5040
agctcacgct gtaggtatct cagttcggtg taggtcgttc gctccaagct gggctgtgtg 5100
cacgaacccc ccgttcagcc cgaccgctgc gccttatccg gtaactatcg tcttgagtcc 5160
aacccggtaa gacacgactt atcgccactg gcagcagcca ctggtaacag gattagcaga 5220
gcgaggtatg taggcggtgc tacagagttc ttgaagtggt ggcctaacta cggctacact 5280
agaagaacag tatttggtat ctgcgctctg ctgaagccag ttaccttcgg aaaaagagtt 5340
ggtagctctt gatccggcaa acaaaccacc gctggtagcg gtggtttttt tgtttgcaag 5400
cagcagatta cgcgcagaaa aaaaggatct caagaagatc ctttgatctt ttctacgggg 5460
tctgacgctc agtggaacga aaactcacgt taagggattt tggtcatgag attatcaaaa 5520
aggatcttca cctagatcct tttaaattaa aaatgaagtt ttaaatcaat ctaaagtata 5580
tatgagtaaa cttggtctga cagttaccaa tgcttaatca gtgaggcacc tatctcagcg 5640
atctgtctat ttcgttcatc catagttgcc tgactccccg tcgtgtagat aactacgata 5700
cgggagggct taccatctgg ccccagtgct gcaatgatac cgcgagaccc acgctcaccg 5760
gctccagatt tatcagcaat aaaccagcca gccggaaggg ccgagcgcag aagtggtcct 5820
gcaactttat ccgcctccat ccagtctatt aattgttgcc gggaagctag agtaagtagt 5880
tcgccagtta atagtttgcg caacgttgtt gccattgcta caggcatcgt ggtgtcacgc 5940
tcgtcgtttg gtatggcttc attcagctcc ggttcccaac gatcaaggcg agttacatga 6000
tcccccatgt tgtgcaaaaa agcggttagc tccttcggtc ctccgatcgt tgtcagaagt 6060
aagttggccg cagtgttatc actcatggtt atggcagcac tgcataattc tcttactgtc 6120
atgccatccg taagatgctt ttctgtgact ggtgagtact caaccaagtc attctgagaa 6180
tagtgtatgc ggcgaccgag ttgctcttgc ccggcgtcaa tacgggataa taccgcgcca 6240
catagcagaa ctttaaaagt gctcatcatt ggaaaacgtt cttcggggcg aaaactctca 6300
aggatcttac cgctgttgag atccagttcg atgtaaccca ctcgtgcacc caactgatct 6360
tcagcatctt ttactttcac cagcgtttct gggtgagcaa aaacaggaag gcaaaatgcc 6420
gcaaaaaagg gaataagggc gacacggaaa tgttgaatac tcatactctt cctttttcaa 6480
tattattgaa gcatttatca gggttattgt ctcatgagcg gatacatatt tgaatgtatt 6540

-continued tagaaaaata aacaaatagg ggttccgcgc acatttcccc gaaaagtgcc acctaaattg 6600
taagcgttaa tattttgtta aaattcgcgt taaatttttg ttaaatcagc tcatttttta 6660
accaataggc cgaaatcggc aaaatccctt ataaatcaaa agaatagacc gagatagggt 6720
tgagtgttgt tccagtttgg aacaagagtc cactattaaa gaacgtggac tccaacgtca 6780
aagggcgaaa aaccgtctat cagggcgatg gcccactacg tgaaccatca ccctaatcaa 6840 gtttttttggg gtcgaggtgc cgtaaagcac taaatcggaa ccctaaaggg agcccccgat 6900
ttagagcttg acggggaaag ccggcgaacg tggcgagaaa ggaagggaag aaagcgaaag 6960
gagcgggcgc tagggcgctg gcaagtgtag cggtcacgct gcgcgtaacc accacacccg 7020
ccgcgcttaa tgcgccgcta cagggcgcgt cccattcgcc attcaggctg cgcaactgtt 7080
gggaagggcg atcggtgcgg gcctcttcgc tattacgcca gctggcgaaa gggggatgtg 7140
ctgcaaggcg attaagttgg gtaacgccag ggttttccca gtcacgacgt tgtaaaacga 7200
cggccagtga gcgcgcgtaa tacgactcac tatagggcga attgggtacc gggccccccc 7260
tcgatcgagg tcgacggtat cgggggagct cgcagggtct ccattttgaa gcgggaggtt 7320
tgaacgcgca gccgcc 7336

<210> SEQ ID NO 44
<211> LENGTH: 7336
<212> TYPE: DNA
<213> ORGANISM: Artificial Sequence
<220> FEATURE:
<223> OTHER INFORMATION: constructed sequence

<400> SEQUENCE: 44
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggctct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200

-continued

```
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
caacctctct gagggcattc gcgagtggtg ggcgctgaaa cctggagccc cgaagcccaa   1980
agccaaccag caaaagcagg acgacggccg gggtctggtg cttcctggct acaagtacct   2040
cggacccttc aacggactcg acaaggggga gcccgtcaac gcggcggacg cagcggccct   2100
cgagcacgac aaggcctacg accagcagct gcaggcgggt gacaatccgt acctgcggta   2160
taaccacgcc gacgccgagt ttcaggagcg tctgcaagaa gatacgtctt ttgggggcaa   2220
cctcgggcga gcagtcttcc aggccaagaa gcgggttctc gaacctctcg gtctggttga   2280
ggaaggcgct aagacggctc ctggaaagaa gagaccggta gagccatcac cccagcgttc   2340
tccagactcc tctacgggca tcggcaagaa aggccaacag cccgccagaa aaagactcaa   2400
ttttggtcag actggcgact cagagtcagt tccagaccct caacctctcg gagaacctcc   2460
agcagcgccc tctggtgtgg gacctaatac aatggctgca ggcggtggcg caccaatggc   2520
agacaataac gaaggcgccg acggagtggg tagttcctcg ggaaattggc attgcgattc   2580
cacatggctg ggcgacagag tcatcaccac cagcacccga acctgggccc tgcccaccta   2640
caacaaccac ctctacaagc aaatctccaa cgggacatcg ggaggagcca ccaacgacaa   2700
cacctacttc ggctacagca ccccctgggg gtattttgac tttaacagat tccactgcca   2760
cttttcacca cgtgactggc agcgactcat caacaacaac tggggattcc ggcccaagag   2820
actcagcttc aagctcttca acatccaggt caaggaggtc acgcagaatg aaggcaccaa   2880
gaccatcgcc aataacctca ccagcaccat ccaggtgttt acggactcgg agtaccagct   2940
gccgtacgtt ctcggctctg cccaccaggg ctgcctgcct ccgttcccgg cggacgtgtt   3000
catgattccc cagtacggct acctaacact caacaacggt agtcaggccg tgggacgctc   3060
ctccttctac tgcctggaat actttccttc gcagatgctg agaaccggca acaacttcca   3120
gtttacttac accttcgagg acgtgccttt ccacagcagc tacgcccaca gccagagctt   3180
ggaccggctg atgaatcctc tgattgacca gtacctgtac tacttgtctc ggactcaaac   3240
aacaggaggc acggcaaata cgcagactct gggcttcagc caaggtgggc ctaatacaat   3300
ggccaatcag gcaaagaact ggctgccagg accctgttac cgccaacaac gcgtctcaac   3360
gacaaccggg caaaacaaca atagcaactt tgcctggact gctgggacca aataccatct   3420
gaatggaaga aattcattgg ctaatcctgg catcgctatg gcaacacaca aagacgacga   3480
ggagcgtttt tttcccagta acgggatcct gatttttggc aaacaaaatg ctgccagaga   3540
caatgcggat tacagcgatg tcatgctcac cagcgaggaa gaaatcaaaa ccactaaccc   3600
```

```
tgtggctaca gaggaatacg gtatcgtggg tgataacttg cagttgtata acacggctcc   3660
tggttcggtg tttgtcaaca gccagggggc cttacccggt atggtctggc agaaccggga   3720
cgtgtacctg cagggtccca tctgggccaa gattcctcac acggacggca acttccaccc   3780
gtctccgctg atgggcggct ttggcctgaa acatcctccg cctcagatcc tgatcaagaa   3840
cacgcctgta cctgcggatc ctccgaccac cttcaaccag tcaaagctga actctttcat   3900
cacgcaatac agcaccggac aggtcagcgt ggaaattgaa tgggagctgc agaaggaaaa   3960
cagcaagcgc tggaaccccg agatccagta cacctccaac tactacaaat ctacaagtgt   4020
ggactttgct gttaatacag aaggcgtgta ctctgaaccc cgccccattg gcacccgtta   4080
cctcacccgt aatctgtaat tgcctgttaa tcaataaacc ggttgattcg tttcagttga   4140
actttggtct ctgcgaaggg cgaattcgtt taaacctgca ggactagagg tcctgtatta   4200
gaggtcacgt gagtgttttg cgacattttg cgacaccatg tggtcacgct gggtatttaa   4260
gcccgagtga gcacgcaggg tctccatttt gaagcgggag gtttgaacgc gcagccgcca   4320
agccgaattc tgcagatatc catcacactg gcggccgctc gactagagcg gccgccaccg   4380
cggtggagct ccagcttttg ttccctttag tgagggttaa ttgcgcgctt ggcgtaatca   4440
tggtcatagc tgtttcctgt gtgaaattgt tatccgctca caattccaca caacatacga   4500
gccggaagca taaagtgtaa agcctggggt gcctaatgag tgagctaact cacattaatt   4560
gcgttgcgct cactgcccgc tttccagtcg ggaaacctgt cgtgccagct gcattaatga   4620
atcggccaac gcgcggggag aggcggtttg cgtattgggc gctcttccgc ttcctcgctc   4680
actgactcgc tgcgctcggt cgttcggctg cggcgagcgg tatcagctca ctcaaaggcg   4740
gtaatacggt tatccacaga atcaggggat aacgcaggaa agaacatgtg agcaaaaggc   4800
cagcaaaagg ccaggaaccg taaaaaggcc gcgttgctgg cgtttttcca taggctccgc   4860
ccccctgacg agcatcacaa aaatcgacgc tcaagtcaga ggtggcgaaa cccgacagga   4920
ctataaagat accaggcgtt tccccctgga agctccctcg tgcgctctcc tgttccgacc   4980
ctgccgctta ccggatacct gtccgccttt ctcccttcgg gaagcgtggc gctttctcat   5040
agctcacgct gtaggtatct cagttcggtg taggtcgttc gctccaagct gggctgtgtg   5100
cacgaacccc ccgttcagcc cgaccgctgc gccttatccg gtaactatcg tcttgagtcc   5160
aacccggtaa gacacgactt atcgccactg gcagcagcca ctggtaacag gattagcaga   5220
gcgaggtatg taggcggtgc tacagagttc ttgaagtggt ggcctaacta cggctacact   5280
agaagaacag tatttggtat ctgcgctctg ctgaagccag ttaccttcgg aaaaagagtt   5340
ggtagctctt gatccggcaa acaaaccacc gctggtagcg gtggtttttt tgtttgcaag   5400
cagcagatta cgcgcagaaa aaaaggatct caagaagatc ctttgatctt ttctacgggg   5460
tctgacgctc agtggaacga aaactcacgt taagggattt tggtcatgag attatcaaaa   5520
aggatcttca cctagatcct tttaaattaa aaatgaagtt ttaaatcaat ctaaagtata   5580
tatgagtaaa cttggtctga cagttaccaa tgcttaatca gtgaggcacc tatctcagcg   5640
atctgtctat ttcgttcatc catagttgcc tgactccccg tcgtgtagat aactacgata   5700
cgggagggct taccatctgg ccccagtgct gcaatgatac cgcgagaccc acgctcaccg   5760
gctccagatt tatcagcaat aaaccagcca gccggaaggg ccgagcgcag aagtggtcct   5820
gcaactttat ccgcctccat ccagtctatt aattgttgcc gggaagctag agtaagtagt   5880
tcgccagtta atagtttgcg caacgttgtt gccattgcta caggcatcgt ggtgtcacgc   5940
```

-continued

```
tcgtcgtttg gtatggcttc attcagctcc ggttcccaac gatcaaggcg agttacatga   6000

tcccccatgt tgtgcaaaaa agcggttagc tccttcggtc ctccgatcgt tgtcagaagt   6060

aagttggccg cagtgttatc actcatggtt atggcagcac tgcataattc tcttactgtc   6120

atgccatccg taagatgctt ttctgtgact ggtgagtact caaccaagtc attctgagaa   6180

tagtgtatgc ggcgaccgag ttgctcttgc ccggcgtcaa tacgggataa taccgcgcca   6240

catagcagaa ctttaaaagt gctcatcatt ggaaaacgtt cttcggggcg aaaactctca   6300

aggatcttac cgctgttgag atccagttcg atgtaaccca ctcgtgcacc caactgatct   6360

tcagcatctt ttactttcac cagcgtttct gggtgagcaa aaacaggaag gcaaaatgcc   6420

gcaaaaaagg gaataagggc gacacggaaa tgttgaatac tcatactctt cctttttcaa   6480

tattattgaa gcatttatca gggttattgt ctcatgagcg gatacatatt tgaatgtatt   6540

tagaaaaata aacaaatagg ggttccgcgc acatttcccc gaaaagtgcc acctaaattg   6600

taagcgttaa tattttgtta aaattcgcgt taaatttttg ttaaatcagc tcatttttta   6660

accaataggc cgaaatcggc aaaatccctt ataaatcaaa agaatagacc gagatagggt   6720

tgagtgttgt tccagtttgg aacaagagtc cactattaaa gaacgtggac tccaacgtca   6780

aagggcgaaa aaccgtctat cagggcgatg gcccactacg tgaaccatca ccctaatcaa   6840

gtttttgggg gtcgaggtgc cgtaaagcac taaatcggaa ccctaaaggg agcccccgat   6900

ttagagcttg acggggaaag ccggcgaacg tggcgagaaa ggaagggaag aaagcgaaag   6960

gagcgggcgc tagggcgctg gcaagtgtag cggtcacgct gcgcgtaacc accacacccg   7020

ccgcgcttaa tgcgccgcta cagggcgcgt cccattcgcc attcaggctg cgcaactgtt   7080

gggaagggcg atcggtgcgg gcctcttcgc tattacgcca gctggcgaaa gggggatgtg   7140

ctgcaaggcg attaagttgg gtaacgccag ggttttccca gtcacgacgt tgtaaaacga   7200

cggccagtga gcgcgcgtaa tacgactcac tatagggcga attgggtacc gggccccccc   7260

tcgatcgagg tcgacggtat cgggggagct cgcagggtct ccattttgaa gcgggaggtt   7320

tgaacgcgca gccgcc                                                  7336
```

<210> SEQ ID NO 45
<211> LENGTH: 90
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t

<400> SEQUENCE: 45
ctacagagga atacggtatc gtgnnkgata acttgcagnn knnkaacacg gctcctnnkn 60
nknnknnkgt caacagccag ggggccttac 90

<210> SEQ ID NO 46
<211> LENGTH: 20
<212> TYPE: DNA
<213> ORGANISM: Artificial Sequence
<220> FEATURE:
<223> OTHER INFORMATION: Constructed sequence

<400> SEQUENCE: 46
tggaccggct gatgaatcct 20

<210> SEQ ID NO 47
<211> LENGTH: 20
<212> TYPE: DNA
<213> ORGANISM: Artificial Sequence
<220> FEATURE:
<223> OTHER INFORMATION: Constructed sequence

<400> SEQUENCE: 47
cggtgctgta ttgcgtgatg 20

<210> SEQ ID NO 48
<211> LENGTH: 34
<212> TYPE: DNA
<213> ORGANISM: Artificial Sequence
<220> FEATURE:
<223> OTHER INFORMATION: Constructed sequence

<400> SEQUENCE: 48
ggctcacgtc tctgtagcca cagggttagt ggtt 34

<210> SEQ ID NO 49
<211> LENGTH: 36
<212> TYPE: DNA
<213> ORGANISM: Artificial Sequence
<220> FEATURE:
<223> OTHER INFORMATION: Constructed sequence

<400> SEQUENCE: 49
cggacacgtc tcgctacaga ggaatacggt atcgtg 36

<210> SEQ ID NO 50
<211> LENGTH: 30
<212> TYPE: DNA
<213> ORGANISM: Artificial Sequence
<220> FEATURE:
<223> OTHER INFORMATION: Constructed sequence

<400> SEQUENCE: 50
ggctcacgtc tcggtaaggc cccctggctg 30

<210> SEQ ID NO 51
<211> LENGTH: 36
<212> TYPE: DNA
<213> ORGANISM: Artificial Sequence
<220> FEATURE:
<223> OTHER INFORMATION: Constructed sequence

<400> SEQUENCE: 51
cggacacgtc tccttacccg gtatggtctg gcagaa 36

<210> SEQ ID NO 52
<211> LENGTH: 20
<212> TYPE: DNA
<213> ORGANISM: Artificial Sequence
<220> FEATURE:
<223> OTHER INFORMATION: Constructed sequence

<400> SEQUENCE: 52
cacgcagaat gaaggcacca 20

<210> SEQ ID NO 53
<211> LENGTH: 27
<212> TYPE: DNA
<213> ORGANISM: Artificial Sequence
<220> FEATURE:
<223> OTHER INFORMATION: Constructed sequence

<400> SEQUENCE: 53
cacgataccg tattcctctg tagccac 27

<210> SEQ ID NO 54
<211> LENGTH: 30
<212> TYPE: DNA
<213> ORGANISM: Artificial Sequence
<220> FEATURE:
<223> OTHER INFORMATION: Constructed sequence

<400> SEQUENCE: 54
gctggtttag tgaaccgtca gatcctgcat 30

<210> SEQ ID NO 55
<211> LENGTH: 20
<212> TYPE: DNA
<213> ORGANISM: Artificial Sequence
<220> FEATURE:
<223> OTHER INFORMATION: Constructed sequence

<400> SEQUENCE: 55
aaggtgcgcg tggaccagaa 20

<210> SEQ ID NO 56
<211> LENGTH: 22
<212> TYPE: DNA
<213> ORGANISM: Artificial Sequence
<220> FEATURE:
<223> OTHER INFORMATION: Constructed sequence

<400> SEQUENCE: 56
acaggtactg gtcaatcaga gg 22

<210> SEQ ID NO 57
<211> LENGTH: 65
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 57
caaccacctc tacaagcaaa tctccnnknn knnknnknnk ggagccacca acgacaacac 60
ctact 65

<210> SEQ ID NO 58
<211> LENGTH: 65
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 58
agtaggtgtt gtcgttggtg gctccmnnmn nmnnmnnmnn ggagatttgc ttgtagaggt 60
ggttg 65

<210> SEQ ID NO 59
<211> LENGTH: 64
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)

<223> OTHER INFORMATION: n is a, c, g, or t

<400> SEQUENCE: 59
ctacttgtct cggactcaaa caacannknn knnknnknnk acgcagactc tgggcttcag 60
ccaa 64

<210> SEQ ID NO 60
<211> LENGTH: 64
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 60
ttggctgaag cccagagtct gcgtmnnmnn mnnmnnmnnt gttgtttgag tccgagacaa 60
gtag 64

<210> SEQ ID NO 61
<211> LENGTH: 65
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 61
gatttttggc aaacaaaatg ctgccnnknn knnknnknnk tacagcgatg tcatgctcac 60
cagcg 65

<210> SEQ ID NO 62
<211> LENGTH: 65

<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 62
cgctggtgag catgacatcg ctgtamnnmn nmnnmnnmnn ggcagcattt tgtttgccaa 60
aaatc 65

<210> SEQ ID NO 63
<211> LENGTH: 36
<212> TYPE: DNA
<213> ORGANISM: Artificial Sequence
<220> FEATURE:
<223> OTHER INFORMATION: Constructed sequence

<400> SEQUENCE: 63
cggtcacgtc tcggtcatca ccaccagcac ccgaac 36

<210> SEQ ID NO 64
<211> LENGTH: 31
<212> TYPE: DNA
<213> ORGANISM: Artificial Sequence
<220> FEATURE:
<223> OTHER INFORMATION: Constructed sequence

<400> SEQUENCE: 64
gccagtcgtc tccgttgtcg ttggtggctc c 31

<210> SEQ ID NO 65
<211> LENGTH: 55
<212> TYPE: DNA
<213> ORGANISM: Artificial Sequence
<220> FEATURE:
<223> OTHER INFORMATION: Constructed sequence

<400> SEQUENCE: 65
cggtcacgtc tcgcctctga ttgaccagta cctgtactac ttgtctcgga ctcaa 55

<210> SEQ ID NO 66
<211> LENGTH: 52
<212> TYPE: DNA
<213> ORGANISM: Artificial Sequence
<220> FEATURE:
<223> OTHER INFORMATION: Constructed sequence

<400> SEQUENCE: 66
gccagtcgtc tccgccattg tattaggccc accttggctg aagcccagag tc 52

<210> SEQ ID NO 67
<211> LENGTH: 58
<212> TYPE: DNA
<213> ORGANISM: Artificial Sequence
<220> FEATURE:
<223> OTHER INFORMATION: Constructed sequence

<400> SEQUENCE: 67
ttaccccaca ggaagcacgc cacctgcaaa tcaggtatgg ctgccgatgg ttatcttc 58

<210> SEQ ID NO 68
<211> LENGTH: 56
<212> TYPE: DNA
<213> ORGANISM: Artificial Sequence
<220> FEATURE:
<223> OTHER INFORMATION: Constructed sequence

<400> SEQUENCE: 68
ctcgttctct gccgtgtggg actagttaca gattacgggt gaggtaacgg gtgcca 56

<210> SEQ ID NO 69
<211> LENGTH: 15
<212> TYPE: PRT
<213> ORGANISM: Unknown
<220> FEATURE:
<223> OTHER INFORMATION: major ADK8 epitope in AAV8 HVR.VIII region

<400> SEQUENCE: 69

Ala Asp Asn Leu Gln Gln Gln Asn Thr Ala Pro Gln Ile Gly Thr
1 5 10 15

<210> SEQ ID NO 70
<211> LENGTH: 15
<212> TYPE: PRT
<213> ORGANISM: Unknown
<220> FEATURE:
<223> OTHER INFORMATION: mutated c41 ADK8 epitope in AAV8 HVR.VIII region

<400> SEQUENCE: 70

Gly Asp Asn Leu Gln Leu Tyr Asn Thr Ala Pro Gly Ser Val Phe
1 5 10 15

<210> SEQ ID NO 71
<211> LENGTH: 15
<212> TYPE: PRT
<213> ORGANISM: Unknown
<220> FEATURE:
<223> OTHER INFORMATION: mutated c42 ADK8 epitope in AAV8 HVR.VIII region

<400> SEQUENCE: 71

Ser Asp Asn Leu Gln Phe Arg Asn Thr Ala Pro Leu Trp Ser Ser
1 5 10 15

<210> SEQ ID NO 72
<211> LENGTH: 15
<212> TYPE: PRT
<213> ORGANISM: Unknown
<220> FEATURE:
<223> OTHER INFORMATION: mutated c46 ADK8 epitope in AAV8 HVR.VIII region

<400> SEQUENCE: 72

Asn Asp Asn Leu Gln Val Cys Asn Thr Ala Pro Asp Asp Val Met
1 5 10 15

<210> SEQ ID NO 73
<211> LENGTH: 15
<212> TYPE: PRT
<213> ORGANISM: Unknown
<220> FEATURE:
<223> OTHER INFORMATION: mutated g110 ADK8 epitope in AAV8 HVR.VIII region

<400> SEQUENCE: 73

Cys Asp Asn Leu Gln Gly Tyr Asn Thr Ala Pro Leu Cys Val Ala
1 5 10 15

<210> SEQ ID NO 74
<211> LENGTH: 15
<212> TYPE: PRT
<213> ORGANISM: Unknown
<220> FEATURE:
<223> OTHER INFORMATION: mutated g112 ADK8 epitope in AAV8 HVR.VIII region

<400> SEQUENCE: 74

Val Asp Asn Leu Gln Phe Leu Asn Thr Ala Pro Ala Gly Glu Ala
1 5 10 15

<210> SEQ ID NO 75
<211> LENGTH: 15
<212> TYPE: PRT
<213> ORGANISM: Unknown
<220> FEATURE:
<223> OTHER INFORMATION: mutated g113 ADK8 epitope in AAV8 HVR.VIII region

<400> SEQUENCE: 75

Leu Asp Asn Leu Gln Asp Gly Asn Thr Ala Pro Gly Ala Cys Gly
1 5 10 15

<210> SEQ ID NO 76
<211> LENGTH: 15
<212> TYPE: PRT
<213> ORGANISM: Unknown
<220> FEATURE:
<223> OTHER INFORMATION: mutated g115 ADK8 epitope in AAV8 HVR.VIII region

<400> SEQUENCE: 76

Trp Asp Asn Leu Gln Ser Glu Asn Thr Ala Pro Ser Glu Thr Ser
1 5 10 15

<210> SEQ ID NO 77
<211> LENGTH: 15
<212> TYPE: PRT
<213> ORGANISM: Unknown
<220> FEATURE:
<223> OTHER INFORMATION: mutated g117 ADK8 epitope in AAV8 HVR.VIII region

<400> SEQUENCE: 77

Ser Asp Asn Leu Gln Ser Cys Asn Thr Ala Pro Phe Ala Gly Ala
1 5 10 15

<210> SEQ ID NO 78
<211> LENGTH: 5
<212> TYPE: PRT
<213> ORGANISM: Artificial Sequence
<220> FEATURE:
<223> OTHER INFORMATION: Constructed sequence

<400> SEQUENCE: 78

Asn Gly Thr Ser Gly
1 5

<210> SEQ ID NO 79
<211> LENGTH: 4
<212> TYPE: PRT
<213> ORGANISM: Artificial Sequence
<220> FEATURE:
<223> OTHER INFORMATION: Constructed sequence

<400> SEQUENCE: 79

Ser Gly Thr His
1

<210> SEQ ID NO 80
<211> LENGTH: 4
<212> TYPE: PRT
<213> ORGANISM: Artificial Sequence
<220> FEATURE:
<223> OTHER INFORMATION: Constructed sequence

<400> SEQUENCE: 80

Ser Asp Thr His
1

<210> SEQ ID NO 81
<211> LENGTH: 5
<212> TYPE: PRT
<213> ORGANISM: Artificial Sequence
<220> FEATURE:
<223> OTHER INFORMATION: Constructed sequence

<400> SEQUENCE: 81

Gly Gly Thr Ala Asn
1 5

<210> SEQ ID NO 82
<211> LENGTH: 5
<212> TYPE: PRT
<213> ORGANISM: Artificial Sequence
<220> FEATURE:
<223> OTHER INFORMATION: Constructed sequence

<400> SEQUENCE: 82

Asp Gly Ser Gly Leu
1 5

<210> SEQ ID NO 83
<211> LENGTH: 15
<212> TYPE: DNA
<213> ORGANISM: Artificial Sequence
<220> FEATURE:
<223> OTHER INFORMATION: Constructed sequence

<400> SEQUENCE: 83
aacgggacat cggga 15

<210> SEQ ID NO 84
<211> LENGTH: 12
<212> TYPE: DNA
<213> ORGANISM: Artificial Sequence
<220> FEATURE:
<223> OTHER INFORMATION: Constructed sequence

<400> SEQUENCE: 84
tctggtactc at 12

<210> SEQ ID NO 85
<211> LENGTH: 90
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t

<400> SEQUENCE: 85
ctacagagga atacggtatc gtgnnkgata acttgcagnn knnkaacacg gctcctnnkn 60
nknnknnkgt caacagccag ggggccttac 90

<210> SEQ ID NO 86
<211> LENGTH: 65
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 86
caaccacctc tacaagcaaa tctccnnknn knnknnknnk ggagccacca acgacaacac 60
ctact 65

<210> SEQ ID NO 87

<211> LENGTH: 64
<212> TYPE: DNA
<213> ORGANISM: Artificial Sequence
<220> FEATURE:
<223> OTHER INFORMATION: Constructed sequence
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 87
ctacttgtct cggactcaaa caacannknn knnknnknnk acgcagactc tgggcttcag     60
ccaa                                                                  64

<210> SEQ ID NO 88
<211> LENGTH: 738
<212> TYPE: PRT
<213> ORGANISM: Unknown
<220> FEATURE:
<223> OTHER INFORMATION: AAV rh.20 capsid protein

<400> SEQUENCE: 88

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly

-continued

```
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620
```

-continued

```
Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```